US012577585B2

(12) United States Patent
Almassian et al.

(10) Patent No.: US 12,577,585 B2
(45) Date of Patent: Mar. 17, 2026

(54) COMPOSITIONS AND METHODS OF USE OF ONCOLYTIC VIRUS LIKE VESICLES

(71) Applicant: Carogen Corporation, Farmington, CT (US)

(72) Inventors: Bijan Almassian, Cheshire, CT (US); Valerian Nakaar, Hamden, CT (US); Xianyong Ma, Woodbridge, CT (US); Bhaskara Reddy Madina, South Windsor, CT (US); Kepeng Wang, Farmington, CT (US); Timur Yarovinsky, Woodbridge, CT (US)

(73) Assignee: Carogen Corporation, Farmington, CT (US)

( * ) Notice: Subject to any disclaimer, the term of this patent is extended or adjusted under 35 U.S.C. 154(b) by 846 days.

(21) Appl. No.: 17/791,873

(22) PCT Filed: Jan. 8, 2021

(86) PCT No.: PCT/US2021/012834
§ 371 (c)(1),
(2) Date: Jul. 8, 2022

(87) PCT Pub. No.: WO2021/142366
PCT Pub. Date: Jul. 15, 2021

(65) Prior Publication Data
US 2023/0063041 A1 Mar. 2, 2023

Related U.S. Application Data

(60) Provisional application No. 62/959,435, filed on Jan. 10, 2020.

(51) Int. Cl.
*C12N 15/86* (2006.01)
*A61K 35/766* (2015.01)
(Continued)

(52) U.S. Cl.
CPC ............ *C12N 15/86* (2013.01); *A61K 35/766* (2013.01); *C07K 14/005* (2013.01);
(Continued)

(58) Field of Classification Search
None
See application file for complete search history.

(56) References Cited

U.S. PATENT DOCUMENTS 9,987,353 B2   6/2018   Robek et al.
10,435,712 B2   10/2019   Rose et al.
(Continued)

FOREIGN PATENT DOCUMENTS

CA        2547922 A1    6/2005
JP     2004-500325 A    1/2004
(Continued)

OTHER PUBLICATIONS

Michel et al., Journal of Hepatology, 2011, vol. 54, pp. 1286-1296 (Year: 2011).*
(Continued)

*Primary Examiner* — Evelyn Y Pyla
(74) *Attorney, Agent, or Firm* — Wiggin and Dana LLP

(57) ABSTRACT

The present invention relates to high-titer hybrid virus vectors which produce virus-like vesicle (VLVs) and compositions and methods thereof for targeting a malignancy or infectious disease. VLVs are a capsid-free, self-replicating artificial virus platform carrying positive-strand capped and polyadenylated RNA encoding an in vitro evolved Semliki Forest virus (SFV) RNA-dependent RNA replicase and the vesicular stomatitis virus (VSV) glycoprotein. The VLVs of the present invention and pharmaceutical compositions thereof encode for polynucleotide and/or polypeptide thera-
(Continued)

peutic agents useful in methods for the treatment, prophylaxis, and prevention of malignancies and infectious diseases.

21 Claims, 17 Drawing Sheets

Specification includes a Sequence Listing.

(51) Int. Cl.

| | |
|---|---|
| *C07K 14/005* | (2006.01) |
| *C07K 14/54* | (2006.01) |
| *C07K 14/715* | (2006.01) |

(52) U.S. Cl.
CPC ...... *C07K 14/5418* (2013.01); *C07K 14/5434* (2013.01); *C07K 14/7155* (2013.01); *C12N 2760/20222* (2013.01); *C12N 2760/20232* (2013.01); *C12N 2760/20243* (2013.01); *C12N 2760/20244* (2013.01); *C12N 2770/36122* (2013.01); *C12N 2770/36132* (2013.01); *C12N 2770/36143* (2013.01); *C12N 2770/36144* (2013.01)

(56) References Cited

U.S. PATENT DOCUMENTS

| | | | | |
|---|---|---|---|---|
| 2012/0213813 | A1* | 8/2012 | Smith | A61P 35/00 |
| | | | | 424/274.1 |
| 2017/0056493 | A1 | 3/2017 | Robek et al. | |
| 2020/0297840 | A1 | 9/2020 | Rubido et al. | |

FOREIGN PATENT DOCUMENTS

| | | |
|---|---|---|
| JP | 2017-515509 A | 6/2017 |
| JP | 2019-527737 A | 10/2019 |
| WO | 0069463 A1 | 11/2000 |
| WO | 2008119827 A1 | 10/2008 |
| WO | 2009141431 A1 | 11/2009 |
| WO | 2015175382 A1 | 11/2015 |
| WO | 2018027316 A1 | 2/2018 |
| WO | 2019057974 A1 | 3/2019 |

OTHER PUBLICATIONS

Klar et al., Cancer Immunol Immunother. Jan. 2020; 6991):57-67, Epub Dec. 4, 2019 (Year: 2019).*

Schramme et al., Cancer Immunology Research; 8(1), pp. 32-45, Jan. 2020, Epub Dec. 5, 2019 (Year: 2019).*

Vasiljeva et al., The Journal of Biological Chemistry, vol. 278, No. 43, issue of Oct. 24, pp. 41636-41645, 2003 (Year: 2003).*

Wykes et al., Nature Reviews, Immunology, vol. 18, Feb. 2018, pp. 91-104 (Year: 2018).*

Xu et al., Molecular Oncology 12 (2018) 936-952 (Year: 2018).*

Zhang et al., World Journal of Gastroenterology 2006, August 7; 12(20): 4727-4735 (Year: 2006).*

Zou et al., Nature Communications, (2019)10:4109, pp. 1-14 (Year: 2019).*

Tracy D. Reynolds et al: "Virus-Like Vesicle-Based Therapeutic Vaccine Vectors for Chronic Hepatitis B Virus Infection", Journal of Virology vol. 89, No. 20, Aug. 5, 2015.

Jia Fan et al: "Pseudo-typed Semliki Forest Virus Delivers EGFP into Neurons" Journal of Neurovirology, Informa Healthcare, GB, vol. 23 No. 2, Oct. 13, 2016.

International Search Report, PCT/US2021/012834, mailed Jan. 8, 2021.

National Center for Biotechnology Information (NCBI), "nonstructural polyprotein [Semliki Forest virus 4] GenBank: AKC01667.1," Apr. 17, 2015. [Online]. Available: https://www.ncbi.nlm.nih.gov/protein/AKC01667.1. [Accessed Aug. 20, 2025].

Nozomi Ito et al. "Surgery, Metabolism and Nutrition", Oct. 2019, vol. 53, No. 5, pp. 267-270.

JP Office Action for corresponding Application No. 2022-542209, mailed Jan. 29, 2025.

Supplementary European Search Report, EP23760858, completed Nov. 7, 2025.

Anonymous, CaroGen, bioCentriq Enter Clinical Manufacturing Pact, Contact Pharma, Jun. 22, 2021, pp. 1-13, XP093333044, Retrieved from the Internet: https://www.contractpharma.com/breaking-news/carogen-biocentriq-enter-clinical-manufacturing-pact/.

Supplementary European Search Report, EP23737787 mailed Jan. 9, 2026.

Taggs: "GMP Manufacture of Clinical Grade Therapeutic Vaccine for the Treatment of Patients With Chronic HBV", May 6, 2018, pp. 1-4, retrieved from the internet: http://taggs.hhs.gov/Detail/AwardDetail?arg_AwardNum=R44DK113858&arg_ProgOfficeCode=119.

Fonseca, Jairo A., et al. "Inclusion of the murine IgGκ signal peptide increases the cellular immunogenicity of a simian adenoviral vectored Plasmodium vivax multistage vaccine." Vaccine 36.20 (2018): 2799-2808.

Ye, B., et al. "T-cell exhaustion in chronic hepatitis B infection: current knowledge and clinical significance." Cell death & disease 6.3 (2015): e1694-e1694.

Chiale, Carolina, et al. "Modified alphavirus-vesiculovirus hybrid vaccine vectors for homologous prime-boost immunotherapy of chronic hepatitis B." Vaccines 8.2 (2020): 279.

\* cited by examiner

Mock                    MOI1                    MOI10

Mock                    MOI1                    MOI10

Dp –G(NJ)-IL12

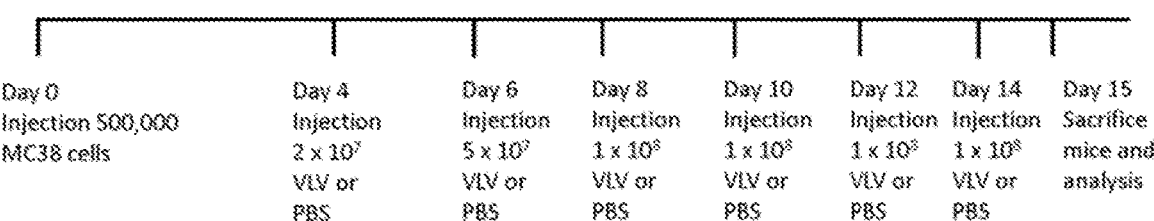

| Day 0<br>Injection 500,000<br>MC38 cells | Day 4<br>Injection<br>$2 \times 10^7$<br>VLV or<br>PBS | Day 6<br>Injection<br>$5 \times 10^7$<br>VLV or<br>PBS | Day 8<br>Injection<br>$1 \times 10^8$<br>VLV or<br>PBS | Day 10<br>Injection<br>$1 \times 10^8$<br>VLV or<br>PBS | Day 12<br>Injection<br>$1 \times 10^8$<br>VLV or<br>PBS | Day 14<br>Injection<br>$1 \times 10^8$<br>VLV or<br>PBS | Day 15<br>Sacrifice<br>mice and<br>analysis |

FIG. 5A

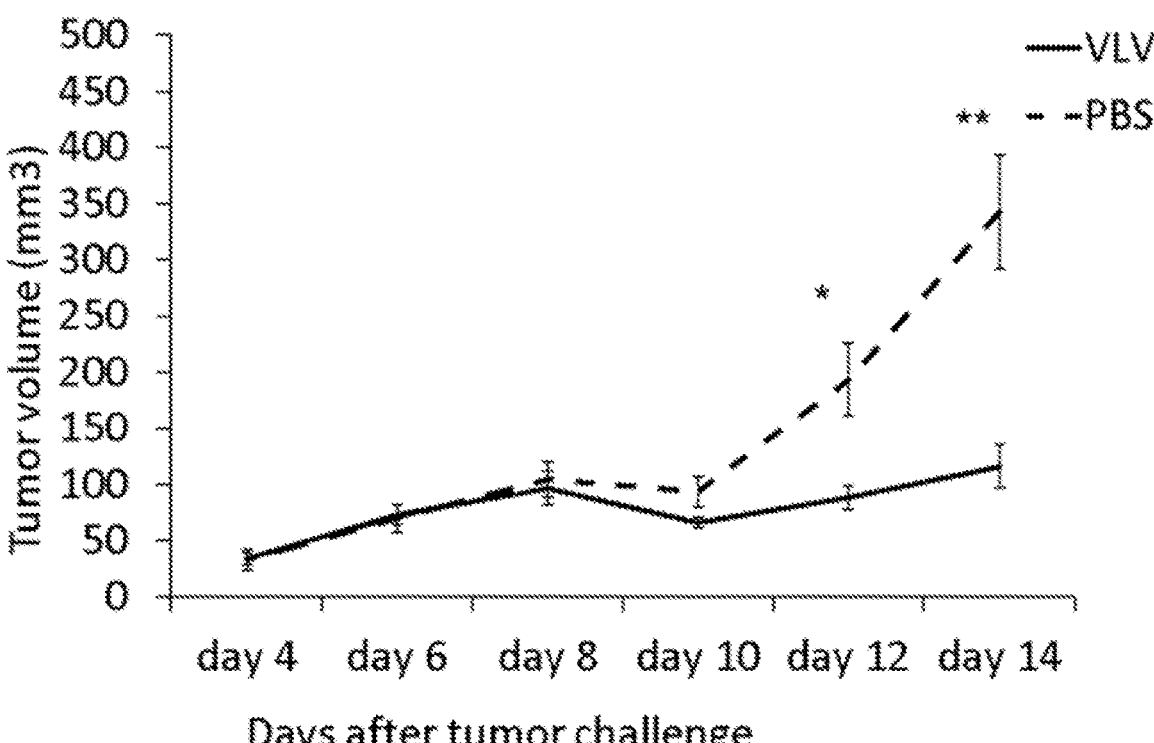

Day 0
Injection
500,000 MC38
cells

Day 15
Injection
1st dose
VLV

Day 17
Injection
2nd dose
VLV

Day 21
Injection
3rd dose
VLV

COMPOSITIONS AND METHODS OF USE OF ONCOLYTIC VIRUS LIKE VESICLES

CROSS-REFERENCE TO RELATED APPLICATIONS

This application is a national phase entry under 35 U.S.C. § 371 of International Application PCT/US2021/012834, which claims priority under 35 U.S.C § 119(e) to U.S. Provisional Application No. 62/959,435, filed Jan. 10, 2020, all of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Jan. 7, 2021, is named 25133-8-104384-101_SL.txt and is 51,554 bytes in size.

FIELD OF THE INVENTION

The present invention relates to high-titer hybrid virus vectors which produce virus-like vesicle (VLVs) and compositions and methods thereof for targeting a malignancy or infectious disease. VLVs are a capsid-free, self-replicating artificial virus platform carrying positive-strand capped and polyadenylated RNA encoding an in vitro evolved Semliki Forest virus (SFV) RNA-dependent RNA replicase and the vesicular stomatitis virus (VSV) glycoprotein. The VLVs of the present invention and pharmaceutical compositions thereof encode for polynucleotide and/or polypeptide therapeutic agents useful in methods for the treatment, prophylaxis, and prevention of malignancies and infectious diseases.

BACKGROUND OF THE INVENTION

Oncolytic viruses may target and specifically replicate in cancer cells resulting in the lysis and/or death of the cancer cells. These viruses may express transgenes that can direct the virus to cancer cells, increase their potential to activate T cell infiltration or activity, or imbue multiple other activities that enhance oncolysis.

Many forms of oncolytic viruses have been composed and clinically tested. However, only a single oncolytic virus has been approved for medical use: talimogene laherparepvec (T-VEC), a genetically modified herpesvirus that expresses a transgene, granulocyte-macrophage colony stimulating factor (GM-CSF) for use in malignant melanoma. Unfortunately, T-VEC has had minimal commercial success due to its limited activity. The lack of success of T-VEC and many other types of oncolytic viruses is likely due to multiple factors, including:

Pre-existing neutralizing antibody immunity;

Rapid clearance via innate immune pathways (complement, interferon pathways);

Transgene expression results in poor viral replication capacity;

Transgene expression may promote immune clearance of the virus;

Inability to induce sufficient innate immune response in the tumor;

Having limited capacity for addition of transgene(s);

Remaining too pathogenic;

Difficult to manufacture at scale.

The viruses that have been used for oncolytic activity include paroviruses, adenoviruses, herpesvirus (as above with T-VEC), poxviruses, picornovirus, alphaviruses, retroviruses, paramyxoviruses, rhabdoviruses, and reoviruses. However, each of these types of viruses have one or more of the deficiencies listed above that have tempered their success.

Virus-like vesicles (VLVs) are a capsid-free, self-replicating artificial virus platform carrying positive-strand capped and polyadenylated RNA encoding an in vitro evolved Semliki Forest virus (SFV) RNA-dependent RNA replicase and the vesicular stomatitis virus (VSV) glycoprotein. VLVs are able to overcome many of the deficiencies harbored by natural virus vectors. As an artificial virus that lacks an encoded capsid protein, VLVs are non-pathogenic. The lack of a capsid protein also avoids any limit to the size of RNA packaged into the VLVs, therefore, allowing a very large capacity for packaging RNA and expression of transgene antigens or proteins. Being derived from animal viruses that are not to be endemic in human populations, pre-existing neutralizing immunity is likely rare or absent. VLVs can be grown to high titers enabling large scale manufacturing. These features of VLVs are ideal for an oncolytic virus.

U.S. Pat. No. 9,987,353 by Robek et al., issued Jun. 5, 2018 and incorporated by reference herein in its entirety, relates to compositions and methods for therapeutic immunization for treatment of chronic hepatitis B using a VLV composition produced from a high-titer hybrid-hepatitis B virus vector.

U.S. Pat. No. 10,435,712 by Rose et al., issued Oct. 8, 2019 and incorporated by reference herein in its entirety, relates to compositions and methods for immunization using high-titer hybrid-virus vectors. The high-titer hybrid virus vectors producing evolved VLV compositions therein comprise alphavirus nonstructural proteins with multiple mutations.

SUMMARY OF THE INVENTION

In some embodiments, the invention relates to a high-titer hybrid virus vector for treatment, prophylaxis, or prevention of malignancy or infectious disease comprising the following operably linked sequence elements:

a) a first DNA sequence comprising a DNA promoter sequence, b) a second DNA sequence encoding alphavirus nonstructural protein polynucleotide sequences, c) a third DNA sequence encoding an alphavirus subgenomic RNA promoter, d) a fourth DNA sequence comprising at least one sequence domain each independently selected from the group consisting of a sequence domain encoding a cytokine agonist polypeptide a sequence domain encoding a cytokine antagonist polypeptide a sequence domain encoding a short hairpin RNA (shRNA), and combinations thereof, e) a fifth DNA sequence encoding a vesiculovirus glycoprotein.

In some embodiments, the invention relates to a high-titer hybrid virus vector for treatment, prophylaxis, or prevention of malignancy or infectious disease, wherein the DNA promoter sequence of the first DNA sequence comprises a constitutive promoter for RNA-dependent RNA polymerases.

In some embodiments, the invention relates to a high-titer hybrid virus vector for treatment, prophylaxis, or prevention of malignancy or infectious disease, wherein the DNA promoter sequence comprises a constitutive promoter for bacteriophage RNA polymerases.

In some embodiments, the invention relates to a high-titer hybrid virus vector for treatment, prophylaxis, or prevention of malignancy or infectious disease, wherein the promoter sequence is a cytomegalovirus (CMV) promoter sequence.

In some embodiments, the invention relates to a high-titer hybrid virus vector for treatment, prophylaxis, or prevention of malignancy or infectious disease, wherein the alphavirus non-structural protein polynucleotide sequences of the second DNA sequence are Semliki Forest virus (SFV) non-structural protein polynucleotide sequences.

In some embodiments, the invention relates to a high-titer hybrid virus vector for treatment, prophylaxis, or prevention of malignancy or infectious disease, wherein the SFV non-structural protein polypeptide sequences encoded by the second DNA sequence comprise one or more amino acid mutations.

In some embodiments, the invention relates to a high-titer hybrid virus vector for treatment, prophylaxis, or prevention of malignancy or infectious disease, wherein the SFV non-structural protein polypeptide sequences comprise a sequence having at least about 70% sequence identity to SEQ ID NO. 13.

In some embodiments, the invention relates to a high-titer hybrid virus vector for treatment, prophylaxis, or prevention of malignancy or infectious disease, wherein the SFV non-structural protein polypeptide sequences comprise SEQ ID NO. 13.

In some embodiments, the invention relates to a high-titer hybrid virus vector for treatment, prophylaxis, or prevention of malignancy or infectious disease, wherein the alphavirus non-structural protein polynucleotide sequences of the second DNA sequence comprise alphavirus RNA-dependent polymerase.

In some embodiments, the invention relates to a high-titer hybrid virus vector for treatment, prophylaxis, or prevention of malignancy or infectious disease, wherein the alphavirus RNA-dependent polymerase is a Semliki Forest virus (SFV) RNA-dependent polymerase.

In some embodiments, the invention relates to a high-titer hybrid virus vector for treatment, prophylaxis, or prevention of malignancy or infectious disease, wherein the alphavirus subgenomic RNA promoter of the third DNA sequence is a Semliki Forest virus (SFV) subgenomic RNA promoter.

In some embodiments, the invention relates to a high-titer hybrid virus vector for treatment, prophylaxis, or prevention of malignancy or infectious disease, wherein the fourth DNA sequence comprises at least one sequence domain encoding a cytokine agonist or antagonist polypeptide each independently selected from the group consisting of IL-2, IL-7, IL-15, IL-18, IL-19, IL-35, IL-21, GM-CSF, IL-17, Flt3L, and combinations thereof.

In some embodiments, the invention relates to a high-titer hybrid virus vector for treatment, prophylaxis, or prevention of malignancy or infectious disease, wherein the fourth DNA sequence comprises at least one sequence domain encoding an shRNA polynucleotide checkpoint inhibitor each independently selected from the group consisting of PD-L2, PD-L1, CTLA-4, LAG-3, TIM-3, TIGIT, CD90, BTLA, CD160, PD-1, and combinations thereof.

In some embodiments, the invention relates to a high-titer hybrid virus vector for treatment, prophylaxis, or prevention of malignancy or infectious disease, wherein the fourth DNA sequence comprises three sequence domains.

In some embodiments, the invention relates to a high-titer hybrid virus vector for treatment, prophylaxis, or prevention of malignancy or infectious disease, wherein the fourth DNA sequence comprises:
a) a sequence domain encoding IL-12,
b) a sequence domain encoding IL-17RA-DN; and
c) a sequence domain encoding PD-L1-shRNA.

In some embodiments, the invention relates to a high-titer hybrid virus vector for treatment, prophylaxis, or prevention of malignancy or infectious disease, wherein the fourth DNA sequence comprises:
a) a sequence domain having at least 70% sequence identity with SEQ ID NO. 6,
b) a sequence domain having at least 70% sequence identity with SEQ ID NO. 8; and
c) a sequence domain having at least 70% sequence identity with SEQ ID NO. 10.

In some embodiments, the invention relates to a high-titer hybrid virus vector for treatment, prophylaxis, or prevention of malignancy or infectious disease, wherein each sequence domain of the fourth DNA sequence is preceded by a sequence independently selected from the group consisting of a subgenomic promoter, a sequence encoding a 2A peptide sequence, or combinations thereof.

In some embodiments, the invention relates to a high-titer hybrid virus vector for treatment, prophylaxis, or prevention of malignancy or infectious disease, wherein the high-titer hybrid virus vector is trivalent; and wherein the fourth DNA sequence consists of three sequence domains.

In some embodiments, the invention relates to a high-titer hybrid virus vector for treatment, prophylaxis, or prevention of malignancy or infectious disease, wherein the fourth DNA sequence consists of:
a) a subgenomic promoter sequence and a sequence domain encoding IL-12,
b) a subgenomic promoter sequence and a sequence domain encoding IL-17RA-DN; and
c) a subgenomic promoter sequence and a sequence domain encoding PD-L1-shRNA.

In some embodiments, the invention relates to a high-titer hybrid virus vector for treatment, prophylaxis, or prevention of malignancy or infectious disease, wherein the fourth DNA sequence consists of:
a) a subgenomic promoter sequence and a sequence domain having at least 70% sequence identity with SEQ ID NO. 6,
b) a subgenomic promoter sequence and a sequence domain having at least 70% sequence identity with SEQ ID NO. 8; and
c) a subgenomic promoter sequence and a sequence domain having at least 70% sequence identity with SEQ ID NO. 10.

In some embodiments, the invention relates to a high-titer hybrid virus vector for treatment, prophylaxis, or prevention of malignancy or infectious disease, wherein the fourth DNA sequence further comprises a sequence domain encoding a polynucleotide or polypeptide inhibitor of an immunosuppressive regulator selected from the group consisting of TDO, IDO1, IDO2, and combinations thereof.

In some embodiments, the invention relates to a high-titer hybrid virus vector for treatment, prophylaxis, or prevention of malignancy or infectious disease, wherein each of the sequence domains of the fourth DNA sequence are expressed under control of single or multiple subgenomic promoters resulting in single or multiple subgenomic RNA.

In some embodiments, the invention relates to a high-titer hybrid virus vector for treatment, prophylaxis, or prevention of malignancy or infectious disease, wherein each of the sequence domains of the fourth DNA sequence are co-translated from the shared subgenomic RNA that includes ribosome skipping 2A peptides.

In some embodiments, the invention relates to a high-titer hybrid virus vector for treatment, prophylaxis, or prevention of malignancy or infectious disease further comprising a sixth DNA sequence comprising an expression cassette expressing single or multiple specific antigens of the malignancy or infectious disease; and In some embodiments, the invention relates to a high-titer hybrid virus vector for treatment, prophylaxis, or prevention of malignancy or infectious disease, wherein the expression cassette expresses specific antigens of a tumor or infectious agent to induce humoral and/or cellular immune responses to the antigens.

In some embodiments, the invention relates to a high-titer hybrid virus vector for treatment, prophylaxis, or prevention of malignancy or infectious disease, wherein the vesiculovirus glycoprotein of the fifth DNA sequence comprises envelope glycoprotein of vesicular stomatitis Indiana virus, vesicular stomatitis New Jersey virus, Chandipura virus or structurally related vesiculoviruses.

In some embodiments, the invention relates to a high-titer hybrid virus vector for treatment, prophylaxis, or prevention of malignancy or infectious disease, wherein titers of at least $5\times10^7$ plaque forming units (pfu) per mL of virus like vesicles (VLVs) are obtained.

In some embodiments, the invention relates to a high-titer hybrid virus vector for treatment, prophylaxis, or prevention of malignancy or infectious disease, wherein titers of at least $1\times10^8$ plaque forming units (pfu) per mL of virus like vesicles (VLVs) are obtained.

In some embodiments, the invention relates to a high-titer hybrid virus vector for generating oncolytic virus-like vesicles (VLVs) comprising the following operably linked sequence elements:

a) a first DNA sequence comprising a DNA promoter sequence, b) a second DNA sequence encoding alphavirus non-structural protein polynucleotide sequences, c) a third DNA sequence encoding an alphavirus subgenomic RNA promoter, d) a fourth DNA sequence comprising an expression cassette expressing single or multiple specific antigens of the malignancy or infectious disease; and e) a fifth DNA sequence encoding a vesiculovirus glycoprotein.

In some embodiments, the invention relates to virus-like vesicles (VLVs) containing replicon RNA generated by a high-titer hybrid virus vector for generating oncolytic virus-like vesicles (VLVs).

In some embodiments, the invention relates to virus-like vesicles (VLVs) containing replicon RNA generated by a high-titer hybrid virus vector for generating oncolytic virus-like vesicles (VLVs), wherein the replicon RNA is positive-strand capped and polyadenylated.

In some embodiments, the invention relates to a composition comprising virus-like vesicles (VLVs) produced by a high-titer hybrid virus vector for treatment, prophylaxis, or prevention of malignancy or infectious disease comprising the following operably linked sequence elements:

a) a first DNA sequence comprising a DNA promoter sequence, b) a second DNA sequence encoding alphavirus non-structural protein polynucleotide sequences, c) a third DNA sequence encoding an alphavirus subgenomic RNA promoter, d) a fourth DNA sequence comprising at least one sequence domain each independently selected from the group consisting of a sequence domain encoding a cytokine agonist polypeptide a sequence domain encoding a cytokine antagonist polypeptide a sequence domain encoding a short hairpin RNA (shRNA), and combinations thereof, e) a fifth DNA sequence encoding a vesiculovirus glycoprotein.

In some embodiments of the invention, the VLVs are self-replicating.

In some embodiments of the invention, the VLVs are oncolytic.

In some embodiments of the invention, the VLVs are capsid-free.

In some embodiments, the invention relates to a method of producing virus-like vesicles (VLVs) for treatment, prophylaxis, or prevention of malignancy or infectious disease comprising the steps of:

a) generating a high-titer virus vector comprising at least one sequence domain each independently selected from the group consisting of a sequence domain encoding a cytokine agonist polypeptide, a sequence domain encoding a cytokine antagonist polypeptide, a sequence domain encoding a short hairpin RNA (shRNA), and combinations thereof, b) transfecting BHK-21 cells with the high-titer virus vector of step (a), c) incubating the transfected BHK-21 cells of step (b) in a buffer solution for a suitable time and at a suitable temperature to propagate VLVs; and d) isolating the VLVs from the BHK-21 cells and buffer solution by a technique selected from the group consisting of ultrafiltration, centrifugation, tangential flow filtration, affinity purification, ion exchange chromatography, and combinations thereof; wherein the isolating of step (d) yields VLVs of a high titer.

In some embodiments, the invention relates to a method of treating and preventing malignancy in a subject, the method comprising administering a therapeutically effective amount of a composition comprising virus-like vesicles (VLVs) produced by a high-titer hybrid virus vector for treatment, prophylaxis, or prevention of malignancy or infectious disease to a mammalian or human subject in need thereof.

In some embodiments, the invention relates to a method of treating a subject having an infectious disease, the method comprising administering a therapeutically effective amount of a composition comprising virus-like vesicles (VLVs) produced by a high-titer hybrid virus vector for treatment, prophylaxis, or prevention of malignancy or infectious disease to a mammalian or human subject in need thereof.

In some embodiments, the invention relates to a method of immunizing a subject against an infectious disease, the method comprising administering a therapeutically effective amount of a composition comprising virus-like vesicles (VLVs) produced by a high-titer hybrid virus vector for treatment, prophylaxis, or prevention of malignancy or infectious disease to a mammalian or human subject in need thereof.

In some embodiments, the invention relates to a method of downregulating genes associated with malignancy, the method comprising administering a therapeutically effective amount of a composition comprising virus-like vesicles (VLVs) produced by a high-titer hybrid virus vector for treatment, prophylaxis, or prevention of malignancy or infectious disease to a mammalian or human subject in need thereof.

In some embodiments, the invention relates to a method of downregulating genes associated with malignancy, the method comprising administering a therapeutically effective amount of a composition comprising virus-like vesicles (VLVs) produced by a high-titer hybrid virus vector for treatment, prophylaxis, or prevention of malignancy or infectious disease to a mammalian or human subject in need thereof, wherein the gene is selected from the group consisting of PD-L1, CXCL1, CXCL2, and combinations thereof.

In some embodiments, the invention is related to methods wherein the mammalian subject in need thereof is a human or animal.

In some embodiments, the invention relates to the use of a composition in the manufacture of a medicament for the treatment, prophylaxis, or prevention of a malignancy or infectious disease in a mammalian or human subject in need thereof, said composition being a composition comprising virus-like vesicles (VLVs) produced by a high-titer hybrid virus vector for treatment, prophylaxis, or prevention of malignancy or infectious disease comprising the following operably linked sequence elements:

a) a first DNA sequence comprising a DNA promoter sequence, b) a second DNA sequence encoding alphavirus non-structural protein polynucleotide sequences, c) a third DNA sequence encoding an alphavirus subgenomic RNA promoter, d) a fourth DNA sequence comprising at least one sequence domain each independently selected from the group consisting of a sequence domain encoding a cytokine agonist polypeptide a sequence domain encoding a cytokine antagonist polypeptide a sequence domain encoding a short hairpin RNA (shRNA), and combinations thereof.

BRIEF DESCRIPTION OF THE DRAWINGS

FIG. 2. Comparison of VLV infection of a cancer cell line (L929 murine fibrosarcoma cells) or "normal" (i.e., non-cancerous) murine fibroblast cell line (NIH 3T3) shows selective death of infected cancer cells.

FIG. 5. VLV-IL-12 inoculated into tumor-bearing mice results in limitation of tumor volume. MC38 cells transplanted subcutaneously into a syngeneic mouse strain allow tumors to grow under the skin of the mice. Inoculation of tumor-bearing mice with VLV-IL-12 limits the growth of the tumors while mice inoculated with PBS (control) produce large tumors of the expected size. The sequence schematic of the VLV with IL-12 transgene is depicted in FIG. 4A. FIG. 5A shows a schematic of the experimental design and timeline. FIG. 5B is a graphic representation of tumor volume over time of the experiment. Asterisks denote statistical significance (P<0.05).

FIG. 6. VLVs can express IL-17RA in vitro.

FIG. 7. VLVs can produce shRNAs that reduce the expression of PD-L1 in transfected cells.

FIG. 8. Trivalent VLVs comprising CARG-2020 produce the encoded transgene polypeptides and shRNAs.

FIG. 9. The trivalent VLV is effective in suppressing tumor volume.

FIG. 10. Mice harboring MC38 tumors were treated with intratumoral injection of indicated VLVs at days 14 and 16 post tumor cell injection.

DETAILED DESCRIPTION OF THE INVENTION

The present invention relates to the unexpected discovery that virus-like vesicles (VLVs) can be armed with one or multiple sequences encoding cytokine agonists, cytokine antagonists, short hairpin RNAs, and other polynucleotides or polypeptides, each of which being useful for treatment, prophylaxis, and prevention of cancer, malignancy or infection disease. The VLVs of the present invention are produced from high-titer hybrid virus vectors encoding the same. Virus-like vesicles (VLVs) are a capsid-free, self-replicating artificial virus platform carrying positive-strand capped and polyadenylated RNA encoding an alphavirus non-structural protein and a vesiculovirus glycoprotein.

In some aspects, the VLVs of the present invention useful for treatment, prophylaxis, and prevention of cancer, malignancy are further complemented by the unexpected discovery that the VLVs are oncolytic. Tumor cells, cancer cells, malignant cells, or cells with characteristics of malignancy allow VLV replication as a lytic process due to unchecked VLV replication, while VLV replication does not proceed unchecked in normal cells. In some examples of normal cells, VLV replication is restricted by the recognition of dsRNA by pattern recognition receptors and induction of type I interferons, which blocks VLV replication in the normal cells. If type I interferon pathways are impaired, such as in cancer or tumor cells, VLV can proceed unchecked. Thereby, they allow VLV replication proceed as a lytic process: once VLV replication is started it causes host cell protein synthesis shut-off and causes apoptosis. Even if apoptosis pathways are deficient in tumor cells, cells with high burden of VLV are lysed.

Therefore, the VLVs of the present invention can have at least two beneficial effects on tumor cells, cancer cells, and malignancies by their production of one or multiple cytokine agonists, cytokine antagonists, short hairpin RNAs, and other polynucleotides or polypeptides useful for the treatment, prophylaxis, and/or prevention of a malignancy, and by further having oncolytic activity during their self-replication. Said cytokine agonists, cytokine antagonists, short hairpin RNAs, and other polynucleotides or polypeptides useful for the treatment, prophylaxis, and/or prevention of a malignancy or infection disease which are produced in a host cell as replication or translation products the RNA of the VLV may be referred to as "therapeutic agents".

Figure 1A:
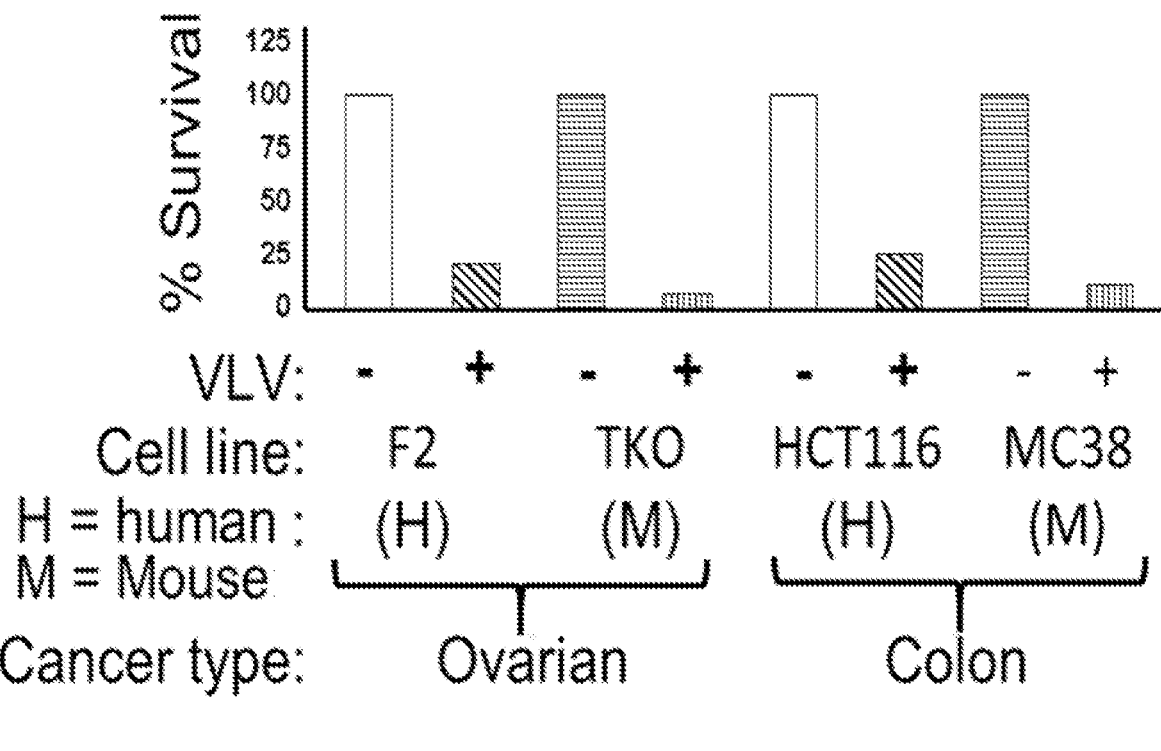
FIG. 1. Infection with VLV of various chemotherapy-resistant cancer lines (derived from mouse or humans) causes death of >70% of the cells (FIG. 1A).
FIG. 1B shows the oncolytic action of VLVs for several types of acute lymphoblastic leukemia type B (B-ALL) cancer cell lines of MN60, REH and RS4,11. The VLVs kill the different stages of these leukemia cells with different efficacy, as the data shows VLVs have higher oncolytic activity against more malignant and less differentiated cells.
FIG. 1C is a representation of regular B cells and the different cancer cell lines labeled with the differentiating markers expressed by each.
Figure 1B:
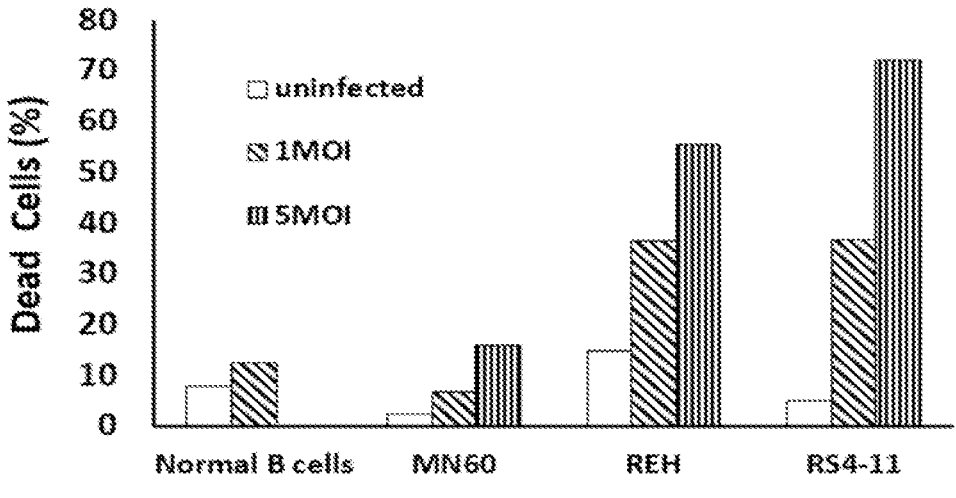
Figure 1C:
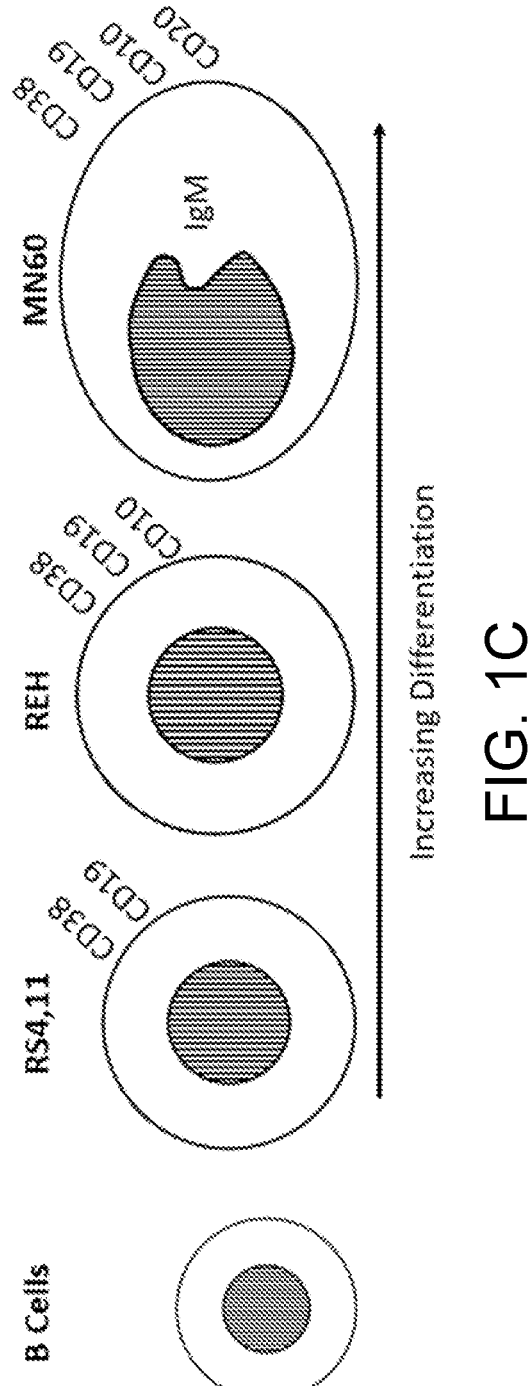
Figure 2A:
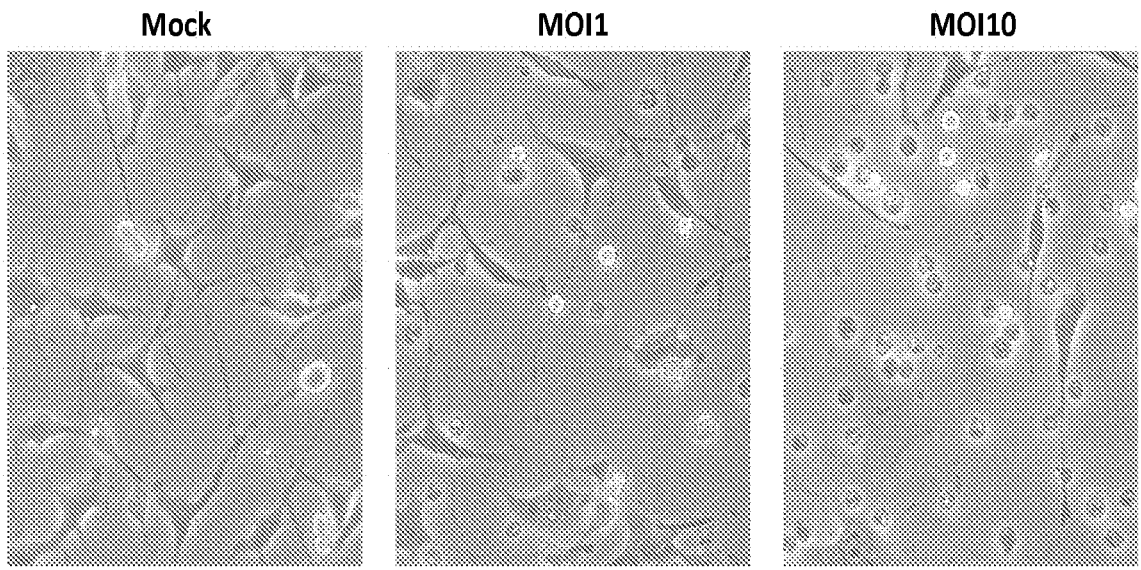
FIG. 2A shows photomicrographs of L929 cancer cells after 24 hr with or without VLV at multiplicities of infection (MOI) 1 and 10.
Figure 2B:
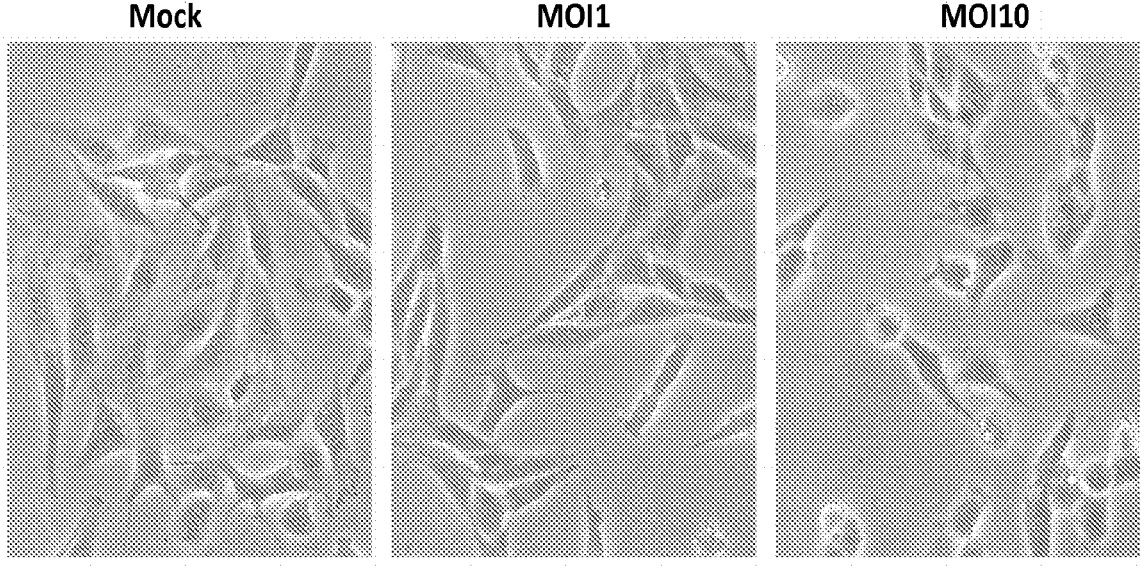
FIG. 2B shows photomicrographs of normal 3T3 cell line after 24 hr without and with VLV at MOI 1 and 10.
Figure 2C:
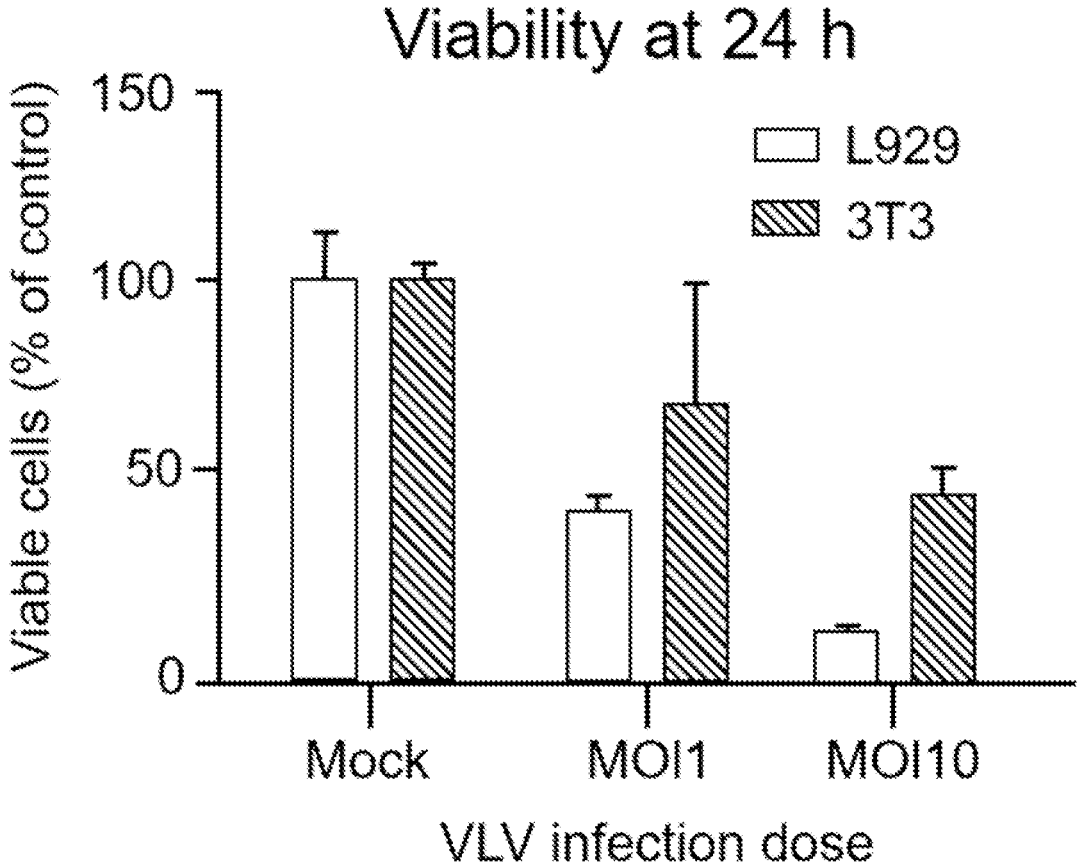
FIG. 2C shows a graphic representation of the photomicrograph data in A and B.
Figure 3:
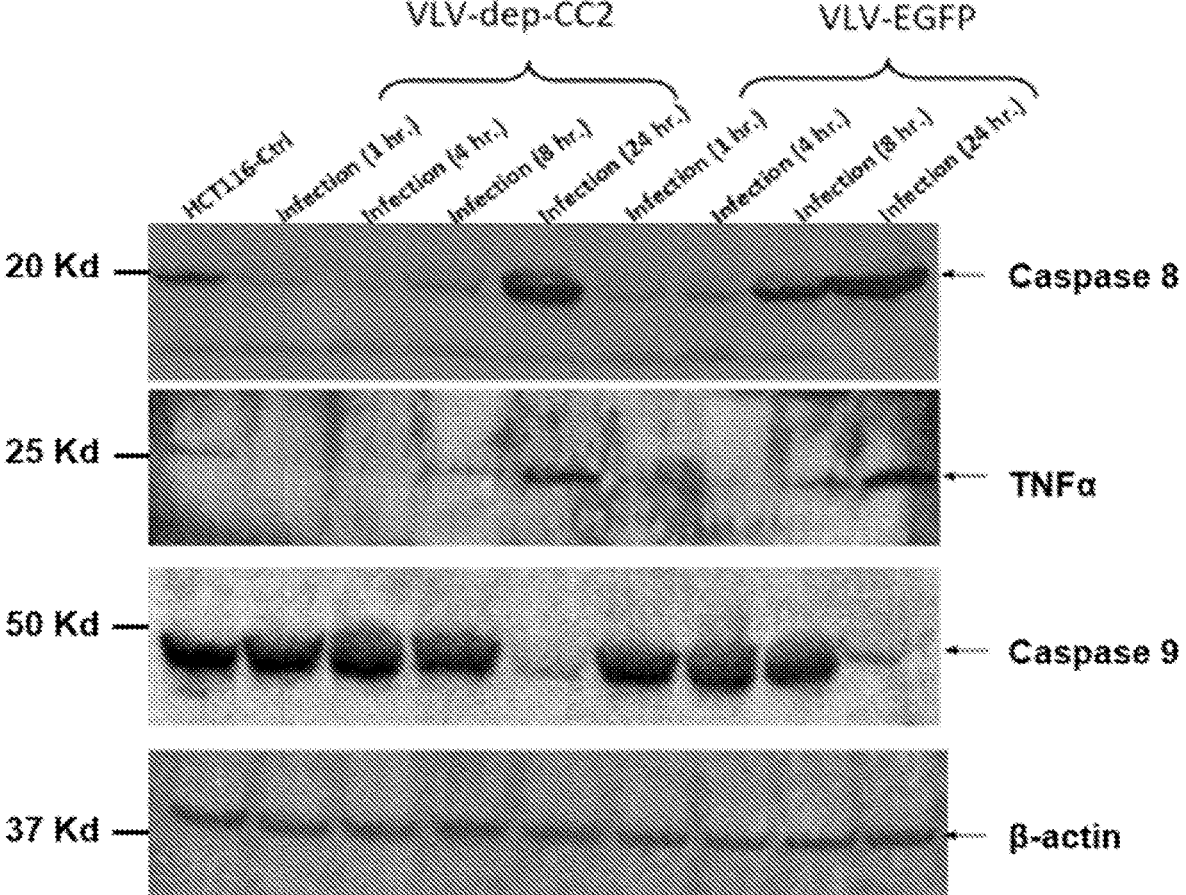
FIG. 3. VLVs cause cell death of cancer cells by apoptosis. Proteins within the apoptosis cascade were detected in western blot with antibodies for the indicated proteins.

In one embodiment of this invention, the VLVs are competent for oncolysis of several types of cancer cells in 65 vitro (FIG. 1A-C) including colon cancer, ovarian cancer and acute lymphoblastic leukemia, but are poorly infectious in normal mammalian cells (FIG. 2). The acute lymphoblastic leukemia type B (B-ALL) cancer cell lines MN60, REH and RS4,11 are characterized by their expression of differentiating markers as shown in FIG. 1C. RS4,11 is a relatively small cell with regular shape, finely dispersed chromatin, and one or more nucleoli. RS4,11 expresses CD38 and CD19. REH is a small/medium sized cell with a regular or indented shape, finely dispersed and/or coarsely condensed chromatin, and one or more nucleoli. REH expresses CD38, CD19, and CD10. MN60 is a relatively medium/large cell with an irregular and/or lobulated shaped, finely stipped and/or homogeneous chromatin, and has prominent, two or more nuclei. MN60 expresses CD38, CD19, CD10, CD20, and IgM. Infection of a cancer cell line with VLVs induced the activation of caspase 8 and caspase 9, expression of tumor necrosis factor (TNF), and cleavage of poly(ADP) ribose polymerase (PARP indicating that oncolysis of cancer cells occurs through apoptotic mechanisms (FIG. 3).

Figure 4A:
FIG. 4A shows a sequence schematic of the VLV with IL-12 transgene (DP-G(NJ)-IL12) comprising a DNA promoter (PRO), a sequence encoding a Semliki Forest Virus non-structural protein (SFV nsp1-4), a sequence encoding a subgenomic promoter (SGP), a sequence encoding a vesicular stomatitis virus glycoprotein (VSV-G), a sequence encoding a SGP, and a sequence encoding IL-12.
Figure 4B:
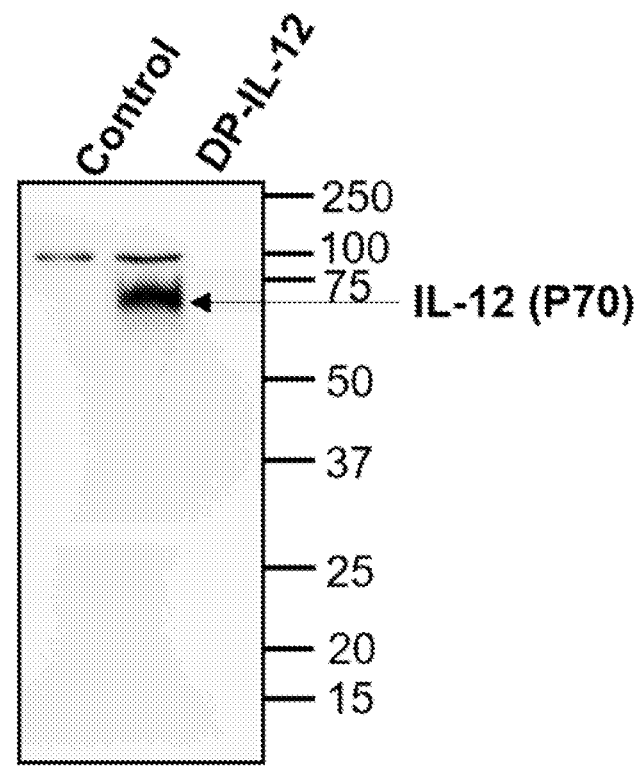
FIG. 4. VLVs can express IL-12 in vitro.
FIG. 4C shows an anti-IL-12 antibody western blot of cell supernatant from VLV-IL-12 infected BHK21 cells compared to uninfected cells demonstrating that the IL-12 expressed from VLV-IL-12 is secreted and soluble.

In another embodiment of this invention, VLVs can be armed with IL-12, a cytokine that has anticancer activities. When armed with IL-12, VLV can infect MC38 mouse colon cancer cell line and baby hamster kidney (BHK21) cells, and express secreted IL-12 protein in vitro (FIG. 4). When the IL-12-armed VLV was used to treat MC38-tumor bearing mice, tumor volumes were significantly reduced compared to mice treated with phosphate-buffered saline as control (FIG. 5).

Figure 6A:
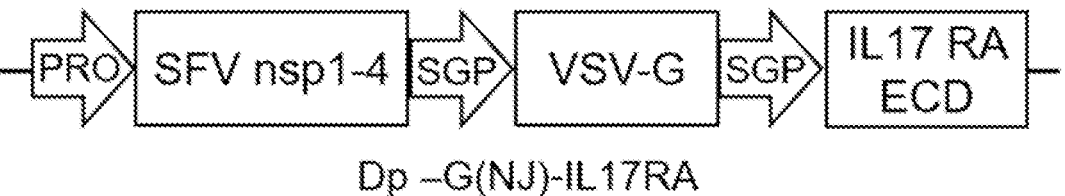
FIG. 6A shows a schematic of the VLV with IL-17RA transgene (DP-G(NJ)-IL17RA) that express IL-17RA extracellular domain (ECD) in BHK21 cells.
Figure 6B:
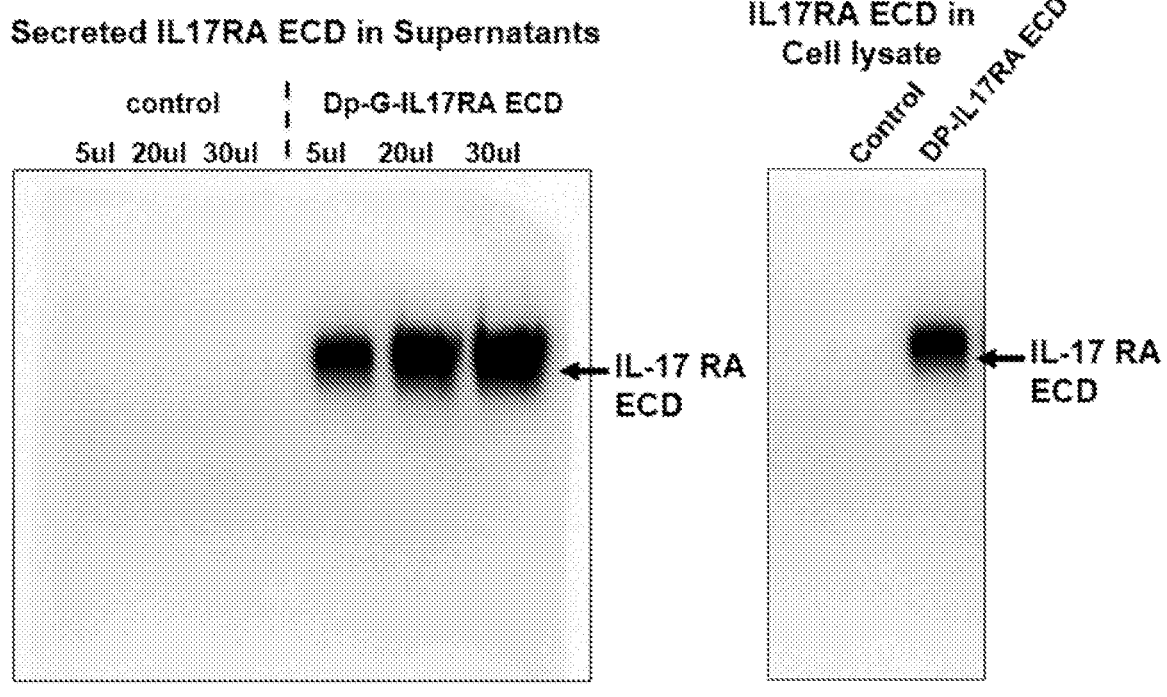
FIG. 6B shows that IL-17RA can be expressed in vitro as detected by anti-IL-17 Western blotting.

In yet another embodiment, VLVs can be armed with a dominant-negative (DN) mutant of IL-17A-receptor (IL-17RA) (FIG. 6). IL-17 promotes tumor growth and inhibits anti-cancer immunity. Therefore, VLV interfering with IL-17 signaling via expression of IL-17RA-DN, should exhibit enhanced oncovirus activity.

Figure 7A:
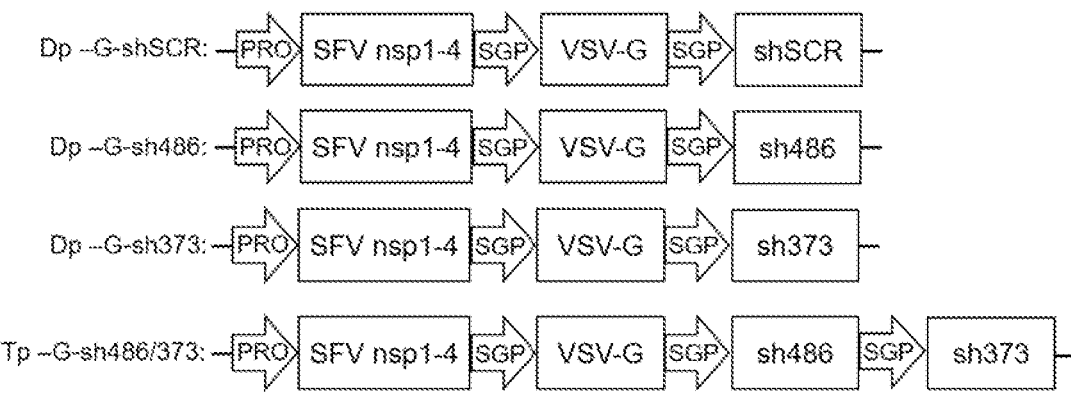
FIG. 7A shows a schematic diagram of four different constructs of VLV-PD-L1shRNA.
Figure 7B:
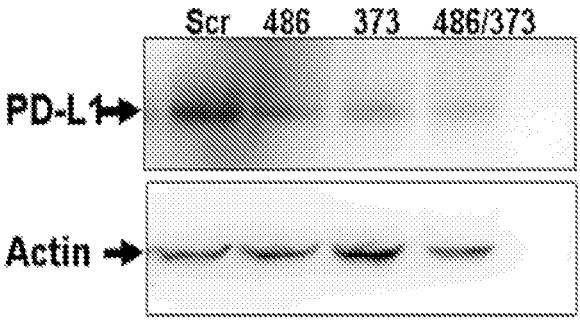
FIG. 7B) shows the anti-PD-L1 Western blotting of lysates from PD-L1 transfected cells.
Figure 7C:
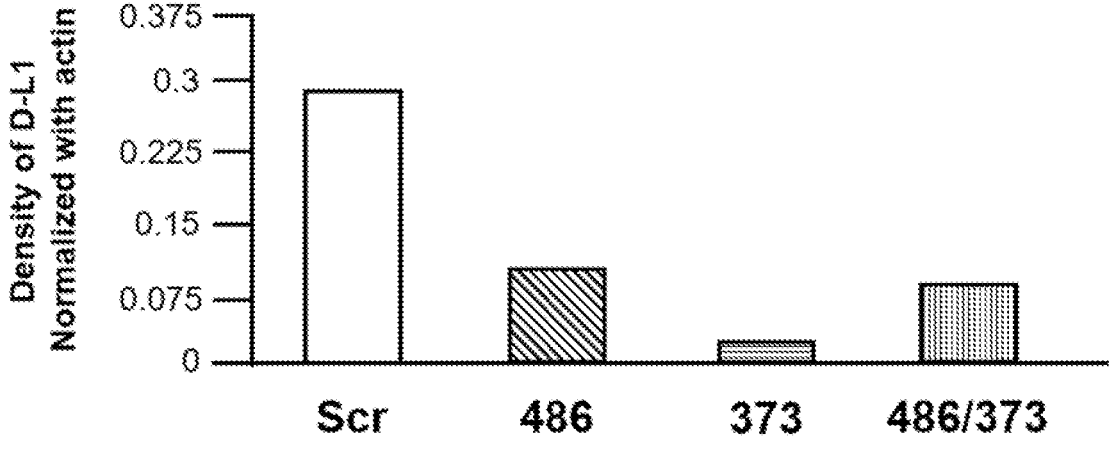
FIG. 7C shows a graphic representation of the Western blot data in FIG. 7B.

In another embodiment, VLV can be armed with shRNAs against PD-L1, the ligand for Programmed-Death-1 receptor, an immune check point protein that attenuates the activity of CD8+ T cells when ligand and receptor expressed on separate cells interact. When PD-L1 expressing BHK21 cells are infected with VLVs encoding PD-L1-shRNA, the expression of PD-L1 is suppressed by the shRNA in a specific manner (no suppression by a scrambled version (SCR) of the shRNA) (FIG. 7). VLVs expressing this shRNA can be expected to have enhanced oncolytic activity since CD8 T cells that are recruited to the tumor would not be attenuated due to the absence of PD-L1.

Figures 8A, 8B:
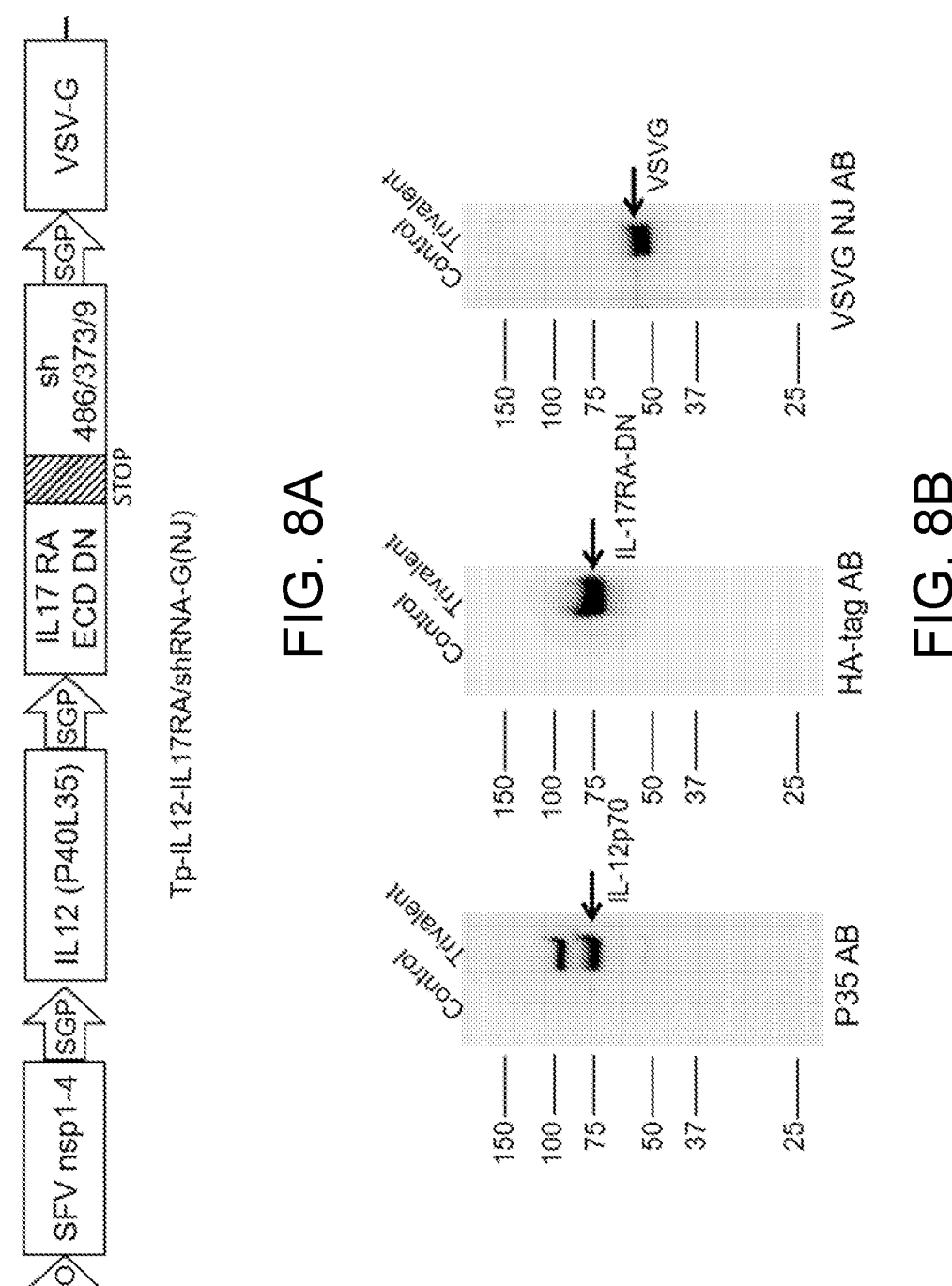
FIG. 8A shows a schematic of the trivalent VLV (i.e. CARG-2020) that can express three components: IL-12, IL-17RA-DN, and PD-L1shRNA. Use of multiple subgenomic promoters (SGP) in this context is novel.
FIG. 8B shows Western blots that demonstrate the expression of each of the IL-12, IL-17RA-DN, and VSV-G polypeptides after infection of BHK-21 cells.
Figure 8C:
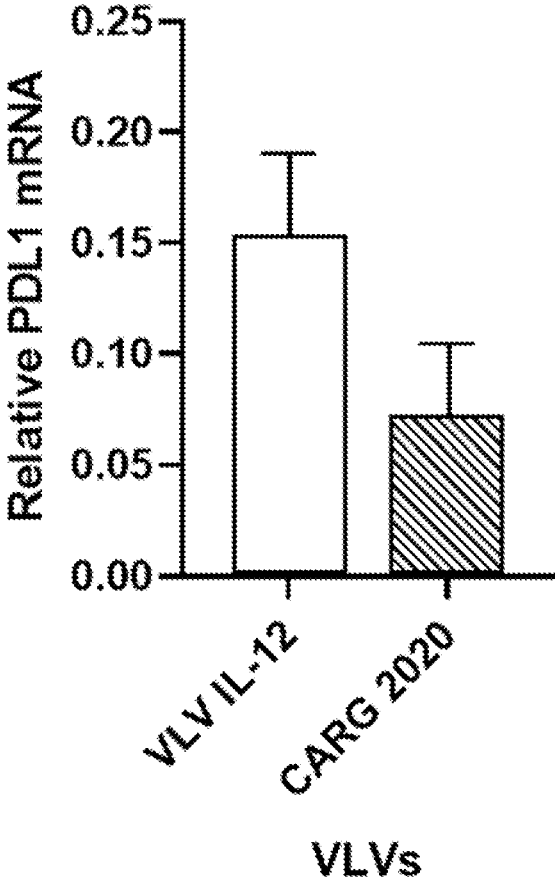
FIG. 8C shows an in vivo comparison of relative PDL1 mRNA detected in the MC38 syngeneic CRC mouse model for animals treated with VLV-IL-12, which lack sequences encoding PDL1 shRNAs, compared to trivalent VLVs (CARG-2020) which comprise sequences encoding PDL1 shRNAs. PDL1 downregulation with CARG-2020 indicates production and function of the shRNAs.
Figure 9A:
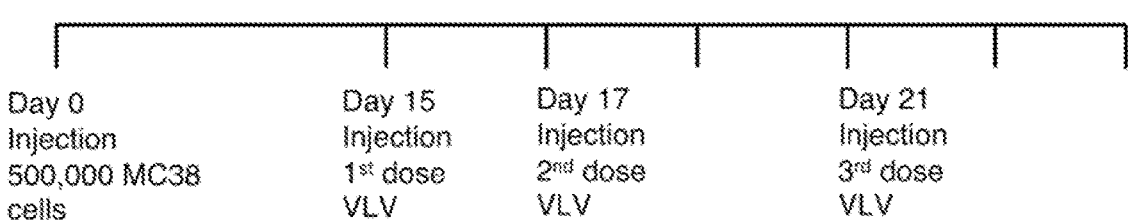
FIG. 9A shows a schematic of the experimental design and timeline. MC38 tumors were grafted to the flank of mouse skin. VLVs carrying GFP, IL-12 or CARG2020 were intratumorally injected at indicated intervals at $5 \times 10^7$ particles per injection.
Figure 9B:
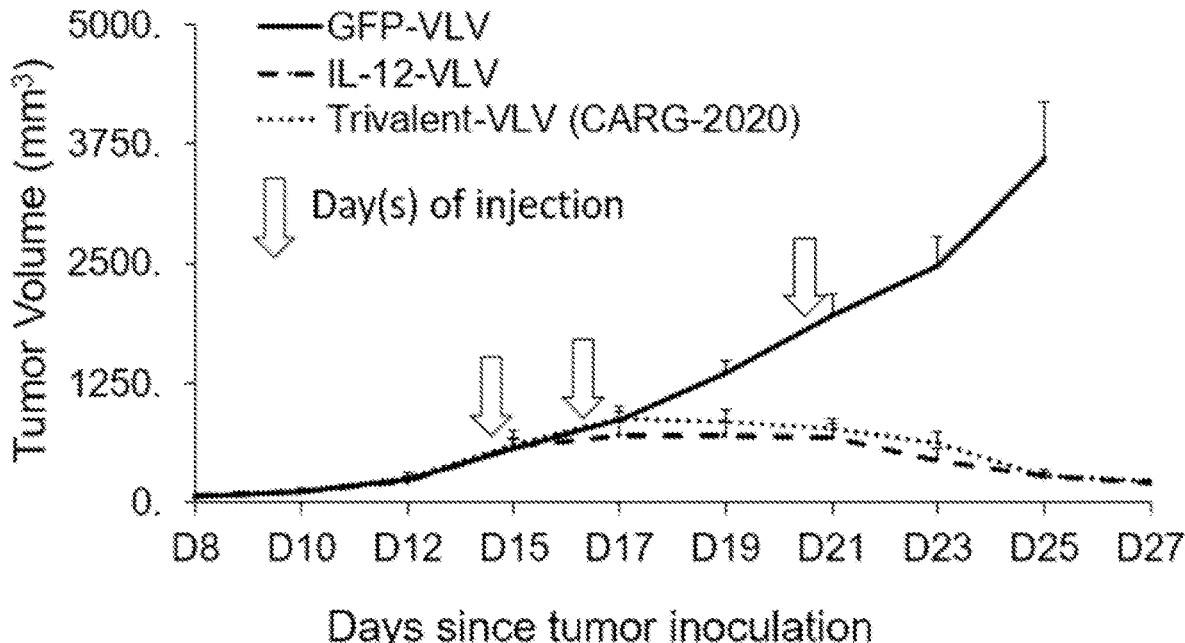
FIG. 9B shows the tumor volume as a function of days since tumor inoculation. Tumor volumes were calculated based on caliber measurements.
Figure 9C:
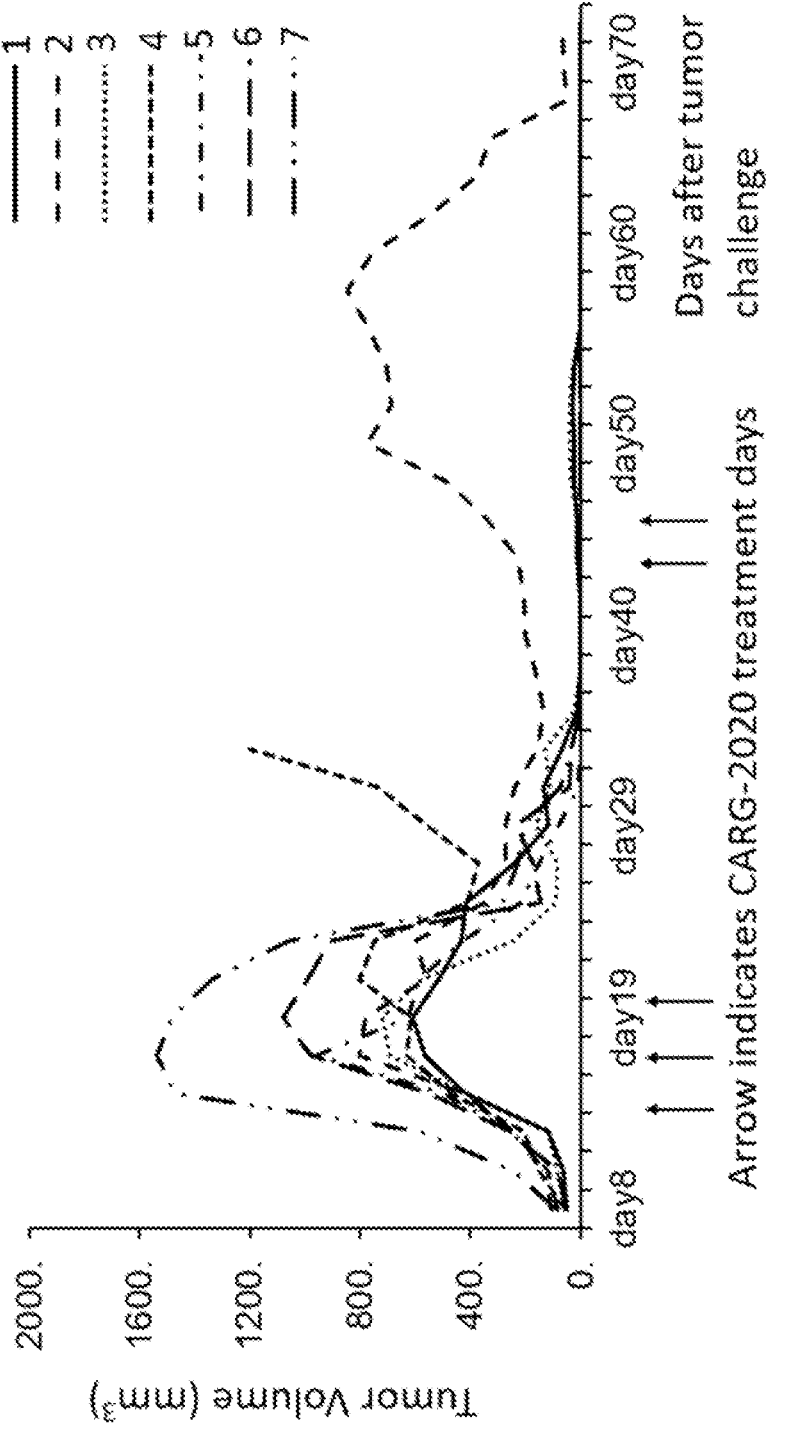
FIG. 9C shows that CARG-2020 treatment in mice resulted in 5 out of 7 treated mice achieved complete tumor eradication under prolonged treatment and monitoring.

In another embodiment, trivalent VLVs can be made that express IL-12, IL-17RA-DN, and PD-L1-shRNA (CARG2020) (FIG. 8). Due to synergies between these three transgene elements, CARG2020 shows greatly enhanced anti-tumor activity (FIG. 9). Treatment with IL-12-VLV and CARG2020 both induces enhanced Th1 and CD8+ T cell recruitment to the tumors, as well as increased their level of activity (FIG. 9). Treatment with IL-12-VLV and CARG2020 also reduced the numbers of regulatory T cells in tumors (FIG. 10). CARG2020 also specifically inhibited the expression of PD-L1 and IL-17 target genes CXCL1 and CXCL2 (FIG. 10).

Figure 11:
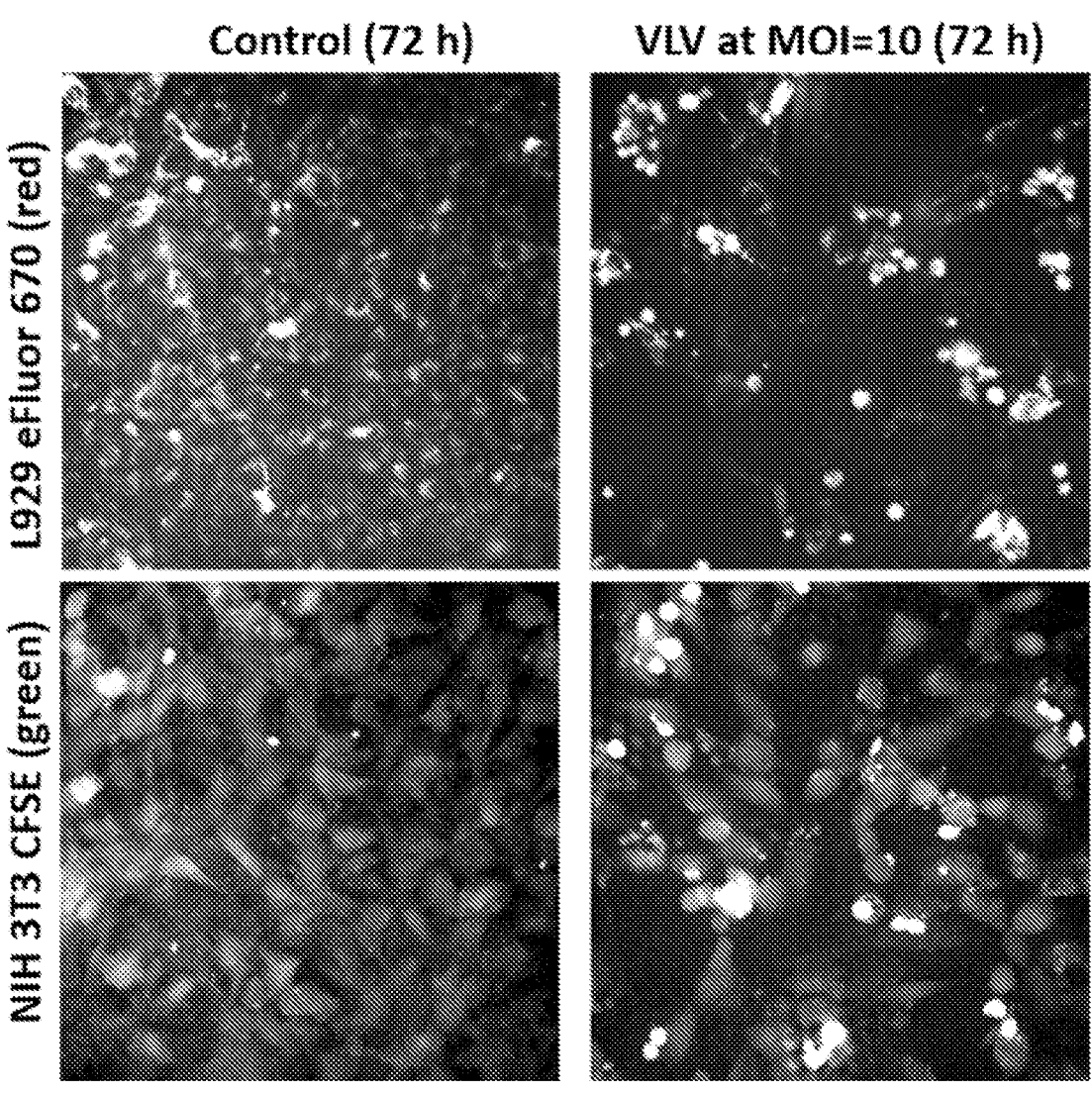
FIG. 11. Oncolytic effects of VLVs on NIH 3T3 vs. L929 cells in co-culture. Normal murine fibroblasts NIH 3T3 were labeled with CFSE dye (green) whereas tumorigenic fibroblasts of line L929 that causes fibrosarcoma were labeled with eFluor670 (red). The cells were co-cultured and either mock treated (control) or treated with VLV at multiplicity of infection (MOI) of 10. Most of the L929 are undergoing apoptosis caused by replication of VLV whereas most of the NIH 3T3 cells are spared. The red and green color channels are separated for greyscale presentation where, in each of the four panels of FIG. 11, a white or shade of white/gray indicates the fluorescence color indicated in the row label on the left of the figure and the black coloration is the background indicating regions where no fluorescence is detected.

In a further embodiment, VLVs are shown to be oncolytic (FIG. 11). Normal murine fibroblasts NIH 3T3 were labeled with CFSE dye (green) whereas tumorigenic fibroblasts of line L929 that causes fibrosarcoma were labeled with eFluor670 (red). It was observed that tumorigenic fibroblasts of line L929 underwent apoptosis due to the oncolytic effect of VLV replication whereas NIH 3T3 did not undergo apoptosis.

Definitions

Unless defined otherwise, all technical and scientific terms used herein have the same meaning as commonly understood by one of ordinary skill in the art to which the invention pertains. In addition to the materials and methods described herein, any methods and materials similar or equivalent to those described herein, or any methods and materials suitable to carry out the scope of the invention, may be used in the practice or testing of the present invention In describing and claiming the present invention, the following terminology will be used. It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein, the terms "control," or "reference" are used interchangeably, and refer to a value that is used as a standard of comparison.

"Vaccination" refers to the process of inoculating a subject with an antigen to elicit an immune response in the subject, that helps to prevent or treat the disease or disorder the antigen is connected with. The term "immunization" is used interchangeably herein with vaccination.

The term "immunogenicity" as used herein, refers to the innate ability of an antigen or organism to elicit an immune response in an animal when the antigen or organism is administered to the animal. Thus, "enhancing the immunogenicity" refers to increasing the ability of an antigen or organism to elicit an immune response in an animal when the antigen or organism is administered to an animal. The increased ability of an antigen or organism to elicit an immune response can be measured by, among other things, a greater number of antibodies that bind to an antigen or organism, a greater diversity of antibodies to an antigen or organism, a greater number of T-cells specific for an antigen or organism, a greater cytotoxic or helper T-cell response to an antigen or organism, a greater expression of cytokines in response to an antigen, and the like.

The term "activation", as used herein, refers to the state of a cell following sufficient cell surface moiety ligation to induce a noticeable biochemical or morphological change. Within the context of T cells, such activation refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physico-chemical process.

The term "activated T cell" means a T cell that is currently undergoing cell division, cytokine production, performance of regulatory or cytolytic effector functions, and/or has recently undergone the process of "activation."

"Humoral immunity" or "humoral immune response" both refer to B-cell mediated immunity and are mediated by highly specific antibodies, produced and secreted by B-lymphocytes (B-cells).

"Prevention" refers to the use of a pharmaceutical compositions for the vaccination against a disorder.

"Adjuvant" refers to a substance that is capable of potentiating the immunogenicity of an antigen. Adjuvants can be one substance or a mixture of substances and function by acting directly on the immune system or by providing a slow release of an antigen. Examples of adjuvants are aluminium salts, polyanions, bacterial glycopeptides and slow release agents as Freund's incomplete.

"Delivery vehicle" refers to a composition that helps to target the antigen to specific cells and to facilitate the effective recognition of an antigen by the immune system. The best-known delivery vehicles are liposomes, virosomes, microparticles including microspheres and nanospheres, polymers, bacterial ghosts, bacterial polysaccharides, attenuated bacterias, virus like particles, attenuated viruses and ISCOMS.

"Incorporated into" or "encapsulated in" refers to an antigenic peptide that is within a delivery vehicle, such as microparticles, bacterial ghosts, attenuated bacteria, virus like particles, attenuated viruses, ISCOMs, liposomes and preferably virosomes.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "fusion protein" as used herein refers to a protein wherein the protein comprises two or more proteins linked together by peptide bonds or other chemical bonds.

The proteins can be linked together directly by a peptide or other chemical bond, or with one or more amino acids between the two or more proteins, referred to herein as a "spacer".

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "RNA" as used herein is defined as ribonucleic acid. The term "dsRNA" is used to define double-stranded RNA.

"Transform", "transforming", and "transformation" is used herein to refer to a process of introducing an isolated nucleic acid into the interior of an organism.

The term "treatment" as used within the context of the present invention is meant to include therapeutic treatment as well as prophylactic, or suppressive measures for the disease or disorder. As used herein, the term "treatment" and associated terms such as "treat" and "treating" means the reduction of the progression, severity and/or duration of a disease condition or at least one symptom thereof. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

The term "biological" or "biological sample" refers to a sample obtained from an organism or from components (e.g., cells) of an organism. The sample may be of any biological tissue or fluid. Frequently the sample will be a "clinical sample" which is a sample derived from a patient. Such samples include, but are not limited to, bone marrow, cardiac tissue, sputum, blood, lymphatic fluid, blood cells (e.g., white cells), tissue or fine needle biopsy samples, urine, peritoneal fluid, and pleural fluid, or cells therefrom. Biological samples may also include sections of tissues such as frozen sections taken for histological purposes.

The term "equivalent," when used in reference to nucleotide sequences, is understood to refer to nucleotide sequences encoding functionally equivalent polypeptides. Equivalent nucleotide sequences will include sequences that differ by one or more nucleotide substitutions, additions- or deletions, such as allelic variants; and will, therefore, include sequences that differ from the nucleotide sequence of the nucleic acids described herein due to the degeneracy of the genetic code.

"Hybridization" refers to any process by which a strand of nucleic acid binds with a complementary strand through base pairing. Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. Hybridization also includes the formation of duplexes which contain certain mismatches, provided that the two strands are still forming a double stranded helix. "Stringent hybridization conditions" refers to hybridization conditions resulting in essentially specific hybridization. The term "specific hybridization" of a probe to a target site of a template nucleic acid refers to hybridization of the probe predominantly to the target, such that the hybridization signal can be clearly interpreted. As further described herein, such conditions resulting in specific hybridization vary depending on the length of the region of homology, the GC content of the region, the melting temperature "Tm" of the hybrid. Hybridization conditions will thus vary in the salt content, acidity, and temperature of the hybridization solution and the washes.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. An "isolated cell" or "isolated population of cells" is a cell or population of cells that is not present in its natural environment.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The term "variant," when used in the context of a polynucleotide sequence, may encompass a polynucleotide sequence related to that of a gene or the coding sequence thereof. This definition may also include, for example, "allelic," "splice," "species," or "polymorphic" variants. The polypeptides generally will have significant amino acid identity relative to each other. A polymorphic variant is a variation in the polynucleotide sequence of a particular gene between individuals of a given species. Polymorphic variants may encompass "single nucleotide polymorphisms" (SNPs) in which the polynucleotide sequence varies by one base. The presence of SNPs may be indicative of, for example, a certain population, a disease state, or a propensity for a disease state.

The term "silent mutation" as used herein refers to a change in the sequence or identity of nucleotide bases which constitute DNA, without a subsequent change in the amino acid sequence of the function of the overall protein.

The term "ameliorating" or "treating" means that the clinical signs and/or the symptoms associated with a disease are lessened as a result of the actions performed. The signs or symptoms to be monitored will be well known to the skilled clinician.

As used herein, by "combination therapy" is meant that a first agent is administered in conjunction with another agent. "In combination with" or "In conjunction with" refers to administration of one treatment modality in addition to another treatment modality. As such, "in combination with" refers to administration of one treatment modality before, during, or after delivery of the other treatment modality to the individual. Such combinations are considered to be part of a single treatment regimen or regime.

"Titers" are numerical measures of the concentration of a virus or viral vector compared to a reference sample, where the concentration is determined either by the activity of the virus, or by measuring the number of viruses in a unit volume of buffer. The titer of viral stocks are determined, e.g., by measuring the infectivity of a solution or solutions (typically serial dilutions) of the viruses, e.g., on HeLa cells using the soft agar method (see, Graham & Van Der eb (1973) Virology 52:456-467) or by monitoring resistance conferred to cells, e.g., G418 resistance encoded by the virus or vector, or by quantitating the viruses by UV spectrophotometry (see, Chardonnet & Dales (1970) Virology 40:462-477). In some embodiments, the titer is provided in units of plaque forming units (pfu) per mL (pfu/mL).

The term "high-titer" as used herein describes a titer of at least about $1 \times 10^7$ pfu/mL in some embodiments, or at least about $5 \times 10^7$ pfu/mL in some embodiments, or at least about $1 \times 10^8$ pfu/mL in some embodiments.

As used herein, the term "pharmaceutical composition" refers to a mixture of at least one compound useful within the invention with other chemical components, such as carriers, stabilizers, diluents, adjuvants, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

The term "antibody" or "Ab" as used herein, refers to a protein, or polypeptide sequence derived from an immunoglobulin molecule which specifically binds to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab).sub.2, as well as single chain antibodies (scFv) and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). An antibody may be derived from natural sources or from recombinant sources. Antibodies are typically tetramers of immunoglobulin molecules.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Heterologous antigens" used herein to refer to an antigen that is not endogenous to the organism comprising or expressing an antigen. As an example, a virus vaccine vector comprising or expressing a viral or tumor antigen comprises a heterologous antigen. The term "Heterologous protein" as used herein refers to a protein that elicits a beneficial immune response in a subject, irrespective of its source.

As defined herein, an "Alphavirus" is a member of the Group IV Togaviridae family of viruses. Alphaviruses include, but are not limited to Aura virus, Babanki virus, Barmah Forest virus, Bebaru virus, Cabassou virus, Chikungunya virus, Eastern equine encephalitis virus, Everglades virus, Fort Morgan virus, Getah virus, Highlands virus, Kyzylagach virus, Mayaro virus, Me Tri virus, Middelburg virus, Mosso das Pedras virus, Mucambo virus, Ndumu virus, O'nyong'nyong virus, Pixuna virus, Rio Negro virus, Ross River virus, Sagiama virus, Salmon pancreas disease virus, Semliki Forest virus, Sindbis virus, Southern elephant seal virus, Tonate virus, Trocara virus, Una virus, Venezuelan equine encephalitis virus, Western equine encephalitis virus and Whataroa virus.

As defined herein, an "alphavirus non-structural protein" can be any of nsp1, nsp2, nsp3 and nsp4, as well as combinations and variants thereof.

As defined herein, an "alphavirus structural protein" can be selected from the group consisting of an alphavirus capsid protein and at least one spike protein.

The term "specifically binds", "selectively binds" or "binding specificity" refers to the ability of the humanized antibodies or binding compounds of the invention to bind to a target epitope present on VSV with a greater affinity than that which results when bound to a non-target epitope. In certain embodiments, specific binding refers to binding to a target with an affinity that is at least 10, 50, 100, 250, 500, or 1000 times greater than the affinity for a non-target epitope.

As used herein, the term "effective amount" or "therapeutically effective amount" means the amount of the virus like particle generated from vector of the invention which is required to prevent the particular disease condition, or which reduces the severity of and/or ameliorates the disease condition or at least one symptom thereof or condition associated therewith.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. In the present disclosure, the term "vector" includes an autonomously replicating virus.

The terms "2A" or "2A peptide" is a self-processing viral peptide. The 2A peptide can separate different protein coding sequences in a single ORF transcription unit (Ryan et al., 1991, J Gen Virol 72:2727-2732). Initially, the 2A peptide cleavage was thought to be mediated by an autoproteolytic event and 2A peptides were called "self-cleaving peptides." Ultimately, a ribosomal-skip mechanism was proposed, and 2A and 2A-like sequences are now referred to as CHYSELs (cis-acting hydrolase elements) rather than self-cleaving peptides (Donnelly et al., 2001, J Gen Virol 82:1013-1025) Linking proteins with 2A or 2A-like peptide sequences results in cellular expression of multiple, discrete proteins (in essentially equimolar quantities) derived from a single ORF (de Felipe et al., 2006, Trends Biotechnol 24:68-75).

As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. There are numerous expression control sequences, including promoters which are native, constitutive, inducible and/or tissue-specific, are known in the art that may be used in the compositions of the invention. "Operably linked" should be construed to include RNA expression and control sequences in addition to DNA expression and control sequences. "Operably linked" should further not be construed to define any specific ordering of sequence elements that are defined to be operably linked in order to form a recited construct, such as a vector, and it can be appreciated that operably linked sequence elements can be assembled in any order such that the construct comprising operably linked sequences is useful, even if crudely, for its intended purpose.

"Oncolytic" as used herein refers to the property of a virus or VLV to infect and kill cancer cells via an apoptotic mechanism. Likewise, "oncolytic effect" refers to the property of a virus or VLV to induce oncolysis A "subject" or "patient", as used herein, may be a human or non-human mammal. Non-human mammals include, for example, livestock and pets, such as ovine, bovine, porcine, canine, feline and murine mammals. In some embodiments, the subject is human.

"Vesiculovirus glycoprotein" as used herein is any suitable vesiculovirus glycoprotein that promotes the formation of a virus-like vesicle when incorporated into an SFV replicon encoding SFV non-structural proteins. In some embodiments, the vesiculovirus glycoprotein is a vesicular stomatitis virus (SFV) glycoprotein.

"Malignancy" as used herein refers to the state or presence of cancer or tumors and is intended to refer to any cancerous state. The term "malignancy" is also intended to describe cells that have a propensity to become cancerous or may develop a propensity to become cancerous, or cells that have a characteristic of malignancy. The term "malignancy" is used interchangeably herein with "cancer" and "tumor".

"Therapeutic agent" as used herein refers to any component of or encoded by the RNA of the VLV, such as cytokine agonists, cytokine antagonists, short hairpin RNAs, and other polynucleotides or polypeptides useful for the treatment, prophylaxis, and/or prevention of a malignancy or infectious disease which is produced in a host cell as replication or translation products the RNA of the VLV. In some embodiments, the VLV may comprise or encode more than one or multiple therapeutic agents. In some embodiments where an oncolytic effect alone is desired, a VLV may not encode any therapeutic agents. The high-titer virus vector used to produce the VLV will comprise DNA sequences encoding the therapeutic agents and may comprise subgenomic promoters (SGPs), 2A sequences, or other sequences associated with the DNA sequences encoding the therapeutic agents.

"Armed" as used herein refers to the state of a VLV or high-titer virus vector comprising or encoding one or more therapeutic agents. For example, a "VLV armed with IL-12" would comprise sequence elements encoding IL-12. It can also be appreciated that a given VLV has a corresponding high-titer hybrid virus vector that encodes it, and it is therefore appropriate to refer to a "high-titer virus vector armed with IL-12" or a "vector armed with IL-12" to the same end.

"Percent Identity" is a term used to describe sequence relationships between two or more polynucleotides of polypeptides. In some cases, a sequence of given sequence (e.g. see Sequence Listing) is termed the "reference sequence" to which the contemplated variant sequence is compared. In general, the comparison is made along the length of the reference sequence after a optimal alignment of the reference sequence and the contemplated variant. Computer-implemented algorithms such as those utilized by the BLAST family of programs may be used to produce an optimal alignment for comparison purposes. Any of the sequences disclosed in the present invention can have about 70%, 75%, 80%, 85%, 90%, 95%, 97%, 98%, or 99% identity or homology to the reference sequence.

Description

Compositions

The high-titer hybrid virus vectors of the present invention comprise five operably linked sequence elements: a first DNA sequence comprising a DNA promoter sequence; a second DNA sequence encoding alphavirus non-structural protein polynucleotide sequences; a third DNA sequence encoding an alphavirus subgenomic RNA promoter; a fourth DNA sequence comprising at least one sequence domain each independently selected from the group consisting of a sequence domain encoding a cytokine agonist polypeptide a sequence domain encoding a cytokine antagonist polypeptide a sequence domain encoding a short hairpin RNA (shRNA), and combinations thereof; and a fifth DNA sequence encoding a vesiculovirus glycoprotein. When the vector is propagated in cell culture, high titers of virus like vesicles (VLVs) are obtained, for example, titers of at least $1 \times 10^7$ plaque forming units (pfu) per ml are obtained.

Methods of making the high-titer hybrid-virus vector of the invention are described in detail in the Experimental Examples Section herein.

In one aspect the alphavirus is Semliki Forest virus (SFV). In another aspect the subgenomic RNA promoter is an Semliki Forest virus (SFV) promoter. In another aspect, the alphavirus non-structural protein comprises an RNA-dependent RNA replicase. In another aspect, the Semliki Forest virus (SFV) non-structural protein comprises a SFV RNA-dependent RNA replicase.

In one aspect, the VSV encoding the VSV G protein can be from any VSV serotype known in the art. Non-limiting examples of VSV serotypes include the Indiana (IND-VSV) serotype and New Jersey (NJ-VSV) serotype. In an embodiment, the NJ-VSV serotype glycoprotein is defined by a DNA sequence comprising SEQ ID NO. 11 and a polypeptide sequence comprising SEQ ID NO. 12. In another embodiment, the NJ-VSV serotype glycoprotein is defined by a DNA sequence or polypeptide sequence comprising a sequence having at least about 70%, 75%, 80%, 85%, 90%, 95%, 97%, 98%, or 99% identity or homology to SEQ ID NOs. 11 or 12.

In one aspect, although the cytomegalovirus immediate early promoter is exemplified herein, the invention should not be construed to be limited to this promoter sequence. Promoter sequences that are useful in the invention include any promoter that induces high levels of gene expression. Such promoters may include, but are not limited to those disclosed elsewhere herein.

In a further aspect of the composition of the invention comprises DNA encoding a heterologous protein inserted between the subgenomic alphavirus promoter and DNA encoding the VSV G protein wherein the DNA encoding the heterologous protein is operably linked to DNA encoding a T2A peptide from *Thosea asigna* virus (Szymczak et al., 2004. Nature Biotechnology 22:589-594) which is in turn operably linked to DNA encoding the VSV G protein. In this way, expression of the heterogeneous protein in the resulting VLVs of the invention is effectively tied to expression of the VSV G protein, the latter being essential for replication of the vector. Thus, expression of the heterologous protein is stabilized and the continued presence of the gene expressing this protein in the hybrid vector is assured.

In some embodiments, the 2A peptide is selected from the group consisting of equine rhinitis A virus (E2A), foot-and-mouth disease virus (F2A), porcine teschovirus-1 (P2A), *Thosea asigna* virus (T2A) and any 2A peptide or fragment thereof known in the art. In further embodiments, the 2A peptide is a T2A peptide or any T2A fragment thereof known in the art.

In some embodiments, the heterologous gene can be under the control of an RNA virus promoter sequence that may not necessarily be an alphavirus subgenomic promoter sequence. Such modifications and variations of the RNA promoter sequence driving expression of the heterologous promoter sequences will become apparent to those skilled in the art as they practice the invention. The vector may also include conventional control elements which are operably linked to the heterologous gene in a manner which permits its transcription, translation and/or expression in a cell infected with the hybrid-virus vector produced by the invention.

Elements Encoded by Vectors

The high-titer hybrid virus vectors comprise, among other elements, a DNA sequence comprising at least one sequence domain each independently selected from the group consisting of a sequence domain encoding a cytokine agonist polypeptide a sequence domain encoding a cytokine antagonist polypeptide a sequence domain encoding a short hairpin RNA (shRNA), and combinations thereof. The VLV produced therefrom comprises RNA containing, in the case of an shRNA, or encoding, in the case of a polypeptide, the elements that have a therapeutic effect when delivered to or are produced within a target cell. Such elements are termed "therapeutic agents" and are useful in the treatment, prophylaxis, and prevention of malignancy or infectious disease. In some embodiments, the therapeutic agent is a heterologous protein.

An important aspect of the present invention is that a given high-titer hybrid virus vector may encode several different therapeutic agents. In some aspects, multiple polypeptide therapeutic agents can be encoded by a given high-titer hybrid virus vector. In some aspects, multiple polynucleotide or shRNA therapeutic agents can be encoded by a given high-titer hybrid virus vector. In further aspects, a given high-titer hybrid virus vector can encode one or more polypeptide therapeutic agents and one or more polynucleotide or shRNA therapeutic agents.

A VLV or composition comprising VLVs produced from the high-titer hybrid virus vector comprises dsRNA that includes certain therapeutic agents, such as shRNAs, or encodes polypeptide therapeutic agents. In some embodiments, the VLV or composition comprising VLVs includes or encodes a single therapeutic agents. In some embodiments, the VLV or composition comprising VLVs includes or encodes multiple therapeutic agents. In some embodiments, the VLV or composition comprising VLVs includes or encodes from 1-10 therapeutic agents, or from 1-7 therapeutic agents, or from 1-5 therapeutic agents, or from 1-3 therapeutic agents. In some embodiments, the VLV or composition comprising VLVs is trivalent, meaning that three therapeutic agents are included or encoded.

It can be understood that any therapeutic agent useful for the treatment, prophylaxis, and prevention of a malignancy and/or infectious disease could be incorporated into the high-titer hybrid virus vectors and VLVs of the present invention. In some embodiments, the therapeutic agents are associated with a malignancy or cancer. In some embodiments, the therapeutic agents are cytokine agonist or antagonist polypeptides. In some embodiments, the therapeutic agents are shRNA polynucleotide checkpoint inhibitors.

The encoded cytokine agonist or antagonist polypeptide therapeutic agents may be any such polypeptide that is useful for, or plays a role in, the treatment, prophylaxis, and/or prevention of a malignancy or cancer. In some embodiments, the encoded cytokine agonist or antagonist polypeptides can be any of IL-2, IL-7, IL-15, IL-18, IL-19, IL-35, IL-21, GM-CSF, IL-17, Flt3L, or combinations thereof.

In some embodiments, the shRNA polynucleotide check-point inhibitors can be a polynucleotide selected from any of PD-L2, PD-L1, CTLA-4, LAG-3, TIM-3, TIGIT, CD90, BTLA, CD160, PD-1, or combinations thereof. In further embodiments, the shRNA polynucleotide checkpoint inhibitors can be any such polynucleotide that is useful for, or plays a role in, the treatment, prophylaxis, and/or prevention of a malignancy or cancer.

Table 1 provides descriptions for exemplary sequences of the present invention. In some aspects, a therapeutic agent polynucleotide or polypeptide sequence comprises a sequence having at least about 70%, 75%, 80%, 85%, 90%, 95%, 97%, 98% or 99% identity or homology to any of the reference sequence described herein (see, e.g., Sequence Listing). Typically, a contemplated variant will maintain at least a portion of the biological activity of the reference sequence.

In some embodiments, the high-titer hybrid virus vector is trivalent and encodes IL-12, IL-17RA-DN, and PD-L1 shRNA. In another embodiment, the high-titer hybrid virus vector comprises a sequence domain having at least about 70% sequence identity with SEQ ID NO. 6, a sequence domain having at least about 70% sequence identity with SEQ ID NO. 8, and a sequence domain having at least about 70% sequence identity with SEQ ID NO 10.

TABLE 1

Description of SEQ ID NOs.

| SEQ ID NO. | Sequence Type | Sequence |
|---|---|---|
| 1 | Mouse IL-12 DNA Sequence | ATGTGTCCTC AGAAGCTAAC CATCTCCTGG TTTGCCATCG TTTTGCTGGT GTCTCCACTC ATGGCCATGT GGGAGCTGGA GAAAGACGTT TATGTTGTAG AGGTGGACTG GACTCCCGAT GCCCCTGGAG AAACAGTGAA CCTCACCTGT GACACGCCTG AAGAAGATGA CATCACCTGG ACCTCAGACC AGAGACATGG AGTCATAGGC TCTGGAAAGA CCCTGACCAT CACTGTCAAA GAGTTTCTAG ATGCTGGCCA GTACACCTGC CACAAAGGAG GCGAGACTCT GAGCCACTCA CATCTGCTGC TCCACAAGAA GGAAAATGGA ATTTGGTCCA CTGAAATTTT AAAAAATTTC AAAAACAAGA CTTTCCTGAA GTGTGAAGCA CCAAATTACT CCGGACGGTT CACGTGCTCA TGGCTGGTGC AAAGAAACAT GGACTTGAAG TTCAAaATCA AGAGCAGTAG CAGTTCCCCT GACTCTCGGG CAGTGACATG TGGAATGGCG TCTCTGTCTG CAGAGAAGGT CACACTGGAC CAAAGGGACT ATGAGAAGTA TTCAGTGTCC TGCCAGGAGG ATGTCACCTG CCCAACTGCC GAGGAGACCC TGCCCATTGA ACTGGCGTTG GAAGCACGGC AGCAGAATAA ATATGAGAAC TACAGCACCA GCTTCTTCAT CAGGGACATC ATCAAACCAG ACCCGCCCAA GAACTTGCAG ATGAAGCCTT TGAAGAACTC ACAGGTGGAG GTCAGCTGGG AGTACCCTGA CTCCTGGAGC ACTCCCCATT CCTACTTCTC CCTCAAGTTC TTTGTTCGAA TCCAGCGCAA GAAAGAAAAG ATGAAGGAGA CAGAGGAGGG GTGTAACCAG AAAGGTGCGT TCCTCGTAGA GAAGACATCT ACCGAAGTCC AATGCAAAGG CGGGAATGTC TGCGTGCAAG CTCAGGATCG CTATTACAAT TCCTCATGCA GCAAGTGGGC ATGTGTTCCC TGCAGGGTCC GATCCGTTCC TGGAGTAFFF GTCCCAGGTG TGGGCAGGGT CATTCCACTC TCTGGACCTG CCAGGTGTCT TAGCCAGTCC CGAAACCTGC TGAAGACCAC AGATGACATG GTGAAGACGG CCAGAGAAAA ACTGAAACAT TATTCCTGCA CTGCTGAAGA CATCGATCAT GAAGACATCA CACGGGACCA AACCAGCACA TTGAAGACCT GTTTACCACT GGAACTACAC AAGAACGAGA GTTGCCTGGC TACTAGAGAG ACTTCTTCCA CAACAAGAGG GAGCTGCCTG CCCCCACAGA AGACGTCTTT GATGATGACC CTGTGCCTTG GTAGCATCTA TGAGGACTTG AAGATGTACC AGACAGAGTT CCAGGCCATC AACGCAGCAC TTCAGAATCA CAACCATCAG CAGATCATTC TAGACAAGGG CATGCTGGTG GCCATCGATG AGCTGATGCA GTCTCTGAAT CATAATGGCG AGACTCTGCG CCAGAAACCT CCTGTGGGAG AAGCAGACCC TTACAGAGTG AAAATGAAGC TCTGCATCCT GCTTCACGCC TTCAGCACCC GCGTCGTGAC CATCAACAGG GTGATGGGCT ATCTGAGCTC CGCCTAG |
| 2 | Mouse IL-12 Protein Sequence | MCPQKLTISW FAIVLLVSPL MAMWELEKDV YVVEVDWTPD APGETVNLTC DTPEEDDITW TSDQRHGVIG SGKTLTITVK EFLDAGQYTC HKGGETLSHS HLLLHKKENG IWSTEILKNF KNKTFLKCEA PNYSGRFTCS WLVQRNMDLK FNIKSSSSSP DSRAVTCGMA SLSAEKVTLD QRDYEKYSVS CQEDVTCPTA EETLPIELAL EARQQNKYEN YSTSFFIRDI IKPDPPKNLQ MKPLKNSQVE VSWEYPDSWS TPHSYFSLKF FVRIQRKKEK MKETEEGCNQ KGAFLVEKTS TEVQCKGGNV CVQAQDPYYN SSCSKWACVP CRVRSVPGVG VPGVGPVIPV SGPARCLSQS RNLLKTTDDM VKTAPEKLKE YSCTAEDIDH EDITRDQTST LKTCLPLELH KNESCLATRE TSSTTRGSCL PPQKTSLMMT LCLGSIYEDL KMYQTEFQAI NAALQNHNHQ QIILDKGMLV AIDELMQSLN HNGETLPQKP PVGEADPYRV KMKICILLHA FSTRVVTINR VMGYLSSA* |
| 3 | Mouse IL-17RA-DN ECD DNA Sequence | ATGGCGATTC GGCGCTGCTG GCCACGGGTC GTCCCCGGGC CCGCGCTGGG ATGGCTGCTT CTGCTGCTGA ACGTTCTGGC CCCGGGCCGC GCCTCCCCGC GCCTCCTCGA CTTCCCGGCT CCGGTGTGCG CGCAGGAGGG GCTGAGCTGC AGAGTCAAGA ATAGTACTTG TCTGGATGAC AGCTGGATCC ACCCCAAAAA CCTGACCCCG TCTTCCCCAA AAAACATCTA TATCAATCTT AGTGTTTCCT CTACCCAGCA CGGAGAATTA GTCCCTGTGT TGCATGTTGA GTGGACCCTG CAGACAGATG CCAGCATCCT GTACCTCGAG GGTGCAGAGC TGTCCGTCCT GCAGCTGAAC ACCAATGAGC GGCTGTGTGT CAAGTTCCAG TTTCTGTCCA TGCTGCAGCA TCACCGTAAG CGGTGGCGGT TTTCCTTCAG CCACTTTGTG GTAGATCCTG GCCAGGAGTA TGAAGTGACT GTTCACCACC TGCCGAAGCC CATCCCTGAT GGGGACCCAA ACCACAAATC CAAGATCATC TTTGTGCCTG ACTGTGAGGA CAGCAAGATG AAGATGACTA CCTCATGCGT GAGCTCAGGC AGCCTTTGGG ATCCCAACAT CACTGTGGAG ACCTTGGACA CACAGCATCT GCGAGTGGAC TTCACCCTGT GGAATGAATC CACCCCCTAC CAGGTCCTGC TGGAAAGTTT CTCCGACTCA GAGAACCACA GCTGCTTTGA TGTCGTTAAA CAAATATTTG CGCCCAGGCA AGAAGAATTC CATCAGCGAG CTAATGTCAC ATTCACTCTA AGCAAGTTTC ACTGGTGCTG CCATCACCAC GTGCAGGTCC AGCCCTTCTT CAGCAGCTGC CTAAATGACT GTTTGAGACA CGCTGTGACT GTGCCCTGCC CAGTAATCTC AAATACCACA GTTCCCAAGC CAGTTGCAGA CTACATTCCC CTGTGGTACC CTTACGACGT GCCAGATTAC GCTTAG |
| 4 | Mouse IL- | MAIRPCWPRV VPGPALGWLL LLLNVLAPGR ASPPLLDFPA PVCAQEGLSC RVKNSTCLDD |

TABLE 1-continued

<div align="center">Description of SEQ ID NOs.</div>

| SEQ ID NO. | Sequence Type | Sequence |
|---|---|---|
| | 17RA-DN ECD Protein Sequence | SWIHPKNLTP SSPKNIYINL SVSSTQHGEL VPVLHVEWTL QTDASILYLE GAELSVLQLN TNERLCVKFQ FLSMLQHHRK RWRFSFSHFV VDPGQEYEVT VHHLPKPIPD GDPNHKSKII FVPDCEDSKM KMTTSCVSSG SLWDPNITVE TLDTQHLRVD FILWAESTPY QVLLESFSDS ENHSCFDVVK QIFAPRQEEF HQPANVTFTL SKFHWCCHHH VQVQPFFSSC LNDCLRHAVT VPCPVISNTT VPKPVADYIP LWYPYDVPDY A* |
| 5 | Mouse shRNA 486/373/9 DNA Sequence | ACGTTAGCTC GAGAAGAAGG TATATTGCTG TTGACAGTGA GCGACGGACA AACAGTGACC ACCTTAGTGA AGCTTCAGAT GTAAGGTGGT CACTGTTTGT CCGCTGCCTA CTGCCTCGGA CTTCAAGGGG TCAGTCAGAT TTTTTCTCGA GAAGAAGGTA TATTGCTGTT GACAGTGAGC GACGCTGAAA GTCAATGCCC CATAGTGAAG CTTCAGATGT ATGGGGCATT GACTTTCAGC GCTGCCTACT GCCTCGGACT TCAAGGGGTC AGTCAGAATT TTTCTCGAGA AGAAGGTATA TTGCTGTTGA CAGTGAGCGA CGATTTGCTG GCATTATATA TAGTGAAGCT TCAGATGTAT ATATAATGCC AGCAAATCGC TGCCTACTGC CTCGGACTTC AAGGGGTCAG TCAGAATTTT TT |
| 6 | Flurrian IL-12 DNA Sequence | GTGGCCATAT GGGAACTGAA GAAAGATGTT TATGTCGTAG AATTGGATTG GTATCCGGAT GCCCCTGGAG AAATGGTGGT CCTCACCTGT GACACCCCTG AAGAAGATGG TATCACCTGG ACCTTGGACC AGAGCAGTGA GGTCTTAGGC TCTGGCAAAA CCCTGACCAT CCAAGTCAAA GAGTTTGGAG ATGCTGGCCA GTACACCTGT CACAAAGGAG GCGAGGTTCT AAGCCATTCG CTCCTGCTGC TTCACAAAAA GGAAGATGGA ATTTGGTCCA CTGATATTTT AAAGGACCAG AAAGAACCCA AAAATAAGAC CTTTCTAAGA TGCGAGGCCA AGAATTATTC TGGACGTTTC ACCTGCTGGT GGCTGACGAC AATCAGTACT GATTTGACNT TCAGTGTCAA AAGCAGCAGA GGCTCTTCTG ACCCCCAAGG GGTGACGTGC GGAGCTGCTA CACTCTCTGC AGAGAGAGTC AGAGGGGACA ACAAGGAGTA TGAGTACTCA GTGGAGTGCC AGGAGGACAG TGCCTGCCCA GCTGCTGAGG AGAGTCTGCC CATTGAGGTC ATGGTGGATG CCGTTCACAA GCTGAAGTAT GAAAACTACA CCAGCAGCTT CTTCATCAGG GACATCATCA AACCTGACCC ACCGAAGAAC TTGCAGCTGA AGCCATTAAA GAATTCTCGG CAGGTGGAGG TCAGCTGGGA GTACCCTGAC ACCTGGAGTA CTCCACATTC CTACTTCTCC CTGACATTCT GCGTTCAGGT CCAGGGCAAG AGCAAGAGAG AAAAGAAAGA TAGAGTCTTC ACGGACAAGA CCTCAGCCAC GGTCATCTGC CGCAAAAATG CCAGCATTAG CGTGCGGGCC CAGGACCGCT ACTATAGCTC ATCTTGGAGC GAATGGGCAT CTGTGCCCTG aAGTGTTCCT GGAGTAGGGG TACCTGGGGT GGGCGCCAGA AACCTCCCCG TGGCCACTCC AGACCCAGGA ATGTTCCCAT GCCTTCACCA CTCCCAAAAC CTGCTGAGGG CCGTCAGGAA CATGCTCCAG AAGGCCAGAC AAACTCTAGA ATTTTACCCT TGCACTTCTG AAGAGATTGA TCATGAAGAT ATCACAAAAG ATAAAACCAG CACAGTGGAG GCCTGTTTAC CATTGGAATT AACCAAGAAT GAGAGTTGCC TAAATTCCAG AGAGACCTCT TTCATAACTA ATGGGAGTTG CCTGGCCTCC AGAAAGACCT CTTTTATGAT GGCCCTGTGC CTTGAAGATG TTTATGAAGA CTTAGTAGTG TACCAGGTGG AGTTCAAGAC CATGAATGCA AAGCTGCTGA TGGATCCTAA GAGGCAGATC TTTCTAGATC AAAACATGCT GGCAGTTATT GATGAGCTGA TGCAGGCCCT GAATTTCAAC AGTGAGACTG TGCCAGAAAA ATCCTCCCTT GAAGAACCGG ATTTTTATAA AACTAAAATC AAGCTCTGCA TACTTCTTCA TGCTTTCAGA ATTCGGGCAG TGACTATTGA TAGAGTGATG AGCTATCTGA ATGCTTCCTA A |
| 7 | Flurrian IL-12 Protein Sequence | MCHQQLVISW FSLVFLASPL VAIWELKKDV YVVELDWYPD APGEMVVLTC DTPEEDGITW TLDQSSEVLG SGKTLTIQVK EFGDAGQYTC HKGGEVLSHS LLLLHKKEDG IWSTDILKDQ KEPKNKTFLP CEAKNYSGRF TCWWLTTIST DLTFSVKSSP GSSDPQGVTC GAATLSAEPV RGDNKEYEYS VECQEDSACT AAEESLPIEV MVDAVHKLKY ENYTSSFFIR DIIKPDPPKN LQLKPLKNSR QVEVSWEYPD TWSTPHSYFS LTFCVQVQGK SKREKKDRVF TDKTSATVIC RKNASISVRA QDRYYSSSWS ENASVPCSVP GVGVPGVGAT NLPVATPDPG MFPCLHHSQN LLRAVSNMLQ KARQTLEFYP CTSEEIDHED ITKDKTSTVE ACLPLELTKN ESCLNSPETS FITNGSCLAS RKTSFMMALC LSSIYEDLKM YQVEFKTMNA KLLMDPKRQI FIDQNMLAVI DELMQALNFN SETVPQKSSL EEPDFYKTKI KLCILLHAFR IRAVTIDRVM SYLNAS* |
| 8 | Flurrian IL-17RA-DN ECD DNA Sequence | ATGGGGGCCG CACGCAGCCC GCCGTCCGCT GTCCCGGGGC CCCTGCTGGG GCTGCTCCTG CTGCTCCTGG GCGTGCTGGC CCCGGGTGGC GCCTCCCTGC CACTCCTGGA CCACCGGGCG CTGGTCTGCT CCCAGCCGGG GCTAAACTGC ACGGTCAAGA ATAGTACCTG CCTGGATGAC AGCTGGATTC ACCCTCGAAA CCTGACCCCC TCCTCCCaAA AGGACCTGCA GATCCAGCTG CACTTTGCCC ACACCCAACA AGGAGACCTG TTCCCCGTGG CTCACATCGA ATGGACACTG CAGACAGACG CCAGCATCCT GTACCTCGAG GGTGCAGAGT TATCTGTCCT GCAGCTGAAC ACCAATGAAC GTTTGTGCGT CAGGTTTGAG TTTCTGTCCA AACTGAGGCA TCACCACAGG CGGTGGCGTT TTACCTTCAG CCACTTTGTG GTTGACCCTG ACCAGGAATA TGAGGTGACC GTTCACCACC TGCCCAAGCC CATCCCTGAT GGGGACCCAA ACCACCAGTC CAAGAATTTC CTTGTGCCTG ACTGTGAGCA CGCCAGGATG AAGGTAACCA CGCCATGCAT GAGCTCAGGC AGCCTGTGGG ACCCCAACAT CACCGTGGAG ACCCTGGAGG CCCACCAGCT GCGTGTGAGC TTCACCCTGT GGAACGAATC TACCCATTAC CAGATCCTGC TGACCAGTTT TCCGCACATG GAGAACCACA GTTGCTTTGA CGCACATGCAC CACATACCTG CGCCCAGACC AGAAGAGTTC CACCAGCGAT CaAACGTCAC ACTCACTCTA CGCAACCTTA AAGGGTGCTG TCGCCACCAA GTGCAGATCC AGCCCTTCTT CAGCAGCTGC CTCAATGACT GCCTCAGACA CTCCGCGACT GTTTCCTGCC CAGAAATGCC AGACACTCCA GAACCAATTC CGGCTACATG CCCCTGTGG TAG |
| 9 | Flurrian IL-17RA-DN ECD | MGAAPSPPSA VPGPLLGLLL LLLGVLAPGG ASLPLLDHPA LVCSQPGLNC TVKNSTCLDD SWIHPRNLTT SSPKDLQIQL HFAHTQQGDL FPVABIEWTL QTDASILYLE GAELSVLQLN TNERLCVRFE FLSKLRHHHR PWRFTFSHEV VDPDQEYEVT VHHLPKTIPD GDPNHQSKNF |

TABLE 1-continued

Description of SEQ ID NOs.

| SEQ ID NO. | Sequence Type | Sequence |
|---|---|---|
| | Protein Sequence | LVPDCEHARM KVTTPCMSSG SLWDPNITVE TLEAHQLRVS FTLWNESTHY QILLTSFPHM ENHSCFEHMH HIPAPRPEEF HQRSNVTLTL RNLKGCCRHQ VQIQPFFSSC LNDCLTHSAT VSCPEMPDTP EPIPDYMPLW * |
| 10 | Fiurrian shRNIA 1467321/133 8 DNA Sequence | ACGTTAGCTC GAGAAGAAGG TATATTGCTG TTGACAGTGA GCGACGGCAT TTGCTGAACG CATTTAGTGA AGCTTCAGAT GTAAATGCGT TCAGCAAATG CCGCTGCCTA CTGCCTCGGA CTTCAAGGGG TCAGTCAGAT TTTTTCTCGA GAAGAAGGTA TATTGCTGTT GACAGTGAGC GACGGAAGAC CTGAAGGTTC AGTAGTGAAG CTTCAGATGT ACTGAACCTT CAGGTCTTCC GCTGCCTACT GCCTCGGACT TCAAGGGGTC AGTCAGAATT TTTCTCGAGA AGAAGGTATA TTGCTGTTGA CAGTGAGCGA CGTCCTGAGT GGTAAGACCA TAGTGAAGCT TCAGATGTAT GGTCTTACCA CTCAGGACGC TGCCTACTGC CTCGGACTTC AAGGGGTCAG TCAGAATTTT TT |
| 11 | VSVG NJ DNA Sequence | ATGCTGAGCT ACCTGATCTT CGCCCTGGCC GTGTCTCCTA TCCTGGGCAA GATCGAGATC GTGTTCCCTC AGCACACCAC CGGCGACTGG AAAAGAGTGC CCCACGAGTA CAACTACTGC CCCACCAGCG CCGACAAGAA TAGCCACGGA ACACAGACAG GCATCCCCGT GGAACTGACC ATGCCTAAGG GCCTGACAAC CCACCAGGTG GAAGGCTTCA TGTGTCACAG CGCCCTGTGG ATGACCACCT GTGACTTTCG TTGGTACGGC CCCAAGTACA TCACCCACAG CATCCACAAC GAGGAACCCA CCGACTACCA GTGCCTGGAA GCCATCAAGA GCTACAAGGA CGGCGTGTCC TTCAATCCTG GATTCCCACC TCGAGCTGGC GGCTACGGCA CAGTGACAGA TGCCGAGGCT CACATCGTGA CCGTGACACC TCACAGCGTG AAGGTGGACG AGTACACAGG CGAGTGGATC GACaCTCACT TCATCGGCGG CAGATGCAAG GGCaAAATCT GCGAGACAGT GCACAACAGC ACCAAGTGGT TCACCAGCTC CGATGGCGAG AGCGTGTGCA GCCAGCTGTT TACCCTCGTC GGCGGCATCT TCTTCAGCGA CAGCGAAGAG ATCACCAGCA TGGGCCTGCC TGAAACCGGA ATCAGAAGCA ACTACTTCCC CTACATCAGC ACCGAGGGAA TCTGCAAGAT GCCCTTCTGT CGGAAGCAGG GCTACAAGCT GAAGAACGAC CTGTGGTTCC AGATCATGGA CCCCGACCTG GATAAGACCG TGCGGGATCT GCCCCACATC AAGGACTGTG ATCTGAGCAG aAGCATCATC ACCCCTGGCG AGCACGCCAC AGACATCAGC CTGATCAGCA ACGTGGAACG CATCCTGGAC TACGCCCTGT GCCAGAACAC CTGGTCTAAG ATCGAGTCCG GCGAGCCCAT CACACCCGTG GATCTGTCTT ATCTGGGCCC CAAGAATCCT GGCGTGGGCC CTGTGTTCAC CATCATCAAT GGCAGCCTGC ACTACTTCAC CAGCAAGTAC CTGAGAGTGG AACTGGAAAG CCCTGTGATC CCCAGAATGG AAGGCAAGGT GGCCGGCACA AGAATCGTCA GACAGCTGTG GGACCAGTGG TTCCCATTCG GCGAGGTGGA AATCGGCCCT AACGGCGTGC TGAAAACAAA GCAGGGGTAT AAGTTCCCGC TGCACATCAT CGGCACCGGC GAAGTGGACA GCGACATCAA GATGGAACGG GTCGTGAAGC ACTGGGAGCA CCCTCACATT GAGGCCGCTC AGACCTTaCT GAAGAAGGAC GATACAGGCG AGGTGCTGTA CTACGGCGAT ACCGGGGTGT CAAAGAACCC CGTCGAACTG GTGGAAGGAT GGTTTAGCGG ATGGCGGTCT AGCCTGATGG GAGTGCTGGC CGTGATCATC GGCTTCGTGA TCCTGATGTT CCTGATTAAG CTGATCGGGG TGCTGAGCAG CCTGTTCAaA CCCAAGAGAA GGCCCATCTA CAAGAGCGAC GTCGAGATGG CCCACTTCCG GTAG |
| 12 | VSVG NJ Protein Sequence | MLSYLIFALA VSPILGKIEI VFPQHTTGDW KRVPHEYNYC PTSADKNSHG TQTGIPVELT MPKGLTTHQV EGFMCHSALW MTTCDFRWYG PKYITHSIHN EEPTDYQCLE AIKSYKDGVS FNPGFPPOSC GYGTVTDAEA HIVTVTPHSV KVDEYTGEWI DPHFIGGRCK GQICETVHNS TKWFTSSDGE SVCSQLFTLV GGIFFSDSEE ITSMGLPETG IRSNYFPYIS TEGICKMPFC RKQGYKLKND LWFQIMDPDL DKTVRDLPHI KDCDLSSSII TPGEHATDIS LISDVERILD YALCQNTWSK IESGEPITPV DLSYLGPKNP GVGPVFTIIN GSLHYFTSKY LRVELESPVI PRMEGKVAGT RIVPQLWDQW FPFGEVEIGP NGVLKTKQGY KFPLHIIGTG EVDSDIKMER VVKHWEHPHI EAAQTFLKKD DTGEVLYYGD TGVSKNPVEL VEGWFSGWRS SLMGVLAVII GEVILMFLIK LIGVLSSLFR PKRRPTYKSD VEMAHFR* |
| 13 | SFV nsp1-4 Protein Sequence | MAAKVHVDIEADSPPIKSLQKAFPSFEVESLQVTPNDHANARAFSHLATKLIEQETDKDTLILDI GSAPSRPMMSTHKYHCVCPMRSAEDPERLVCYAKKLAAASEKVLDREIAGKITDLQTVMATPDAE SPTFCLHTDVTCRTAAEVAVYQDVYAVHAPTSLYHQAMKGVRTAYWIGFDTTPFMFDALAGAYPT YATNWADEQVLQARNIGLCAASLTEGRLGKLSILRKKQLKPCDTVMFSVGSTLYTESRKLLRSWH LPSVFHLKGKQSFTCRCDTIVSCEGYVVKKITMCPGLYGKTVGYAVTYHAEGFLVCKTTDTVKGE RVSFPVCTYVPSTICDQMTGILATDITPEDAQKLLVGLNQRIVVNGRTQRNTNTMKNYLLPIVAV AFSKWAREYKADLDDEKPLGVRERSLTCCCLWAFKTRKMHTMYKKPDTQTIVKVPSEFNSFVIPS LWSTGLAIPVRSRIKMLLAKKTKRESIPVLDASSARDAEQEEKERLEAELTREALPPLVPTAPAE TGVVDVDVEELEYHAGAGVVETPRSALKVTAQPNGVLLGNYVVLSPQTVLKSSKLAPVHPLAEQV KIITHNGRAGRYQVDGYDGRVLLPCGSAIPVPEFQALSESATMVYNEREFVNRKLYHIAVHGPSL NTDEENYEKVRAERTDAEYVFDVDKKCCVKREEASGLVLVGELTNPPFHEFAYEGLKIRPSAPYK TTVVGVFGVPGSGKSAIIKSLVTKHDLVTSGKKENCQEIVNDVKKHRGLDIQAKTVDSILLNGCR RAVDILYVDEAFACHSGTLLALIALVKPRSKVVLCGDPKQCGFFNMMQLKVNFNHNICTEVCHKS ISRRCTRPVTAIVSTLHYGGKMRTTNPCNKPIIIDTTGQTKPKPGDIVLTCFRGWVKQLQLDYRG HEVMTAAASQGLTRKGVYAVRQKVNENPLYAPASEHVNVLLTRTEDRLVWKTLAGDPWIKVLSNI PQGNFTATLEEWQEEHDKIMKVIEGPAAPVDAFQNKANVCWAKSLVPVLDTAGIRLTAEEWSTII TAFKEDRAYSPVVALNEICTKYYGVDLDSGLFSAPKVSLYYENNHWDNRPGGRMYGFNAATAARL EARHTFLKGQWHTGKQAVIAERKIQPLSVLDNVIPINRRLPHALVTEYKTVKGSRVEWLVNKVRG YHVLLVSEYNLALPRRRVTWLSPLNVTGADRCYDLSLGLPADAGRFDLVFVNIHTEFRIHHYQQC VDHAMKLQMLGGDALRLLKPGGSLLMRAYGYADKISEAVVSSLSRKFSSARVLRPDCVTSNTEVF LLFSNFDNGKRPSTLHQMNTKLSAVYAGEAMHTAGCAPSYRVKRADIATCTEAAVVNAANARGTV GDGVCRAVAKKWPSAFKGEATPVGTIKTVMCGSYPVIHAVAPNFSATTEAEGDRELAAVYRAVAA EVNRLSLSSVAIPLLSTGVFSGGRDRLQQSLNHLFTAMDATDADVTIYCRDKSWEKKIQEAIDTR |

TABLE 1-continued

Description of SEQ ID NOs.

| SEQ ID NO. | Sequence Type | Sequence |
|---|---|---|
| | | TAVELLNDDVELTTDLVRVHPDSSLVGRKGYSTTDGSLYSYFEGTKFNQAAIDMAEILTLWPRLQ<br>EANEQICLYALGETMDNIRSKCPVNDSDSSTPPRTVPCLCRYAMTAERITRLRSHQVKSMVVCSS<br>FPLPKYHVDGVQKVKCEKVLLFDPTVPSVVSPRKYAASTTDHSDRSLRGFDLDWTTDSSSTASDT<br>MSLPSLQSCDIDSIYEPMAPIVVTADVHPEPAGIADLAADVHPEPADHVDLENPIPPPRPKRAAY<br>LASRAAERPVPAPRKPTPAPRTAFRNKLPLTFGDFDEHEVDALASGITFGDFDDVLRLGRAGAYI<br>FSSDTGSGHLQQKSVRQHNLQCAQLDAVEEEKMYPPKLDTEREKLLLLKMQMHPSEANKSRYQSR<br>KVENMKATVVDRLTSGARLYTGADVGRIPTYAVRYPRPVYSPTVIERFSSPDVAIAACNEYLSRN<br>YPTVASYQITDEYDAYLDMVDGSDSCLDRATFCPAKLRCYPKHHAYHQPTVRSAVPSPFQNTLQS<br>VLAAATKRNCNVTQMRELPTMDSAVFNVECFKRYACSGEYWEEYAKQPIRITTENTTTYVTKLKG<br>PKAAALFAKTHNLVPLQEVPMDRFTVDMKRDVKVTPGTKHTEERPKVQVIQAAEPLATAYLCGIH<br>RELVRRLNAVLRPNVHTLFDMSAEDFDAIIASHFHPGDPVLETDIASFDKSQDDSLALTGLMILE<br>DLGVDQYLLDLIEAAFGEISSCHLPTGTRFKFGAMMKSGMFLTLFINTVLNITIASRVLEQRLTD<br>SACAAFIGDDNIVHGVISDKLMAERCASWVNMEVKIIDAVMGEKPPYFCGGFIVFDSVTQTACRV<br>SDPLKRLFKLGKPLTAEDKQDEDRRRALSDEVSKWFRTGLGAELEVALTSRYEVEGCKSILTAMA<br>TLARDIKAFKKLRGPVIHLYGGPRLVR |

The high-titer hybrid virus vectors of the present invention encode, among the other elements, alphavirus nonstructural proteins. The alphavirus nonstructural proteins of the present invention can be any such proteins that are suitable for carrying out the scope and methods of the invention. In some embodiments, the alphavirus nonstructural proteins comprise an RNA-dependent RNA replicase. In other embodiments, the alphavirus nonstructural proteins are Semliki Forest Virus (SFV) non-structural proteins. In some embodiments, the SFV non-structural proteins comprise a SFV RNA-dependent RNA replicase.

In some embodiments of carrying out the invention, the alphavirus nonstructural proteins comprise mutations that enhance the titer of VLVs produced in the methods of the invention. See U.S. Pat. No. 10,435,712 by Rose et al., incorporated by reference herein in its entirety, which relates to compositions and methods for immunization using high-titer hybrid-virus vectors. The high-titer hybrid virus vectors producing evolved VLV compositions therein comprise SFV alphavirus nonstructural proteins with at least two mutations that improve the titer of VLVs produced.

TABLE 2

Mutations to SFV nonstructural proteins.

| Amino Acid Change | Protein Affected |
|---|---|
| G-106-E (AASEKVL) | nsP1 |
| V-351-I (ATDITPE) | nsP1 |
| L-481-S (KRESIPV) | nsP1 |
| I-516-T (LVPTAPA) | nsP1 |
| D-555-G (QPNGVLL) | nsP2 |
| A-1151-T (ALVTEYK) | nsP2 |
| M-1494-T (AIDTRTA) | nsP3 |
| A-1610-T (ERITRLR) | nsP3 |
| N-2015-S (TLQSVLA) | nsP4 |

In some embodiments of carrying out the invention, the alphavirus nonstructural proteins of the present invention are SFV alphavirus nonstructural proteins comprising at least one mutation as described in Table 2. The mutations listed in Table 2 are shown bolded and underlined in SEQ ID NO. 13 in Table 1. In Table 2, the amino acid mutations shown are relative to the wild type sequence. That is, when each of the mutations in Table 2 are present, the SFV nonstructural protein sequence is defined as SEQ ID NO. 13. SEQ ID NO. 13 comprises four SFV nonstructural protein segments, i.e.

nsP1 (amino acids 1-537), nsP2 (amino acids 538-1136), nsP3 (amino acids 1137-1818), and nsP4 (amino acids 1819-2432).

The high-titer hybrid virus vectors of the present invention encoding for mutated alphavirus nonstructural proteins can be prepared with any suitable polynucleotide sequences for producing the desired amino acid sequences. It can be appreciated that the nucleotide sequences utilized to generate the polypeptide sequences of the present invention can potentially or optionally include mutations, including silent mutations, or alternate codons that function to produce the associated amino acid sequence. It would be readily apparent to a skilled practitioner whether or not a given polynucleotide sequence would produce a given polypeptide sequence.

In some embodiments, the high-titer hybrid virus vectors of the present invention comprise a DNA sequence encoding a SFV nonstructural protein with at least about 70%, 75%, 80%, 85%, 90%, 95%, 97%, 98%, or 99% similarity to SEQ ID NO: 13. In further embodiments, the high-titer hybrid virus vectors of the present invention comprise a DNA sequence encoding a SFV nonstructural protein comprising SEQ ID NO: 13.

Methods of the Invention

The vectors of the invention are useful in a variety of applications for generating VLVs useful for the treatment, prophylaxis, and/or prevention of a malignancy or infection disease. The vectors are further useful for immunizing a subject against a malignancy or disease, and/or treating, preventing or diminishing risk of malignancy or infectious disease in a subject.

The invention includes a method of immunizing a subject against an heterologous protein associated with an infectious disease. The method comprises administering to the subject a composition comprising virus like vesicles (VLVs) produced by the high-titer hybrid virus vector, wherein the high-titer hybrid virus vector comprises DNA encoding a heterogeneous gene. Expression of the heterogeneous gene induces an immune response to the heterologous protein associated with an infectious disease encoded thereby in the subject. The invention further includes a method of treating a subject in need thereof where the method comprises administering to the subject a composition comprising virus like vesicles (VLVs) produced by the high-titer hybrid virus vector of the invention, wherein the high-titer hybrid virus vector comprises DNA encoding a heterogeneous gene and wherein expression of the heterogeneous gene provides benefit to the subject. In one aspect, the invention includes a method of generating a memory T cell immune response to a heterologous protein in a subject. In another aspect, generating an adaptive B cell immune response to a heterologous protein in a subject.

Also included in the invention is a method of diminishing the risk that a subject will develop an infectious disease. The method comprises administering to the subject a composition comprising the virus like vesicles (VLVs) produced by the high-titer hybrid virus vector, wherein the high-titer hybrid virus vector comprises DNA encoding a heterogeneous gene. Expression of the heterogeneous gene induces an immune response to the heterologous protein associated with the infectious disease encoded thereby in the subject, thereby diminishing the risk that the subject will develop an infectious disease associated with the heterologous protein.

The invention also includes a method of selecting high-titer RNA virus like vesicles (VLVs). This selection is achieved by passaging in a cell culture a hybrid-virus vector comprising an RNA sequence encoding a viral structural protein, wherein the viral structural protein does not comprise an alphavirus structural protein and by screening the generated VLVs for high-titer VLVs using extensive passaging of VLVs in cell culture, direct mutagenesis of the VLVs or any other selection method known in the art. In one aspect the hybrid-virus vector RNA sequence encodes an alphavirus non-structural protein. In another aspect the non-structural protein is a Semliki Forest virus (SFV) non-structural protein.

Pharmaceutical Compositions and Formulations

The VLVs of the invention may be formulated as a pharmaceutical composition. Such a pharmaceutical composition may be in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In one embodiment, the pharmaceutical compositions useful for practicing the method of the invention may be administered to deliver a dose of between $1\times10^5$ and $1\times10^9$ PFU.

In one embodiment, the pharmaceutical compositions useful for practicing the method of the invention may comprise an adjuvant. Suitable adjuvants contemplated by this invention include but are not limited to Freund's complete adjuvant, Freund's incomplete adjuvant, Quil A, Detox, ISCOMs or squalene.

Pharmaceutical compositions that are useful in the methods of the invention may be suitably developed for inhalation, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

The composition of the invention may comprise a preservative from about 0.005% to 2.0% by total weight of the composition. The preservative is used to prevent spoilage in the case of exposure to contaminants in the environment.

Administration/Dosing

The regimen of administration may affect what constitutes an effective amount. For example, the VLVs produced by the high-titer hybrid virus vector of the invention or compositions thereof may be administered to the subject in a single dose, in several divided dosages, as well as staggered dosages may be administered daily or sequentially, or the dose may be continuously infused, or may be a bolus injection. Further, the dosages may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat the disease in the subject. An effective amount of the composition necessary to achieve the intended result will vary and will depend on factors such as the disease to be treated or prevented, the age, sex, weight, condition, general health and prior medical history of the subject being treated, and like factors well-known in the medical arts. In particular embodiments, it is especially advantageous to formulate the composition in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the composition and the heterologous protein to be expressed, and the particular therapeutic effect to be achieved.

Routes of Administration

One skilled in the art will recognize that although more than one route can be used for administration, a particular route can provide a more immediate and more effective reaction than another route. Routes of administration of any of the compositions\of the invention include inhalation, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Kits

In some embodiments a kit is provided for treating, preventing, or ameliorating an a given disease, disorder or condition, or a symptom thereof, as described herein wherein the kit comprises: a) a compound or compositions as described herein; and optionally b) an additional agent or therapy as described herein. The kit can further include instructions or a label for using the kit to treat, prevent, or ameliorate the disease, disorder or condition. In yet other embodiments, the invention extends to kits assays for a given disease, disorder or condition, or a symptom thereof, as described herein. Such kits may, for example, contain the reagents from PCR or other nucleic acid hybridization technology (microarrays) or reagents for immunologically based detection techniques (e.g., ELISpot, ELISA).

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods.

Materials and Methods

The VLV double promoter (dp) vector was linearized with Ascl/SbfI restriction digestion to insert VSV New Jersey G fragment (Carolina Chiale et. al vaccines 2020, 8, 279). A DNA fragment encoding envelope glycoprotein from New Jersey vesiculovirus was gene-synthesized from Synbio Technologies and infused into Ascl and SbfI cloning sites downstream of the second sub-genomic promoter. The resulted VLV dp VSV New Jersey G vector digested with BamHI/PacI and used to clone IL12 and CARG2020 inserts downstream of the first sub-genomic promoter.

To clone single chain IL-12 into dp-IL12 with VSV New Jersey G construct, mouse IL12 p40 and IL12p35 fragments were synthesized as string fragments from Thermo Fisher Scientific. The p40 and p35 fragments were PCR amplified using primers pair modified with elastin linker sequence extensions ((gttcctggagtaggg/gtcccaggtgtgggc (VPGVGVPGVG)) and flanking BamHI and PacI cloning sites. All PCR fragments were amplified with Q5® high-fidelity DNA polymerase, purified from the gel, and infused into VLV dp VSVG New Jersey vector BamHI/PacI cloning sites downstream to the first sub-genomic promoter.

To combine IL17RA ECD HA tag and three shRNAs fragment, the extracellular domain (ECD) part of 17A receptor domain (N-terminal 972 bp fragment) was PCR amplified with modified reverse primer contain HA-tag sequence (YPYDVPDYA). The mouse three shRNAs sequences targeting PDL1 gene at 486,373 and 9 positions were synthesized from Synbio Technologies. To infuse IL17RA ECD HA tag fragment with shRNAs fragment, both fragments were purified from the gel and infused into VLV dp VSVG New Jersey vector BamHI/PacI cloning sites downstream to the first sub-genomic promoter.

To clone final Triple sub-genomic promoter (Tp) CARG-2020 VSV New Jersey G construct, a full-length IL12 fragment, and an IL17 RA ECD HA tag/shRNAs fragment with sub-genomic promoter sequence (as generated above) were amplified using Q5® high-fidelity DNA polymerase. All PCR fragments were purified from the gel and infused into VLV dp VSVG New Jersey vector BamHI/PacI cloning sites downstream to the first sub-genomic promoter. This cloning step creates an extra sub-genomic promoter between IL12 and IL17RA ECD.

All primers to amplify DNA fragments were designed according to NEBuilder instruction and infused according to NEB HiFi DNA Assembly Kit Protocol (E5520S). The recombinant clones screened for positive inserts by DNA restriction digestion. The final positive clones were further confirmed by DNA sequencing (GENEWIZ, NJ).

Example 1: VLVs Expressing IL-12 Cytokine

A high-titer hybrid virus vector (Dp-G(NJ)-IL12) was constructed with several sequence elements in order to produce VLVs competent for the production of IL-12 poly-peptide (SEQ ID NO. 2), i.e. a DNA promoter sequence, a DNA sequence encoding Semliki Forest Virus non-structural protein (SFV nsp1-4), a DNA sequence encoding vesicular stomatitis virus glycoprotein (VSV-G; SEQ ID NO: 11), a DNA sequence encoding IL-12 (SEQ ID NO: 1) as shown in FIG. 4.

BHK-21 cells were transfected with the Dp-G(NJ)-IL12 high-titer hybrid virus vector using standard protocols. The transfected cells were incubated in buffer for 48 hours for VLV production to proceed. Non-transfected cells were incubated as a control. After the incubation period, the supernatants were tested for the presence of IL-12 in an anti-IL-12 Western blot, and IL-12 was observed in the supernatant of the transfected cells but not in the control.

Example 2: Quantification of Secreted IL-12

The quantity of IL-12 secreted after 48 hours of incubation (See Example 1) was determined using a UV-Visible spectroscopic method. A standard curve was prepared using various dilutions of IL-12p70 in the concentration range from 0 to 500 pg/m L. The calibration data curve is shown below in Table 2.

TABLE 3

| Calibration curve for UV-Visible spectroscopic quantification of secreted IL-12. | |
| --- | --- |
| Concentration (pg/mL) (x) | OD Fraction 450/570 nm (y) |
| 500 | 0.7445 |
| 250 | 0.5355 |
| 125 | 0.226 |
| 62.5 | 0.1395 |
| 31.25 | 0.0755 |
| 15.625 | 0.031 |
| 7.8125 | 0.011 |
| 0 | 0.023 |

Best Fit Equation: $y = 0.0021x + 0.0036$

A linear best fit obtained the equation shown in Table 3. The supernatant optical density (OD) was measured at a 4,000-fold dilution to obtain an OD fraction 450/750 nm of 0.3945 corresponding to 0.745 µg of IL-12 per mL of supernatant. This value corresponds to 2 µg of IL-12 per million transfected cells produced.

Example 3: VLV-IL-12 Administration in Mice Limits Tumor Volume

MC38 cells were transplanted subcutaneously into a syngeneic mouse strain to allow tumors to grow under the skin of mice. VLVs producing IL-12 (See example 1; VLV-IL- 12) were produced and prepared as a composition in PBS buffer for injection. A PBS buffer not containing the VLVs was used as the control. The experimental design and timeline are shown in FIG. 5 along with the obtained results. At day 0, the MC38 cells were transplanted subcutaneously and were allowed to grow for a period of 4 days before the administration of either the VLV composition of PBS control, which were administered at 4, 6, 8, 10, 12, and 14 days. At each of the days in which the treatment or control were administered, the tumor volume was calculated from caliper measurements. The results indicate that administration of VLV-IL-12 significantly limited tumor growth in treated mice compared to the control, indicating that VLV-IL-12 is an effective treatment.

Example 4: VLVs Expressing IL-17RA-DN

A high-titer hybrid virus vector (Dp-G(NJ)-IL17RA) was constructed with several sequence elements in order to produce VLVs competent for the production of dominant negative IL-17RA-DN extracellular domain (ECD) polypeptide (SEQ ID NO. 4), i.e. a DNA promoter sequence, a DNA sequence encoding Semliki Forest Virus non-structural protein (SFV nsp1-4), a DNA sequence encoding vesicular stomatitis virus glycoprotein (VSV-G; SEQ ID NO: 11), a DNA sequence encoding IL-17RA-DN (SEQ ID NO. 3) as shown in FIG. 6.

BHK-21 cells were transfected with the Dp-G(NJ)-IL17RA high-titer hybrid virus vector using standard protocols. The transfected cells were incubated in buffer for 48 hours for VLV production to proceed. Non-transfected cells were incubated as a control. After the incubation period, the supernatants were tested for the presence of IL-17RA-DN in a Western blot, and IL-17RA-DN was observed in the supernatant of the transfected cells but not in the control. Additionally, Western blots of BHK-21 cell lysates indicated the presence of IL-17RA-DN in cells transfected with the vector.

Example 5: VLVs Expressing PD-L1 shRNA Checkpoint Inhibitors

Four high-titer hybrid virus vectors were constructed, each with several sequence elements in order to produce VLVs competent for the production of the encoded shRNA sequences, i.e. a DNA promoter sequence, a DNA sequence encoding Semliki Forest Virus non-structural protein (SFV nsp1-4), a DNA sequence encoding vesicular stomatitis virus glycoprotein (VSV-G; SEQ ID NO. 11), and a DNA sequence encoding an shRNA sequence or sequences as shown in FIG. 7A. One vector contained scrambled shRNA (Scr) as a control while three vectors contained the shRNA 486 sequence, the shRNA 373 sequence, or the shRNA 486/373 sequence.

VLVs of the four different vectors were produced in BHK-21 cells as described in Examples 1 and 4. PD-L1 expressing BHK-21 cells were then treated with the produced VLVs. While the VLVs expressing the scrambled (Scr) shRNA did not show suppression of PD-L1 suppression while each of the VLVs expressing the shRNA 486 sequence, the shRNA 373 sequence, or the shRNA 486/373 showed suppression of PD-L1. These results indicate that VLVs can be engineered to express one or more shRNAs effective against gene targets associated with cancer and malignancy.

Example 6: Trivalent CARG2020 VLVs

A high-titer hybrid virus vector (Tp-IL12-1L17RA/ shRNA-G(NJ); CARG2020) was constructed with several sequence elements in order to produce VLVs competent for the production of all three of IL-12 polypeptide (SEQ ID NO. 2), dominant negative IL-17RA-DN extracellular domain (ECD) polypeptide (SEQ ID NO. 4), and PD-L1 checkpoint inhibitor shRNA 486/373/9, i.e. a DNA promoter sequence, a DNA sequence encoding Semliki Forest Virus non-structural protein (SFV nsp1-4), a DNA sequence encoding vesicular stomatitis virus glycoprotein (VSV-G; SEQ ID NO. 11), a DNA sequence encoding IL-12 (SEQ ID NO. 1), a DNA sequence encoding IL-17RA-DN (SEQ ID NO. 3), and a DNA sequence encoding shRNA 486/373/9 (SEQ ID NO. 5), as shown in FIG. 8.

VLVs of the trivalent CARG2020 vectors were produced in BHK-21 cells as described in Examples 1 and 4. The polypeptide products were detected using Western blots, indicating that the trivalent VLVs are able to produce IL-12, IL-17RA-DN, and VSV glycoprotein (VSVG). In vivo PD-L1 downregulation in PD-L1 expressing BHK-21 cells indicated that CARG2020 VLVs (containing shRNA 486/373/9) downregulated PD-L1 more efficiently than the control VLV IL-12 lacking shRNA.

Example 7: Trivalent CARG2020 VLV Administration in Mice Limits Tumor Volume The experimental design and results are shown in FIG. 9. MC38 tumor cells were grafted to the flank of mouse skin at day 0, followed by injections of either GFP-VLV control, IL-12-VLV, or trivalent CARG2020 VLV at days 15, 17, and 21 in the amount of $5 \times 10^7$ particles per injection. In treated animals not receiving the GFP-VLV control, the tumor volume was suppressed indicating that the trivalent CARG-2020 VLV is active and able to suppress tumor growth. Prolonged treatment and monitoring showed that 5 of 7 mice treated with trivalent CARG2020 VLVs achieved complete tumor eradication.

Figure 10A:
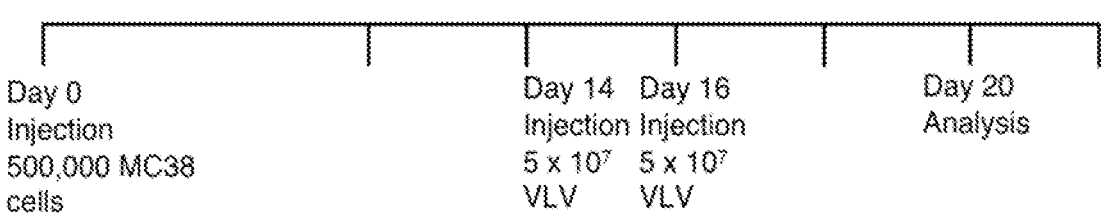
FIG. 10A shows a schematic of the experimental design and timeline. Mice were treated with either GFP control, VLV-IL-12, or the trivalent VLV CARG-2020 and were sacrificed on day 20, and their spleens and tumor tissues were harvested.
Figure 10B:
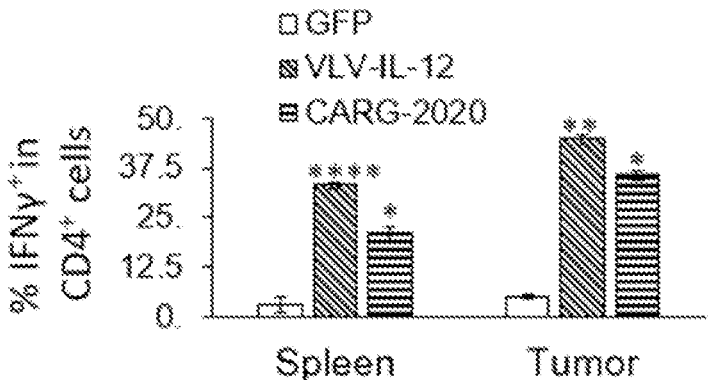
FIGS. 10B-E show flow cytometry analysis results.
Figure 10C:
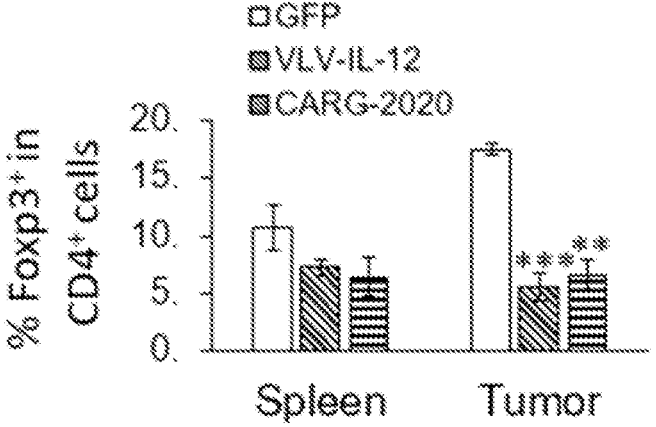
Figure 10D:
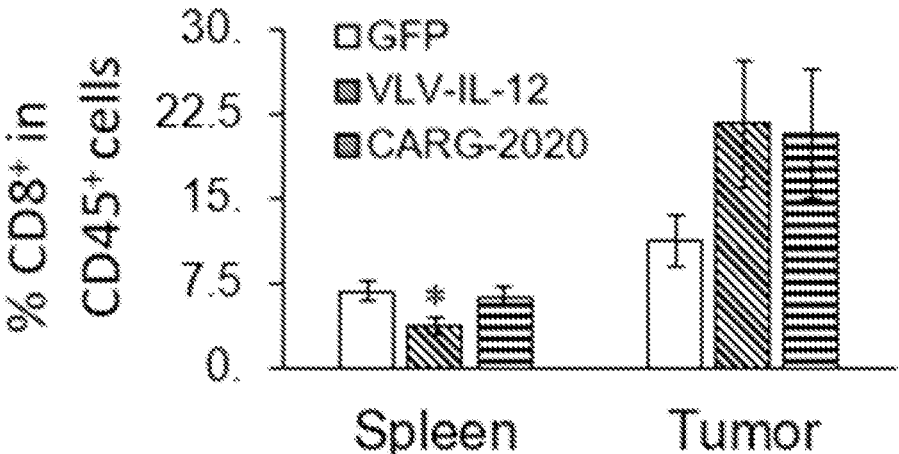
Figure 10E:
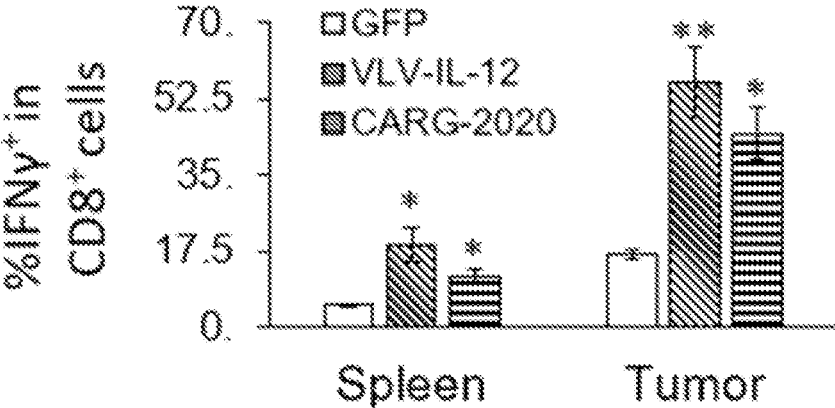
Figure 10F:
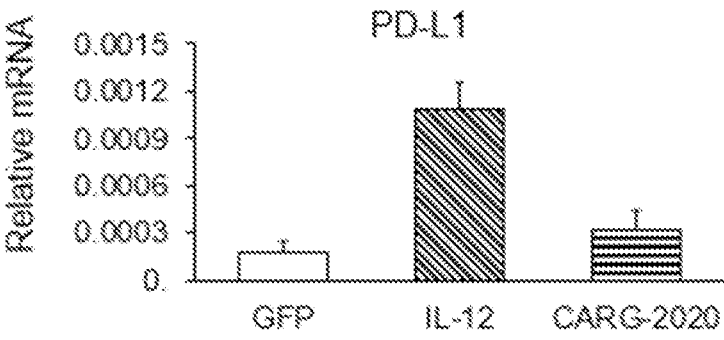
FIGS. 10F-H show q-RT-PCR analysis results for PD-L1, CXCL1, and CXC L2.
Figure 10G:
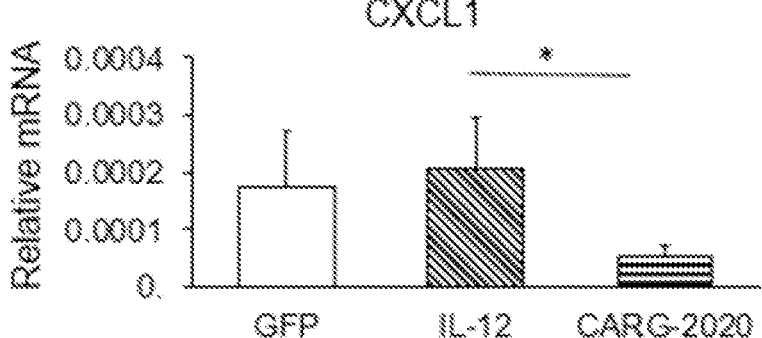
Figure 10H:
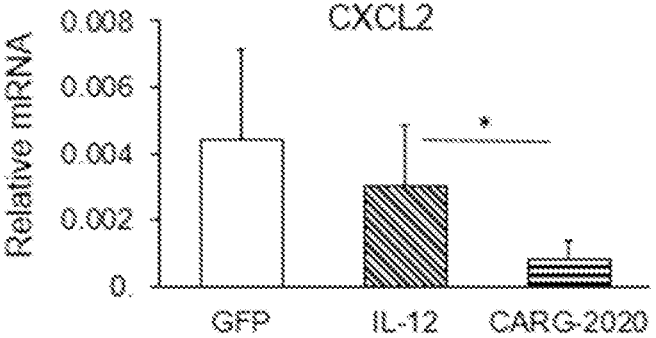

Example 8: CARG2020 Activates Th1 Immunity and Downregulates PD-L1 and IL-17 Related Signaling in Tumors To test the effect of CARG-2020 and VLV-IL-12 in tumor immunity, we treated MC38 tumors with 2 doses via intratumoral injection (FIG. 10A). Mice were sacrificed 4 days after the second dose, and their tumors and spleens were analyzed by flow cytometry and q-RT-PCR. Both CARG-2020 and VLV-IL-12 induced robust Th1-armed immune activation in the spleen and tumors, suggesting a strong immune simulative activity of these agents (FIG. 10B). Treatment of CARG-2020 and VLV-IL-12 also reduced the numbers of regulatory T cells (Tregs) in the tumor (FIG. 10C), and resulted in significantly increased $CD8^+$ T cell activity in the tumor and spleen (FIG. 10 D, E). Compared to VLV-IL-12, CARG-2020 reduced the level of PD-L1, CXCL1 and CXCL2 mRNAs in the tumor, demonstrating the effectiveness of PD-L1 shRNA and IL-17RA-DN transgene, respectively.

Example 9: VLVs are Oncolytic

Normal murine fibroblasts NIH 3T3 were labeled with CFSE dye (green) whereas tumorigenic fibroblasts of line L929 that causes fibrosarcoma were labeled with eFluor670 (red). The cells were co-cultured and either mock treated (control) or treated with VLV at multiplicity of infection (MOI) of 10. Fluorescence microscopy was used to view the cells after 72 hours of incubation had elapsed. The microscopy images indicate that most of the L929 are undergoing apoptosis caused by the replication of the VLV, while normal NIH 3T3 were not lysed.

Example 10: Oncolytic Identification in Colon Cancer Cells, Ovarian Cancer Cells and Acute Lymphoblastic Leukemia Cells Oncolytic identification was performed by flow cytometry analysis. The kit for live/dead cell staining (eBioscience™ Fixable Viability Dye eFluor™ 780 (Thermofisher Scientific, 65-0865-14) was used following manufacture user manual. Briefly, cells were harvested by trypsinization and washed two times with cold PBS, centrifuged at 1500 rpm for 5 min at 4° C., triplicity resuspended the cells using 96 well plate with 100 ul of cells for each well ($5\times10^4$ cells/well), spin down and wash 2 times with cold 1×PBS. Add 100 ul of the live/dead stain (diluted 1:1000 in PBS) to each well. Incubate in dark at 4° C. for 15 minutes; wash 2 times with 200 ul FACS buffer. Add 100 ul fixative solution and incubate in the dark for 45 min at 4° C., Wash cells in permeabilization buffer and stain first with the primary antibodies for 1 hr. After 2-3 washes, stain in secondary Ab for 30 min. Wash 2 times with FACS buffer and resuspend cells in 200 ul FACS buffer, Transfer to cluster tubes for Flow cytometry (LSR II Flow Cytometer at Cell Sorter Core Facility (The Health Center at UCNN) analysis.

The results shown in FIG. 1A demonstrate that ovarian and colon cancer cells undergo an oncolytic process when VLVs are administered thereto. In human cells, the F2 ovarian cancer cell line and the HCT116 colon cancer cell line are both observed to be killed by oncolysis from the administered VLVs. In mouse cells, the TKO ovarian cancer and MC38 colon cancer cell lines are both observed to be killed by oncolysis from the administered VLVs.

The results in FIG. 1B show that acute lymphoblastic leukemia type B cancer cell lines of MN60, REH, and RS4,11 undergo different degrees of oncolysis as a result the administration of VLVs. The least differentiated RS4,11 cancer cell lines are killed most effectively by VLV administration and the oncolysis becomes less prevalent with a higher degree of differentiation in the cell lines. Furthermore, enhanced oncolysis is seen from a larger dose of VLVs (1 multiplicity of infection (MOI) compared to 5 MOI). Normal B cells did not undergo significant oncolysis relative to the REH and RS4-11 cell lines. These results demonstrate that VLVs have a high clinical value for treatment of malignant and chemotherapy resistant leukemia.

Example 11. Oncolytic Pathway Analysis

VLVs are observed to be oncolytic toward malignancies and cancer cells but not toward normal cells. The oncolytic pathway was further investigated using Western blot (FIG. 3). The HCT116 cancer cells were infected with 5 MOI of VLVs (VLV-GFP and VLV-depCC2 (mIL35) for indicated time points. Cells were harvested by trypsinization, lysis of the pellet and via Western blot. The primary antibodies to PARP1, Caspase 8, Caspase 9, TNFα, β-actin were used to detect the cell death related proteins or as a loading control. (the primary antibodies were from Cell Signaling, the secondary anti mouse or rabbit IgG HRP were purchased from Sigma-Aldrich).

The results indicate that infection of the HCT116 cancer cell line with 5 MOI of VLVs results in induced the activation of caspase 8 and caspase 9, expression of tumor necrosis factor (TNF), and cleavage of poly(ADP) ribose polymerase (PARP indicating that oncolysis of cancer cells occurs through apoptotic mechanisms (FIG. 3).

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the compositions and methods of the present invention, where the term comprises is used with respect to the compositions or recited steps of the methods, it is also contemplated that the compositions and methods consist essentially of, or consist of, the recited compositions or steps or components. Furthermore, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as being composed of the components prior to mixing, or prior to a further processing step such as drying, binder removal, heating, sintering, etc. It is recognized that certain components can further react or be transformed into new materials.

All percentages and ratios used herein are on a volume (volume/volume) or weight (weight/weight) basis as shown, or otherwise indicated.

What is claimed is:

1. A high-titer hybrid virus vector for treatment, prophylaxis, or prevention of malignancy or infectious disease comprising the following operably linked sequence elements:

a) a first DNA sequence comprising a DNA promoter sequence;

b) a second DNA sequence encoding alphavirus non-structural protein polynucleotide sequences;

c) a third DNA sequence encoding an alphavirus subgenomic RNA promoter;

d) a fourth DNA sequence comprising:

(i) a sequence domain encoding an IL-12 polypeptide, (ii) a sequence domain encoding an IL-17RA-DN polypeptide, and (iii) a sequence domain encoding a PD-L1-short hairpin RNA (shRNA), wherein each of the sequence domains (i)-(iii) are optionally preceded by a sequence independently selected from the group consisting of one or more subgenomic promoters, a sequence encoding a 2A peptide sequence, or combinations thereof; and e) a fifth DNA sequence encoding a vesiculovirus glycoprotein;

wherein the titer of the high-titer hybrid virus vector is at least about $1 \times 10^7$ plaque forming units (pfu) per mL of virus like vesicles (VLVs), or is at least about $5 \times 10^7$ plaque forming units (pfu) per mL of virus like vesicles (VLVs), or is at least about $1 \times 10^8$ plaque forming units (pfu) per mL of virus like vesicles (VLVs).

2. The high-titer hybrid virus vector of claim 1, wherein the DNA promoter sequence of the first DNA sequence comprises a constitutive promoter for RNA-dependent RNA polymerases.

3. The high-titer hybrid virus vector of claim 1, wherein the alphavirus non-structural protein polynucleotide sequences of the second DNA sequence are Semliki Forest virus (SFV) non-structural protein polynucleotide sequences.

4. The high-titer hybrid virus vector of claim 3, wherein the SFV non-structural protein polypeptide sequences comprise SEQ ID NO. 13.

5. The high-titer hybrid virus vector of claim 1, wherein the alphavirus non-structural protein polynucleotide sequences of the second DNA sequence comprise alphavirus RNA-dependent polymerase.

6. The high-titer hybrid virus vector of claim 5, wherein the alphavirus RNA-dependent polymerase is a Semliki Forest virus (SFV) RNA-dependent polymerase.

7. The high-titer hybrid virus vector of claim 1, wherein the alphavirus subgenomic RNA promoter of the third DNA sequence is a Semliki Forest virus (SFV) subgenomic RNA promoter.

8. The high-titer hybrid virus vector of claim 1, wherein the fourth DNA sequence further comprises at least one sequence domain encoding a cytokine agonist or antagonist polypeptide each independently selected from the group consisting of IL-2, IL-7, IL-15, IL-18, IL-19, IL-35, IL-21, GM-CSF, IL-17, Flt3L, and combinations thereof.

9. The high-titer hybrid virus vector of claim 1, wherein the fourth DNA sequence further comprises at least one sequence domain encoding an shRNA polynucleotide checkpoint inhibitor each independently selected from the group consisting of PD-L2, CTLA-4, LAG-3, TIM-3, TIGIT, CD90, BTLA, CD160, PD-1, and combinations thereof.

10. The high-titer hybrid virus vector of claim 1, wherein the fourth DNA sequence comprises:

a) a sequence domain comprising SEQ ID NO. 6, b) a sequence domain comprising SEQ ID NO. 8, and c) a sequence domain comprising SEQ ID NO. 10, wherein each of the sequence domains a)-c) are optionally preceded by a sequence independently selected from the group consisting of one or more subgenomic promoters, a sequence encoding a 2A peptide sequence, or combinations thereof.

11. The high-titer hybrid virus vector of claim 1, wherein the high-titer hybrid virus vector is trivalent; and wherein the fourth DNA sequence consists of three sequence domains.

12. The high-titer hybrid virus vector of claim 1, wherein the fourth DNA sequence further comprises a sequence domain encoding a polynucleotide or polypeptide inhibitor of an immunosuppressive regulator selected from the group consisting of tryptophan-2,3-dioxygenase (TDO), indoleamine 2, 3-dioxygenase 1 (IDO1), indoleamine 2, 3-dioxygenase 2 (IDO2), and combinations thereof.

13. The high-titer hybrid virus vector of claim 1 further comprising a sixth DNA sequence comprising an expression cassette expressing single or multiple specific antigens of the malignancy or infectious disease.

14. The high-titer hybrid virus vector of claim 13, wherein the expression cassette expresses specific antigens of a tumor or infectious agent to induce humoral and/or cellular immune responses to the antigens.

15. The high-titer hybrid virus vector of claim 1, wherein the vesiculovirus glycoprotein of the fifth DNA sequence comprises envelope glycoprotein of vesicular stomatitis Indiana virus, vesicular stomatitis New Jersey virus, Chandipura virus or structurally related vesiculoviruses.

16. A high-titer hybrid virus vector for generating oncolytic virus-like vesicles (VLVs) comprising the following operably linked sequence elements:

a) a first DNA sequence comprising a DNA promoter sequence;

b) a second DNA sequence encoding alphavirus non-structural protein polynucleotide sequences;

c) a third DNA sequence encoding an alphavirus subgenomic RNA promoter;

d) a fourth DNA sequence comprising:

(i) a sequence domain encoding an IL-12 polypeptide, (ii) a sequence domain encoding an IL-17RA-DN polypeptide, and (iii) a sequence domain encoding a PD-L1-short hairpin RNA (shRNA), wherein each of the sequence domains (i)-(iii) are optionally preceded by a sequence independently selected from the group consisting of one or more subgenomic promoters, a sequence encoding a 2A peptide sequence, or combinations thereof; and e) a fifth DNA sequence encoding a vesiculovirus glycoprotein;

wherein the titer of the high-titer hybrid virus vector is at least about $1 \times 10^7$ plaque forming units (pfu) per mL of virus like vesicles (VLVs), or is at least about $5 \times 10^7$ plaque forming units (pfu) per mL of virus like vesicles (VLVs), or is at least about $1 \times 10^8$ plaque forming units (pfu) per mL of virus like vesicles (VLVs).

17. Virus-like vesicles (VLVs) containing replicon RNA generated by the high-titer hybrid-virus vector of claim 1.

18. The VLVs of claim 17, wherein the replicon RNA is positive-strand capped and polyadenylated.

19. The VLVs of claim 17, wherein the VLVs are selected from the group consisting of self-replicating VLVs, oncolytic VLVs, or capsid-free VLVs.

20. A composition comprising virus-like vesicles (VLVs) produced by the high-titer hybrid virus vector of claim 1.

21. A high-titer hybrid virus vector for treatment, prophylaxis, or prevention of malignancy or infectious disease comprising the following operably linked sequence elements:

a) a first DNA sequence comprising a DNA promoter sequence;

b) a second DNA sequence encoding alphavirus non-structural protein polynucleotide sequences;

c) a third DNA sequence encoding an alphavirus subgenomic RNA promoter;

d) a fourth DNA sequence comprising:
   (i) a sequence domain comprising SEQ ID NO. 6,
   (ii) a sequence domain comprising SEQ ID NO. 8, and
   (iii) a sequence domain comprising SEQ ID NO. 10,
wherein each of the sequence domains (i)-(iii) are optionally preceded by a sequence independently selected
   from the group consisting of one or more subgenomic
   promoters, a sequence encoding a 2A peptide sequence,
   or combinations thereof; and
e) a fifth DNA sequence encoding a vesiculovirus glycoprotein;
wherein the titer of the high-titer hybrid virus vector is at
   least about $1\times10^7$ plaque forming units (pfu) per mL of
   virus like vesicles (VLVs), or is at least about $5\times10^7$
   plaque forming units (pfu) per mL of virus like vesicles
(VLVs), or is at least about $1\times10^8$ plaque forming units
   (pfu) per mL of virus like vesicles (VLVs).

* * * * *

SEQUENCE LISTING

<160> NUMBER OF SEQ ID NOS: 13

<210> SEQ ID NO 1
<211> LENGTH: 1617
<212> TYPE: DNA
<213> ORGANISM: Mus sp.

<400> SEQUENCE: 1

-continued

```
atgtgtcctc agaagctaac catctcctgg tttgccatcg ttttgctggt gtctccactc       60
atggccatgt gggagctgga gaaagacgtt tatgttgtag aggtggactg gactcccgat      120
gcccctggag aaacagtgaa cctcacctgt gacacgcctg aagaagatga catcacctgg      180
acctcagacc agagacatgg agtcataggc tctggaaaga ccctgaccat cactgtcaaa      240
gagtttctag atgctggcca gtacacctgc cacaaggag gcgagactct gagccactca       300
catctgctgc tccacaagaa ggaaaatgga atttggtcca ctgaaatttt aaaaaatttc      360
aaaaacaaga ctttcctgaa gtgtgaagca ccaaattact ccggacggtt cacgtgctca      420
tggctggtgc aaagaaacat ggacttgaag ttcaacatca gagcagtag cagttcccct       480 gactctcggg cagtgacatg tggaatggcg tctctgtctg cagagaaggt cacactggac      540
caaagggact atgagaagta ttcagtgtcc tgccaggagg atgtcacctg cccaactgcc      600
gaggagaccc tgcccattga actggcgttg gaagcacggc agcagaataa atatgagaac      660
tacagcacca gcttcttcat cagggacatc atcaaaccag acccgcccaa gaacttgcag      720
atgaagcctt tgaagaactc acaggtggag gtcagctggg agtaccctga ctcctggagc      780
actccccatt cctacttctc cctcaagttc tttgttcgaa tccagcgcaa gaaagaaaag      840
atgaaggaga cagaggaggg gtgtaaccag aaaggtgcgt tcctcgtaga gaagacatct      900
accgaagtcc aatgcaaagg cgggaatgtc tgcgtgcaag ctcaggatcg ctattacaat      960
tcctcatgca gcaagtgggc atgtgttccc tgcagggtcc gatccgttcc tggagtaggg     1020
gtcccaggtg tgggcagggt cattccagtc tctggacctg ccaggtgtct tagccagtcc     1080
cgaaacctgc tgaagaccac agatgacatg gtgaagacgg ccagagaaaa actgaaacat     1140
tattcctgca ctgctgaaga catcgatcat gaagacatca cacgggacca aaccagcaca     1200
ttgaagacct gtttaccact ggaactacac aagaacgaga gttgcctggc tactagagag     1260
acttcttcca caacaagagg gagctgcctg cccccacaga agacgtcttt gatgatgacc     1320
ctgtgccttg gtagcatcta tgaggacttg aagatgtacc agacagagtt ccaggccatc     1380
aacgcagcac ttcagaatca caaccatcag cagatcattc tagacaaggg catgctggtg     1440
gccatcgatg agctgatgca gtctctgaat cataatggcg agactctgcg ccagaaacct     1500
cctgtgggag aagcagaccc ttacagagtg aaaatgaagc tctgcatcct gcttcacgcc     1560
ttcagcaccc gcgtcgtgac catcaacagg gtgatgggct atctgagctc cgcctag       1617
```

<210> SEQ ID NO 2
<211> LENGTH: 538
<212> TYPE: PRT
<213> ORGANISM: Mus sp.

<400> SEQUENCE: 2

```
Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
```

-continued

```
                    85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
            115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
            195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
                260                 265                 270

Arg Ile Gln Arg Lys Lys Glu Lys Met Lys Glu Thr Glu Glu Gly Cys
            275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Val
                325                 330                 335

Pro Gly Val Gly Val Pro Gly Val Gly Arg Val Ile Pro Val Ser Gly
            340                 345                 350

Pro Ala Arg Cys Leu Ser Gln Ser Arg Asn Leu Leu Lys Thr Thr Asp
            355                 360                 365

Asp Met Val Lys Thr Ala Arg Glu Lys Leu Lys His Tyr Ser Cys Thr
    370                 375                 380

Ala Glu Asp Ile Asp His Glu Asp Ile Thr Arg Asp Gln Thr Ser Thr
385                 390                 395                 400

Leu Lys Thr Cys Leu Pro Leu Glu Leu His Lys Asn Glu Ser Cys Leu
                405                 410                 415

Ala Thr Arg Glu Thr Ser Ser Thr Thr Arg Gly Ser Cys Leu Pro Pro
            420                 425                 430

Gln Lys Thr Ser Leu Met Met Thr Leu Cys Leu Gly Ser Ile Tyr Glu
            435                 440                 445

Asp Leu Lys Met Tyr Gln Thr Glu Phe Gln Ala Ile Asn Ala Ala Leu
    450                 455                 460

Gln Asn His Asn His Gln Gln Ile Ile Leu Asp Lys Gly Met Leu Val
465                 470                 475                 480

Ala Ile Asp Glu Leu Met Gln Ser Leu Asn His Asn Gly Glu Thr Leu
                485                 490                 495

Arg Gln Lys Pro Pro Val Gly Glu Ala Asp Pro Tyr Arg Val Lys Met
            500                 505                 510
```

```
Lys Leu Cys Ile Leu Leu His Ala Phe Ser Thr Arg Val Val Thr Ile
        515                 520                 525

Asn Arg Val Met Gly Tyr Leu Ser Ser Ala
    530                 535
```

<210> SEQ ID NO 3
<211> LENGTH: 996
<212> TYPE: DNA
<213> ORGANISM: Mus sp.

<400> SEQUENCE: 3

```
atggcgattc ggcgctgctg gccacgggtc gtccccgggc ccgcgctggg atggctgctt      60
ctgctgctga acgttctggc cccgggccgc gcctccccgc gcctcctcga cttcccggct     120
ccggtctgcg cgcaggaggg gctgagctgc agagtcaaga atagtacttg tctggatgac     180
agctggatcc accccaaaaa cctgacccct tcttccccaa aaaacatcta tatcaatctt     240
agtgtttcct ctacccagca cggagaatta gtccctgtgt tgcatgttga gtggaccctg     300
cagacagatg ccagcatcct gtacctcgag ggtgcagagc tgtccgtcct gcagctgaac     360
accaatgagc ggctgtgtgt caagttccag tttctgtcca tgctgcagca tcaccgtaag     420
cggtggcggt tttccttcag ccactttgtg gtagatcctg gccaggagta tgaagtgact     480
gttcaccacc tgccgaagcc catccctgat ggggacccaa accacaaatc caagatcatc     540
tttgtgcctg actgtgagga cagcaagatg aagatgacta cctcatgcgt gagctcaggc     600
agcctttggg atcccaacat cactgtggag accttggaca cacagcatct gcgagtggac     660
ttcaccctgt ggaatgaatc caccccctac caggtcctgc tggaaagttt ctccgactca     720
gagaaccaca gctgctttga tgtcgttaaa caaatatttg cgcccaggca agaagaattc     780
catcagcgag ctaatgtcac attcactcta agcaagtttc actggtgctg ccatcaccac     840
gtgcaggtcc agcccttctt cagcagctgc ctaaatgact gtttgagaca cgctgtgact     900
gtgccctgcc cagtaatctc aaataccaca gttcccaagc cagttgcaga ctacattccc     960
ctgtggtacc cttacgacgt gccagattac gcttag                              996
```

<210> SEQ ID NO 4
<211> LENGTH: 331
<212> TYPE: PRT
<213> ORGANISM: Mus sp.

<400> SEQUENCE: 4

```
Met Ala Ile Arg Arg Cys Trp Pro Arg Val Val Pro Gly Pro Ala Leu
1               5                   10                  15

Gly Trp Leu Leu Leu Leu Leu Asn Val Leu Ala Pro Gly Arg Ala Ser
            20                  25                  30

Pro Arg Leu Leu Asp Phe Pro Ala Pro Val Cys Ala Gln Glu Gly Leu
        35                  40                  45

Ser Cys Arg Val Lys Asn Ser Thr Cys Leu Asp Asp Ser Trp Ile His
    50                  55                  60

Pro Lys Asn Leu Thr Pro Ser Ser Pro Lys Asn Ile Tyr Ile Asn Leu
65                  70                  75                  80

Ser Val Ser Ser Thr Gln His Gly Glu Leu Val Pro Val Leu His Val
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Lys
```

-continued

```
        115                 120                 125
Phe Gln Phe Leu Ser Met Leu Gln His His Arg Lys Arg Trp Arg Phe
    130                 135                 140
Ser Phe Ser His Phe Val Val Asp Pro Gly Gln Glu Tyr Glu Val Thr
145                 150                 155                 160
Val His His Leu Pro Lys Pro Ile Pro Asp Gly Asp Pro Asn His Lys
                165                 170                 175
Ser Lys Ile Ile Phe Val Pro Asp Cys Glu Asp Ser Lys Met Lys Met
                180                 185                 190
Thr Thr Ser Cys Val Ser Ser Gly Ser Leu Trp Asp Pro Asn Ile Thr
                195                 200                 205
Val Glu Thr Leu Asp Thr Gln His Leu Arg Val Asp Phe Thr Leu Trp
    210                 215                 220
Asn Glu Ser Thr Pro Tyr Gln Val Leu Leu Glu Ser Phe Ser Asp Ser
225                 230                 235                 240
Glu Asn His Ser Cys Phe Asp Val Val Lys Gln Ile Phe Ala Pro Arg
                245                 250                 255
Gln Glu Glu Phe His Gln Arg Ala Asn Val Thr Phe Thr Leu Ser Lys
                260                 265                 270
Phe His Trp Cys Cys His His His Val Gln Val Gln Pro Phe Phe Ser
                275                 280                 285
Ser Cys Leu Asn Asp Cys Leu Arg His Ala Val Thr Val Pro Cys Pro
    290                 295                 300
Val Ile Ser Asn Thr Thr Val Pro Lys Pro Val Ala Asp Tyr Ile Pro
305                 310                 315                 320
Leu Trp Tyr Pro Tyr Asp Val Pro Asp Tyr Ala
                325                 330
```

```
<210> SEQ ID NO 5
<211> LENGTH: 422
<212> TYPE: DNA
<213> ORGANISM: Mus sp.

<400> SEQUENCE: 5
acgttagctc gagaagaagg tatattgctg ttgacagtga gcgacggaca aacagtgacc      60
accttagtga agcttcagat gtaaggtggt cactgtttgt ccgctgccta ctgcctcgga     120
cttcaagggg tcagtcagat tttttctcga gaagaaggta tattgctgtt gacagtgagc     180
gacgctgaaa gtcaatgccc catagtgaag cttcagatgt atggggcatt gactttcagc     240
gctgcctact gcctcggact tcaaggggtc agtcagaatt tttctcgaga agaaggtata     300
ttgctgttga cagtgagcga cgatttgctg gcattatata tagtgaagct tcagatgtat     360
atataatgcc agcaaatcgc tgcctactgc ctcggacttc aaggggtcag tcagaatttt     420
tt                                                                     422
```

```
<210> SEQ ID NO 6
<211> LENGTH: 1551
<212> TYPE: DNA
<213> ORGANISM: Homo sapiens

<400> SEQUENCE: 6
gtggccatat gggaactgaa gaaagatgtt tatgtcgtag aattggattg gtatccggat      60
gcccctggag aaatggtggt cctcacctgt gacacccctg aagaagatgg tatcacctgg     120
accttggacc agagcagtga ggtcttaggc tctggcaaaa ccctgaccat ccaagtcaaa     180
```

-continued

```
gagtttggag atgctggcca gtacacctgt cacaaaggag gcgaggttct aagccattcg      240
ctcctgctgc ttcacaaaaa ggaagatgga atttggtcca ctgatatttt aaaggaccag      300
aaagaaccca aaaataagac ctttctaaga tgcgaggcca agaattattc tggacgtttc      360
acctgctggt ggctgacgac aatcagtact gatttgacat tcagtgtcaa aagcagcaga      420
ggctcttctg acccccaagg ggtgacgtgc ggagctgcta cactctctgc agagagagtc      480 agagggaca acaaggagta tgagtactca gtggagtgcc aggaggacag tgcctgccca       540
gctgctgagg agagtctgcc cattgaggtc atggtggatg ccgttcacaa gctcaagtat      600
gaaaactaca ccagcagctt cttcatcagg gacatcatca aacctgaccc acccaagaac      660
ttgcagctga agccattaaa gaattctcgg caggtggagg tcagctggga gtaccctgac      720
acctggagta ctccacattc ctacttctcc ctgacattct gcgttcaggt ccagggcaag      780
agcaagagag aaaagaaaga tagagtcttc acggacaaga cctcagccac ggtcatctgc      840
cgcaaaaatg ccagcattag cgtgcgggcc caggaccgct actatagctc atcttggagc      900
gaatgggcat ctgtgccctg cagtgttcct ggagtagggg tacctggggt gggcgccaga      960
aacctccccg tggccactcc agacccagga atgttcccat gccttcacca ctcccaaaac     1020
ctgctgaggg ccgtcagcaa catgctccag aaggccagac aaactctaga attttacccc     1080
tgcacttctg aagagattga tcatgaagat atcacaaaag ataaaaccag cacagtggag     1140
gcctgtttac cattggaatt aaccaagaat gagagttgcc taaattccag agagacctct     1200
ttcataacta tgggagttg cctggcctcc agaaagacct ctttttatgat ggccctgtgc     1260 cttagtagta tttatgaaga cttgaagatg taccaggtgg agttcaagac catgaatgca     1320
aagctgctga tggatcctaa gaggcagatc tttctagatc aaaacatgct ggcagttatt     1380
gatgagctga tgcaggccct gaatttcaac agtgagactg tgccacaaaa atcctccctt     1440
gaagaaccgg atttttataa aactaaaatc aagctctgca tacttcttca tgctttcaga     1500
attcgggcag tgactattga tagagtgatg agctatctga atgcttccta a               1551
```

```
<210> SEQ ID NO 7
<211> LENGTH: 536
<212> TYPE: PRT
<213> ORGANISM: Homo sapiens

<400> SEQUENCE: 7

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
```

-continued

```
        130                135                140
Leu Thr Thr Ile Ser Thr Asp Leu Thr Phe Ser Val Lys Ser Ser Arg
145                150                155                160

Gly Ser Ser Asp Pro Gln Gly Val Thr Cys Gly Ala Ala Thr Leu Ser
                165                170                175

Ala Glu Arg Val Arg Gly Asp Asn Lys Glu Tyr Glu Tyr Ser Val Glu
                180                185                190

Cys Gln Glu Asp Ser Ala Cys Pro Ala Ala Glu Glu Ser Leu Pro Ile
                195                200                205

Glu Val Met Val Asp Ala Val His Lys Leu Lys Tyr Glu Asn Tyr Thr
        210                215                220

Ser Ser Phe Phe Ile Arg Asp Ile Ile Lys Pro Asp Pro Pro Lys Asn
225                230                235                240

Leu Gln Leu Lys Pro Leu Lys Asn Ser Arg Gln Val Glu Val Ser Trp
                245                250                255

Glu Tyr Pro Asp Thr Trp Ser Thr Pro His Ser Tyr Phe Ser Leu Thr
                260                265                270

Phe Cys Val Gln Val Gln Gly Lys Ser Lys Arg Glu Lys Lys Asp Arg
                275                280                285

Val Phe Thr Asp Lys Thr Ser Ala Thr Val Ile Cys Arg Lys Asn Ala
        290                295                300

Ser Ile Ser Val Arg Ala Gln Asp Arg Tyr Tyr Ser Ser Ser Trp Ser
305                310                315                320

Glu Trp Ala Ser Val Pro Cys Ser Val Pro Gly Val Gly Val Pro Gly
                325                330                335

Val Gly Ala Arg Asn Leu Pro Val Ala Thr Pro Asp Pro Gly Met Phe
                340                345                350

Pro Cys Leu His His Ser Gln Asn Leu Leu Arg Ala Val Ser Asn Met
                355                360                365

Leu Gln Lys Ala Arg Gln Thr Leu Glu Phe Tyr Pro Cys Thr Ser Glu
        370                375                380

Glu Ile Asp His Glu Asp Ile Thr Lys Asp Lys Thr Ser Thr Val Glu
385                390                395                400

Ala Cys Leu Pro Leu Glu Leu Thr Lys Asn Glu Ser Cys Leu Asn Ser
                405                410                415

Arg Glu Thr Ser Phe Ile Thr Asn Gly Ser Cys Leu Ala Ser Arg Lys
                420                425                430

Thr Ser Phe Met Met Ala Leu Cys Leu Ser Ser Ile Tyr Glu Asp Leu
                435                440                445

Lys Met Tyr Gln Val Glu Phe Lys Thr Met Asn Ala Lys Leu Leu Met
        450                455                460

Asp Pro Lys Arg Gln Ile Phe Leu Asp Gln Asn Met Leu Ala Val Ile
465                470                475                480

Asp Glu Leu Met Gln Ala Leu Asn Phe Asn Ser Glu Thr Val Pro Gln
                485                490                495

Lys Ser Ser Leu Glu Glu Pro Asp Phe Tyr Lys Thr Lys Ile Lys Leu
                500                505                510

Cys Ile Leu Leu His Ala Phe Arg Ile Arg Ala Val Thr Ile Asp Arg
                515                520                525

Val Met Ser Tyr Leu Asn Ala Ser
        530                535
```

<210> SEQ ID NO 8

-continued

```
<211> LENGTH: 963
<212> TYPE: DNA
<213> ORGANISM: Homo sapiens

<400> SEQUENCE: 8
atgggggccg cacgcagccc gccgtccgct gtcccggggc ccctgctggg gctgctcctg      60
ctgctcctgg gcgtgctggc cccgggtggc gcctccctgc gactcctgga ccaccgggcg     120
ctggtctgct cccagccggg gctaaactgc acggtcaaga atagtacctg cctggatgac     180
agctggattc accctcgaaa cctgaccccc tcctccccaa aggacctgca gatccagctg     240
cactttgccc acacccaaca aggagacctg ttccccgtgg ctcacatcga atggacactg     300
cagacagacg ccagcatcct gtacctcgag ggtgcagagt atctgtcct gcagctgaac     360 accaatgaac gtttgtgcgt caggtttgag tttctgtcca aactgaggca tcaccacagg     420
cggtggcgtt ttaccttcag ccactttgtg gttgaccctg accaggaata tgaggtgacc     480
gttcaccacc tgcccaagcc catccctgat ggggacccaa accaccagtc caagaatttc     540
cttgtgcctg actgtgagca cgccaggatg aaggtaacca cgccatgcat gagctcaggc     600
agcctgtggg accccaacat caccgtggag accctggagg cccaccagct gcgtgtgagc     660
ttcaccctgt ggaacgaatc tacccattac cagatcctgc tgaccagttt tccgcacatg     720
gagaaccaca gttgctttga gcacatgcac cacatacctg cgcccagacc agaagagttc     780
caccagcgat ccaacgtcac actcactcta cgcaacctta aagggtgctg tcgccaccaa     840
gtgcagatcc agcccttctt cagcagctgc ctcaatgact gcctcagaca ctccgcgact     900
gtttcctgcc cagaaatgcc agacactcca gaaccaattc cggactacat gcccctgtgg     960
tag                                                                     963

<210> SEQ ID NO 9
<211> LENGTH: 320
<212> TYPE: PRT
<213> ORGANISM: Homo sapiens

<400> SEQUENCE: 9

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
            85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
        130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
```

-continued

```
                165                 170                 175
Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320
```

<210> SEQ ID NO 10
<211> LENGTH: 422
<212> TYPE: DNA
<213> ORGANISM: Homo sapiens

<400> SEQUENCE: 10

```
acgttagctc gagaagaagg tatattgctg ttgacagtga gcgacggcat ttgctgaacg      60
catttagtga agcttcagat gtaaatgcgt tcagcaaatg ccgctgccta ctgcctcgga     120
cttcaagggg tcagtcagat tttttctcga gaagaaggta tattgctgtt gacagtgagc     180
gacggaagac ctgaaggttc agtagtgaag cttcagatgt actgaacctt caggtcttcc     240
gctgcctact gcctcggact tcaaggggtc agtcagaatt tttctcgaga agaaggtata     300
ttgctgttga cagtgagcga cgtcctgagt ggtaagacca tagtgaagct tcagatgtat     360
ggtcttacca ctcaggacgc tgcctactgc ctcggacttc aaggggtcag tcagaatttt     420
tt                                                                     422
```

<210> SEQ ID NO 11
<211> LENGTH: 1554
<212> TYPE: DNA
<213> ORGANISM: Vesicular stomatitis virus

<400> SEQUENCE: 11

```
atgctgagct acctgatctt cgccctggcc gtgtctccta tcctgggcaa gatcgagatc      60
gtgttccctc agcacaccac cggcgactgg aaaagagtgc cccacgagta caactactgc     120
cccaccagcg ccgacaagaa tagccacgga acacagacag gcatccccgt ggaactgacc     180
atgcctaagg gcctgacaac ccaccaggtg gaaggcttca tgtgtcacag cgccctgtgg     240
atgaccacct gtgactttcg ttggtacggc cccaagtaca tcacccacag catccacaac     300
gaggaaccca ccgactacca gtgcctggaa gccatcaaga gctacaagga cggcgtgtcc     360
ttcaatcctg gattcccacc tcagagctgc ggctacggca cagtgacaga tgccgaggct     420
cacatcgtga ccgtgacacc tcacagcgtg aaggtggacg agtacacagg cgagtggatc     480
gaccctcact tcatcggcgg cagatgcaag ggccaaatct gcgagacagt gcacaacagc     540
```

-continued

```
accaagtggt tcaccagctc cgatggcgag agcgtgtgca gccagctgtt taccctcgtc     600
ggcggcatct tcttcagcga cagcgaagag atcaccagca tgggcctgcc tgaaaccgga     660
atcagaagca actacttccc ctacatcagc accgagggaa tctgcaagat gcccttctgt     720
cggaagcagg gctacaagct gaagaacgac ctgtggttcc agatcatgga ccccgacctg     780
gataagaccg tgcgggatct gccccacatc aaggactgtg atctgagcag cagcatcatc     840
acccctggcg agcacgccac agacatcagc ctgatcagcg acgtggaacg catcctggac     900
tacgccctgt gccagaacac ctggtctaag atcgagtccg gcgagcccat cacacccgtg     960
gatctgtctt atctgggccc caagaatcct ggcgtgggcc ctgtgttcac catcatcaat    1020
ggcagcctgc actacttcac cagcaagtac ctgagagtgg aactggaaag ccctgtgatc    1080
cccagaatgg aaggcaaggt ggccggcaca agaatcgtca gacagctgtg ggaccagtgg    1140
ttcccattcg gcgaggtgga aatcggccct aacggcgtgc tgaaaacaaa gcaggggtat    1200
aagttcccgc tgcacatcat cggcaccggc gaagtggaca gcgacatcaa gatggaacgg    1260
gtcgtgaagc actgggagca ccctcacatt gaggccgctc agaccttcct gaagaaggac    1320
gatacaggcg aggtgctgta ctacggcgat accggggtgt caaagaaccc cgtcgaactg    1380
gtggaaggat ggtttagcgg atggcggtct agcctgatgg gagtgctggc cgtgatcatc    1440
ggcttcgtga tcctgatgtt cctgattaag ctgatcgggg tgctgagcag cctgttcaga    1500
cccaagagaa ggcccatcta caagagcgac gtcgagatgg cccacttccg gtag           1554

<210> SEQ ID NO 12
<211> LENGTH: 517
<212> TYPE: PRT
<213> ORGANISM: Vesicular stomatitis virus

<400> SEQUENCE: 12

Met Leu Ser Tyr Leu Ile Phe Ala Leu Ala Val Ser Pro Ile Leu Gly
1               5                   10                  15

Lys Ile Glu Ile Val Phe Pro Gln His Thr Thr Gly Asp Trp Lys Arg
            20                  25                  30

Val Pro His Glu Tyr Asn Tyr Cys Pro Thr Ser Ala Asp Lys Asn Ser
        35                  40                  45

His Gly Thr Gln Thr Gly Ile Pro Val Glu Leu Thr Met Pro Lys Gly
    50                  55                  60

Leu Thr Thr His Gln Val Glu Gly Phe Met Cys His Ser Ala Leu Trp
65                  70                  75                  80

Met Thr Thr Cys Asp Phe Arg Trp Tyr Gly Pro Lys Tyr Ile Thr His
                85                  90                  95

Ser Ile His Asn Glu Glu Pro Thr Asp Tyr Gln Cys Leu Glu Ala Ile
            100                 105                 110

Lys Ser Tyr Lys Asp Gly Val Ser Phe Asn Pro Gly Phe Pro Pro Gln
        115                 120                 125

Ser Cys Gly Tyr Gly Thr Val Thr Asp Ala Glu Ala His Ile Val Thr
    130                 135                 140

Val Thr Pro His Ser Val Lys Val Asp Glu Tyr Thr Gly Glu Trp Ile
145                 150                 155                 160

Asp Pro His Phe Ile Gly Gly Arg Cys Lys Gly Gln Ile Cys Glu Thr
                165                 170                 175

Val His Asn Ser Thr Lys Trp Phe Thr Ser Ser Asp Gly Glu Ser Val
            180                 185                 190

Cys Ser Gln Leu Phe Thr Leu Val Gly Gly Ile Phe Phe Ser Asp Ser
```

-continued

```
            195                 200                 205

Glu Glu Ile Thr Ser Met Gly Leu Pro Glu Thr Gly Ile Arg Ser Asn
    210                 215                 220

Tyr Phe Pro Tyr Ile Ser Thr Glu Gly Ile Cys Lys Met Pro Phe Cys
225                 230                 235                 240

Arg Lys Gln Gly Tyr Lys Leu Lys Asn Asp Leu Trp Phe Gln Ile Met
                245                 250                 255

Asp Pro Asp Leu Asp Lys Thr Val Arg Asp Leu Pro His Ile Lys Asp
                260                 265                 270

Cys Asp Leu Ser Ser Ser Ile Ile Thr Pro Gly Glu His Ala Thr Asp
                275                 280                 285

Ile Ser Leu Ile Ser Asp Val Glu Arg Ile Leu Asp Tyr Ala Leu Cys
                290                 295                 300

Gln Asn Thr Trp Ser Lys Ile Glu Ser Gly Glu Pro Ile Thr Pro Val
305                 310                 315                 320

Asp Leu Ser Tyr Leu Gly Pro Lys Asn Pro Gly Val Gly Pro Val Phe
                325                 330                 335

Thr Ile Ile Asn Gly Ser Leu His Tyr Phe Thr Ser Lys Tyr Leu Arg
                340                 345                 350

Val Glu Leu Glu Ser Pro Val Ile Pro Arg Met Glu Gly Lys Val Ala
                355                 360                 365

Gly Thr Arg Ile Val Arg Gln Leu Trp Asp Gln Trp Phe Pro Phe Gly
                370                 375                 380

Glu Val Glu Ile Gly Pro Asn Gly Val Leu Lys Thr Lys Gln Gly Tyr
385                 390                 395                 400

Lys Phe Pro Leu His Ile Ile Gly Thr Gly Glu Val Asp Ser Asp Ile
                405                 410                 415

Lys Met Glu Arg Val Val Lys His Trp Glu His Pro His Ile Glu Ala
                420                 425                 430

Ala Gln Thr Phe Leu Lys Lys Asp Asp Thr Gly Glu Val Leu Tyr Tyr
                435                 440                 445

Gly Asp Thr Gly Val Ser Lys Asn Pro Val Glu Leu Val Glu Gly Trp
                450                 455                 460

Phe Ser Gly Trp Arg Ser Ser Leu Met Gly Val Leu Ala Val Ile Ile
465                 470                 475                 480

Gly Phe Val Ile Leu Met Phe Leu Ile Lys Leu Ile Gly Val Leu Ser
                485                 490                 495

Ser Leu Phe Arg Pro Lys Arg Arg Pro Ile Tyr Lys Ser Asp Val Glu
                500                 505                 510

Met Ala His Phe Arg
        515

<210> SEQ ID NO 13
<211> LENGTH: 2432
<212> TYPE: PRT
<213> ORGANISM: Semliki forest virus

<400> SEQUENCE: 13

Met Ala Ala Lys Val His Val Asp Ile Glu Ala Asp Ser Pro Phe Ile
1               5                   10                  15

Lys Ser Leu Gln Lys Ala Phe Pro Ser Phe Glu Val Glu Ser Leu Gln
                20                  25                  30

Val Thr Pro Asn Asp His Ala Asn Ala Arg Ala Phe Ser His Leu Ala
        35                  40                  45
```

-continued

```
Thr Lys Leu Ile Glu Gln Glu Thr Asp Lys Asp Thr Leu Ile Leu Asp
    50              55                  60

Ile Gly Ser Ala Pro Ser Arg Arg Met Met Ser Thr His Lys Tyr His
65              70                  75                  80

Cys Val Cys Pro Met Arg Ser Ala Glu Asp Pro Glu Arg Leu Val Cys
                85                  90                  95

Tyr Ala Lys Lys Leu Ala Ala Ala Ser Glu Lys Val Leu Asp Arg Glu
            100                 105                 110

Ile Ala Gly Lys Ile Thr Asp Leu Gln Thr Val Met Ala Thr Pro Asp
            115                 120                 125

Ala Glu Ser Pro Thr Phe Cys Leu His Thr Asp Val Thr Cys Arg Thr
    130                 135                 140

Ala Ala Glu Val Ala Val Tyr Gln Asp Val Tyr Ala Val His Ala Pro
145                 150                 155                 160

Thr Ser Leu Tyr His Gln Ala Met Lys Gly Val Arg Thr Ala Tyr Trp
                165                 170                 175

Ile Gly Phe Asp Thr Thr Pro Phe Met Phe Asp Ala Leu Ala Gly Ala
            180                 185                 190

Tyr Pro Thr Tyr Ala Thr Asn Trp Ala Asp Glu Gln Val Leu Gln Ala
            195                 200                 205

Arg Asn Ile Gly Leu Cys Ala Ala Ser Leu Thr Glu Gly Arg Leu Gly
    210                 215                 220

Lys Leu Ser Ile Leu Arg Lys Lys Gln Leu Lys Pro Cys Asp Thr Val
225                 230                 235                 240

Met Phe Ser Val Gly Ser Thr Leu Tyr Thr Glu Ser Arg Lys Leu Leu
                245                 250                 255

Arg Ser Trp His Leu Pro Ser Val Phe His Leu Lys Gly Lys Gln Ser
                260                 265                 270

Phe Thr Cys Arg Cys Asp Thr Ile Val Ser Cys Glu Gly Tyr Val Val
            275                 280                 285

Lys Lys Ile Thr Met Cys Pro Gly Leu Tyr Gly Lys Thr Val Gly Tyr
    290                 295                 300

Ala Val Thr Tyr His Ala Glu Gly Phe Leu Val Cys Lys Thr Thr Asp
305                 310                 315                 320

Thr Val Lys Gly Glu Arg Val Ser Phe Pro Val Cys Thr Tyr Val Pro
            325                 330                 335

Ser Thr Ile Cys Asp Gln Met Thr Gly Ile Leu Ala Thr Asp Ile Thr
            340                 345                 350

Pro Glu Asp Ala Gln Lys Leu Leu Val Gly Leu Asn Gln Arg Ile Val
            355                 360                 365

Val Asn Gly Arg Thr Gln Arg Asn Thr Asn Thr Met Lys Asn Tyr Leu
    370                 375                 380

Leu Pro Ile Val Ala Val Ala Phe Ser Lys Trp Ala Arg Glu Tyr Lys
385                 390                 395                 400

Ala Asp Leu Asp Asp Glu Lys Pro Leu Gly Val Arg Glu Arg Ser Leu
            405                 410                 415

Thr Cys Cys Cys Leu Trp Ala Phe Lys Thr Arg Lys Met His Thr Met
            420                 425                 430

Tyr Lys Lys Pro Asp Thr Gln Thr Ile Val Lys Val Pro Ser Glu Phe
            435                 440                 445

Asn Ser Phe Val Ile Pro Ser Leu Trp Ser Thr Gly Leu Ala Ile Pro
    450                 455                 460

Val Arg Ser Arg Ile Lys Met Leu Leu Ala Lys Lys Thr Lys Arg Glu
```

-continued

```
465               470               475               480

Ser Ile Pro Val Leu Asp Ala Ser Ser Ala Arg Asp Ala Glu Gln Glu
                485               490               495

Glu Lys Glu Arg Leu Glu Ala Glu Leu Thr Arg Glu Ala Leu Pro Pro
            500               505               510

Leu Val Pro Thr Ala Pro Ala Glu Thr Gly Val Val Asp Val Asp Val
            515               520               525

Glu Glu Leu Glu Tyr His Ala Gly Ala Gly Val Val Glu Thr Pro Arg
        530               535               540

Ser Ala Leu Lys Val Thr Ala Gln Pro Asn Gly Val Leu Leu Gly Asn
545               550               555               560

Tyr Val Val Leu Ser Pro Gln Thr Val Leu Lys Ser Ser Lys Leu Ala
                565               570               575

Pro Val His Pro Leu Ala Glu Gln Val Lys Ile Ile Thr His Asn Gly
                580               585               590

Arg Ala Gly Arg Tyr Gln Val Asp Gly Tyr Asp Gly Arg Val Leu Leu
            595               600               605

Pro Cys Gly Ser Ala Ile Pro Val Pro Glu Phe Gln Ala Leu Ser Glu
            610               615               620

Ser Ala Thr Met Val Tyr Asn Glu Arg Glu Phe Val Asn Arg Lys Leu
625               630               635               640

Tyr His Ile Ala Val His Gly Pro Ser Leu Asn Thr Asp Glu Glu Asn
                645               650               655

Tyr Glu Lys Val Arg Ala Glu Arg Thr Asp Ala Glu Tyr Val Phe Asp
            660               665               670

Val Asp Lys Lys Cys Cys Val Lys Arg Glu Glu Ala Ser Gly Leu Val
            675               680               685

Leu Val Gly Glu Leu Thr Asn Pro Pro Phe His Glu Phe Ala Tyr Glu
        690               695               700

Gly Leu Lys Ile Arg Pro Ser Ala Pro Tyr Lys Thr Thr Val Val Gly
705               710               715               720

Val Phe Gly Val Pro Gly Ser Gly Lys Ser Ala Ile Ile Lys Ser Leu
                725               730               735

Val Thr Lys His Asp Leu Val Thr Ser Gly Lys Lys Glu Asn Cys Gln
            740               745               750

Glu Ile Val Asn Asp Val Lys Lys His Arg Gly Leu Asp Ile Gln Ala
            755               760               765

Lys Thr Val Asp Ser Ile Leu Leu Asn Gly Cys Arg Arg Ala Val Asp
        770               775               780

Ile Leu Tyr Val Asp Glu Ala Phe Ala Cys His Ser Gly Thr Leu Leu
785               790               795               800

Ala Leu Ile Ala Leu Val Lys Pro Arg Ser Lys Val Val Leu Cys Gly
                805               810               815

Asp Pro Lys Gln Cys Gly Phe Phe Asn Met Met Gln Leu Lys Val Asn
            820               825               830

Phe Asn His Asn Ile Cys Thr Glu Val Cys His Lys Ser Ile Ser Arg
            835               840               845

Arg Cys Thr Arg Pro Val Thr Ala Ile Val Ser Thr Leu His Tyr Gly
        850               855               860

Gly Lys Met Arg Thr Thr Asn Pro Cys Asn Lys Pro Ile Ile Ile Asp
865               870               875               880

Thr Thr Gly Gln Thr Lys Pro Lys Pro Gly Asp Ile Val Leu Thr Cys
                885               890               895
```

Phe Arg Gly Trp Val Lys Gln Leu Gln Leu Asp Tyr Arg Gly His Glu
            900               905               910

Val Met Thr Ala Ala Ala Ser Gln Gly Leu Thr Arg Lys Gly Val Tyr
            915               920               925

Ala Val Arg Gln Lys Val Asn Glu Asn Pro Leu Tyr Ala Pro Ala Ser
    930               935               940

Glu His Val Asn Val Leu Leu Thr Arg Thr Glu Asp Arg Leu Val Trp
945               950               955               960

Lys Thr Leu Ala Gly Asp Pro Trp Ile Lys Val Leu Ser Asn Ile Pro
                965               970               975

Gln Gly Asn Phe Thr Ala Thr Leu Glu Glu Trp Gln Glu Glu His Asp
            980               985               990

Lys Ile Met Lys Val Ile Glu Gly  Pro Ala Ala Pro Val  Asp Ala Phe
        995               1000               1005

Gln Asn  Lys Ala Asn Val Cys  Trp Ala Lys Ser Leu  Val Pro Val
    1010               1015               1020

Leu Asp  Thr Ala Gly Ile Arg  Leu Thr Ala Glu Glu  Trp Ser Thr
    1025               1030               1035

Ile Ile  Thr Ala Phe Lys Glu  Asp Arg Ala Tyr Ser  Pro Val Val
    1040               1045               1050

Ala Leu  Asn Glu Ile Cys Thr  Lys Tyr Tyr Gly Val  Asp Leu Asp
    1055               1060               1065

Ser Gly  Leu Phe Ser Ala Pro  Lys Val Ser Leu Tyr  Tyr Glu Asn
    1070               1075               1080

Asn His  Trp Asp Asn Arg Pro  Gly Gly Arg Met Tyr  Gly Phe Asn
    1085               1090               1095

Ala Ala  Thr Ala Ala Arg Leu  Glu Ala Arg His Thr  Phe Leu Lys
    1100               1105               1110

Gly Gln  Trp His Thr Gly Lys  Gln Ala Val Ile Ala  Glu Arg Lys
    1115               1120               1125

Ile Gln  Pro Leu Ser Val Leu  Asp Asn Val Ile Pro  Ile Asn Arg
    1130               1135               1140

Arg Leu  Pro His Ala Leu Val  Thr Glu Tyr Lys Thr  Val Lys Gly
    1145               1150               1155

Ser Arg  Val Glu Trp Leu Val  Asn Lys Val Arg Gly  Tyr His Val
    1160               1165               1170

Leu Leu  Val Ser Glu Tyr Asn  Leu Ala Leu Pro Arg  Arg Arg Val
    1175               1180               1185

Thr Trp  Leu Ser Pro Leu Asn  Val Thr Gly Ala Asp  Arg Cys Tyr
    1190               1195               1200

Asp Leu  Ser Leu Gly Leu Pro  Ala Asp Ala Gly Arg  Phe Asp Leu
    1205               1210               1215

Val Phe  Val Asn Ile His Thr  Glu Phe Arg Ile His  His Tyr Gln
    1220               1225               1230

Gln Cys  Val Asp His Ala Met  Lys Leu Gln Met Leu  Gly Gly Asp
    1235               1240               1245

Ala Leu  Arg Leu Leu Lys Pro  Gly Gly Ser Leu Leu  Met Arg Ala
    1250               1255               1260

Tyr Gly  Tyr Ala Asp Lys Ile  Ser Glu Ala Val Val  Ser Ser Leu
    1265               1270               1275

Ser Arg  Lys Phe Ser Ser Ala  Arg Val Leu Arg Pro  Asp Cys Val
    1280               1285               1290

-continued

```
Thr Ser  Asn Thr Glu Val Phe  Leu Leu Phe Ser Asn  Phe Asp Asn
    1295              1300              1305

Gly Lys  Arg Pro Ser Thr Leu  His Gln Met Asn Thr  Lys Leu Ser
    1310              1315              1320

Ala Val  Tyr Ala Gly Glu Ala  Met His Thr Ala Gly  Cys Ala Pro
    1325              1330              1335

Ser Tyr  Arg Val Lys Arg Ala  Asp Ile Ala Thr Cys  Thr Glu Ala
    1340              1345              1350

Ala Val  Val Asn Ala Ala Asn  Ala Arg Gly Thr Val  Gly Asp Gly
    1355              1360              1365

Val Cys  Arg Ala Val Ala Lys  Lys Trp Pro Ser Ala  Phe Lys Gly
    1370              1375              1380

Glu Ala  Thr Pro Val Gly Thr  Ile Lys Thr Val Met  Cys Gly Ser
    1385              1390              1395

Tyr Pro  Val Ile His Ala Val  Ala Pro Asn Phe Ser  Ala Thr Thr
    1400              1405              1410

Glu Ala  Glu Gly Asp Arg Glu  Leu Ala Ala Val Tyr  Arg Ala Val
    1415              1420              1425

Ala Ala  Glu Val Asn Arg Leu  Ser Leu Ser Ser Val  Ala Ile Pro
    1430              1435              1440

Leu Leu  Ser Thr Gly Val Phe  Ser Gly Gly Arg Asp  Arg Leu Gln
    1445              1450              1455

Gln Ser  Leu Asn His Leu Phe  Thr Ala Met Asp Ala  Thr Asp Ala
    1460              1465              1470

Asp Val  Thr Ile Tyr Cys Arg  Asp Lys Ser Trp Glu  Lys Lys Ile
    1475              1480              1485

Gln Glu  Ala Ile Asp Thr Arg  Thr Ala Val Glu Leu  Leu Asn Asp
    1490              1495              1500

Asp Val  Glu Leu Thr Thr Asp  Leu Val Arg Val His  Pro Asp Ser
    1505              1510              1515

Ser Leu  Val Gly Arg Lys Gly  Tyr Ser Thr Thr Asp  Gly Ser Leu
    1520              1525              1530

Tyr Ser  Tyr Phe Glu Gly Thr  Lys Phe Asn Gln Ala  Ala Ile Asp
    1535              1540              1545

Met Ala  Glu Ile Leu Thr Leu  Trp Pro Arg Leu Gln  Glu Ala Asn
    1550              1555              1560

Glu Gln  Ile Cys Leu Tyr Ala  Leu Gly Glu Thr Met  Asp Asn Ile
    1565              1570              1575

Arg Ser  Lys Cys Pro Val Asn  Asp Ser Asp Ser Ser  Thr Pro Pro
    1580              1585              1590

Arg Thr  Val Pro Cys Leu Cys  Arg Tyr Ala Met Thr  Ala Glu Arg
    1595              1600              1605

Ile Thr  Arg Leu Arg Ser His  Gln Val Lys Ser Met  Val Val Cys
    1610              1615              1620

Ser Ser  Phe Pro Leu Pro Lys  Tyr His Val Asp Gly  Val Gln Lys
    1625              1630              1635

Val Lys  Cys Glu Lys Val Leu  Leu Phe Asp Pro Thr  Val Pro Ser
    1640              1645              1650

Val Val  Ser Pro Arg Lys Tyr  Ala Ala Ser Thr Thr  Asp His Ser
    1655              1660              1665

Asp Arg  Ser Leu Arg Gly Phe  Asp Leu Asp Trp Thr  Thr Asp Ser
    1670              1675              1680

Ser Ser  Thr Ala Ser Asp Thr  Met Ser Leu Pro Ser  Leu Gln Ser
```

-continued

```
        1685            1690            1695

Cys Asp Ile Asp Ser Ile Tyr  Glu Pro Met Ala Pro  Ile Val Val
    1700            1705            1710

Thr Ala Asp Val His Pro Glu  Pro Ala Gly Ile Ala  Asp Leu Ala
    1715            1720            1725

Ala Asp Val His Pro Glu Pro  Ala Asp His Val Asp  Leu Glu Asn
    1730            1735            1740

Pro Ile Pro Pro Pro Arg Pro  Lys Arg Ala Ala Tyr  Leu Ala Ser
    1745            1750            1755

Arg Ala Ala Glu Arg Pro Val  Pro Ala Pro Arg Lys  Pro Thr Pro
    1760            1765            1770

Ala Pro Arg Thr Ala Phe Arg  Asn Lys Leu Pro Leu  Thr Phe Gly
    1775            1780            1785

Asp Phe Asp Glu His Glu Val  Asp Ala Leu Ala Ser  Gly Ile Thr
    1790            1795            1800

Phe Gly Asp Phe Asp Asp Val  Leu Arg Leu Gly Arg  Ala Gly Ala
    1805            1810            1815

Tyr Ile Phe Ser Ser Asp Thr  Gly Ser Gly His Leu  Gln Gln Lys
    1820            1825            1830

Ser Val Arg Gln His Asn Leu  Gln Cys Ala Gln Leu  Asp Ala Val
    1835            1840            1845

Glu Glu Glu Lys Met Tyr Pro  Pro Lys Leu Asp Thr  Glu Arg Glu
    1850            1855            1860

Lys Leu Leu Leu Leu Lys Met  Gln Met His Pro Ser  Glu Ala Asn
    1865            1870            1875

Lys Ser Arg Tyr Gln Ser Arg  Lys Val Glu Asn Met  Lys Ala Thr
    1880            1885            1890

Val Val Asp Arg Leu Thr Ser  Gly Ala Arg Leu Tyr  Thr Gly Ala
    1895            1900            1905

Asp Val Gly Arg Ile Pro Thr  Tyr Ala Val Arg Tyr  Pro Arg Pro
    1910            1915            1920

Val Tyr Ser Pro Thr Val Ile  Glu Arg Phe Ser Ser  Pro Asp Val
    1925            1930            1935

Ala Ile Ala Ala Cys Asn Glu  Tyr Leu Ser Arg Asn  Tyr Pro Thr
    1940            1945            1950

Val Ala Ser Tyr Gln Ile Thr  Asp Glu Tyr Asp Ala  Tyr Leu Asp
    1955            1960            1965

Met Val Asp Gly Ser Asp Ser  Cys Leu Asp Arg Ala  Thr Phe Cys
    1970            1975            1980

Pro Ala Lys Leu Arg Cys Tyr  Pro Lys His His Ala  Tyr His Gln
    1985            1990            1995

Pro Thr Val Arg Ser Ala Val  Pro Ser Pro Phe Gln  Asn Thr Leu
    2000            2005            2010

Gln Ser Val Leu Ala Ala Ala  Thr Lys Arg Asn Cys  Asn Val Thr
    2015            2020            2025

Gln Met Arg Glu Leu Pro Thr  Met Asp Ser Ala Val  Phe Asn Val
    2030            2035            2040

Glu Cys Phe Lys Arg Tyr Ala  Cys Ser Gly Glu Tyr  Trp Glu Glu
    2045            2050            2055

Tyr Ala Lys Gln Pro Ile Arg  Ile Thr Thr Glu Asn  Ile Thr Thr
    2060            2065            2070

Tyr Val Thr Lys Leu Lys Gly  Pro Lys Ala Ala Ala  Leu Phe Ala
    2075            2080            2085
```

-continued

```
Lys Thr His Asn Leu Val Pro Leu Gln Glu Val Pro Met Asp Arg
2090             2095             2100

Phe Thr Val Asp Met Lys Arg Asp Val Lys Val Thr Pro Gly Thr
2105             2110             2115

Lys His Thr Glu Glu Arg Pro Lys Val Gln Val Ile Gln Ala Ala
2120             2125             2130

Glu Pro Leu Ala Thr Ala Tyr Leu Cys Gly Ile His Arg Glu Leu
2135             2140             2145

Val Arg Arg Leu Asn Ala Val Leu Arg Pro Asn Val His Thr Leu
2150             2155             2160

Phe Asp Met Ser Ala Glu Asp Phe Asp Ala Ile Ile Ala Ser His
2165             2170             2175

Phe His Pro Gly Asp Pro Val Leu Glu Thr Asp Ile Ala Ser Phe
2180             2185             2190

Asp Lys Ser Gln Asp Asp Ser Leu Ala Leu Thr Gly Leu Met Ile
2195             2200             2205

Leu Glu Asp Leu Gly Val Asp Gln Tyr Leu Leu Asp Leu Ile Glu
2210             2215             2220

Ala Ala Phe Gly Glu Ile Ser Ser Cys His Leu Pro Thr Gly Thr
2225             2230             2235

Arg Phe Lys Phe Gly Ala Met Met Lys Ser Gly Met Phe Leu Thr
2240             2245             2250

Leu Phe Ile Asn Thr Val Leu Asn Ile Thr Ile Ala Ser Arg Val
2255             2260             2265

Leu Glu Gln Arg Leu Thr Asp Ser Ala Cys Ala Ala Phe Ile Gly
2270             2275             2280

Asp Asp Asn Ile Val His Gly Val Ile Ser Asp Lys Leu Met Ala
2285             2290             2295

Glu Arg Cys Ala Ser Trp Val Asn Met Glu Val Lys Ile Ile Asp
2300             2305             2310

Ala Val Met Gly Glu Lys Pro Pro Tyr Phe Cys Gly Gly Phe Ile
2315             2320             2325

Val Phe Asp Ser Val Thr Gln Thr Ala Cys Arg Val Ser Asp Pro
2330             2335             2340

Leu Lys Arg Leu Phe Lys Leu Gly Lys Pro Leu Thr Ala Glu Asp
2345             2350             2355

Lys Gln Asp Glu Asp Arg Arg Arg Ala Leu Ser Asp Glu Val Ser
2360             2365             2370

Lys Trp Phe Arg Thr Gly Leu Gly Ala Glu Leu Glu Val Ala Leu
2375             2380             2385

Thr Ser Arg Tyr Glu Val Glu Gly Cys Lys Ser Ile Leu Ile Ala
2390             2395             2400

Met Ala Thr Leu Ala Arg Asp Ile Lys Ala Phe Lys Lys Leu Arg
2405             2410             2415

Gly Pro Val Ile His Leu Tyr Gly Gly Pro Arg Leu Val Arg
2420             2425             2430
```